(12) United States Patent
Jackson et al.

(10) Patent No.: US 6,887,843 B1
(45) Date of Patent: May 3, 2005

(54) CHLAMYDIA PROTEIN, GENE SEQUENCE AND USES THEREOF

(75) Inventors: W. James Jackson, Marriottsville, MD (US); John L. Pace, San Anselmo, CA (US)

(73) Assignee: Antex Biologics, Inc., Gaithersburg, MD (US)

( * ) Notice: Subject to any disclaimer, the term of this patent is extended or adjusted under 35 U.S.C. 154(b) by 0 days.

(21) Appl. No.: 09/542,520

(22) Filed: Apr. 3, 2000

Related U.S. Application Data

(63) Continuation of application No. PCT/US98/20737, filed on Oct. 1, 1998, which is a continuation-in-part of application No. 08/942,596, filed on Oct. 2, 1997.

(51) Int. Cl.[7] .................. A61K 38/00; A61K 39/38; A61K 39/02; A01N 25/00
(52) U.S. Cl. ................. 514/2; 514/885; 514/931; 514/937; 424/184.1; 424/190.1
(58) Field of Search .................. 435/69.1, 252.3, 435/320.1; 536/23.1; 424/184.11, 190.1; 514/2, 885, 931, 937

(56) References Cited

U.S. PATENT DOCUMENTS

| | | |
|---|---|---|
| 4,427,782 A | 1/1984 | Caldwell et al. |
| 5,071,962 A | 12/1991 | Morrison et al. |
| 5,516,638 A | 5/1996 | Urnovitz et al. |
| 5,725,863 A | 3/1998 | Daniels et al. |

FOREIGN PATENT DOCUMENTS

| | | |
|---|---|---|
| EP | 0 818 681 A1 | 1/1998 |
| WO | WO 98/10789 | 3/1998 |

OTHER PUBLICATIONS

Pal et al., Infection & Immunity, 65: 3361–3369, Aug. (1997).
Christiansen et al., Scand J Infect Dis Suppl, 104:5–10 (1997).
Sandbutte et al., Veterinary Microbiology, 48:269–282 (1996).
Birkelund et al., Infection & Immunity, 56(3):654–59, Mar. (1988).
Buenida et al., FEMS Microbiol. Lttrs., May 1, 150(1):113–119 (1997).
Caldwell, et al., Infec. Immun., 31(3):1161–1176 (1981).
Cerrone et al., Infec. Immun., 59(1):79–90 (1991).
Chen et al., Molecular Microbiology 11(3):501–507 (1994).
Li et al., PNAS 77(6):3211–14 (1980).
DeSa et al., Infection & Immunity, Dec., 63(12):4912–16 (1995).
Murdin et al., Infec. Immun., 63(3):1116–1121 (1995).
Murdin et al., Infec. Immun., 61(10):4406–4414 (1993).
Sexton et al., J. of Immunol., 152(4):1861–72 (1994).
Su et al., PNAS 93:1143–48 (1986).
Swanson et al., Infec. Immun., 38(2):502–507 (1990).
Wagar et al., Infec. Immun., 56(7):1678–1684 (1988).
Zhang et al., Cell, 69:861–869 (1992).
Herring et al., FEMS Microbiol Letts. 65:153–158 (1989).
Tan et al., Infect Immun. 58(9) 3101–3108 (1990).
Zhang et al., Nucleic Acids Res. 18(4):1061 (1990).
Stephens et al., J. Bacteriol 168:1277–82 (1986).
WO 95/12411 published May 11, 1995 by Sabara.
WO 99/31236 published Oct. 10, 1996 by Prieels.

*Primary Examiner*—Gary Kunz
*Assistant Examiner*—Sharon Turner
(74) *Attorney, Agent, or Firm*—John M. Naber

(57) ABSTRACT

A high molecular weight ("HMW") protein of Chlamydia, the amino acid sequence thereof, and antibodies that specifically bind the HMW protein are disclosed as well as the nucleic acid sequence encoding the same. Also disclosed are prophylactic and therapeutic compositions, comprising the HMW protein, a fragment thereof, or an antibody that specifically binds the HMW protein or a protein thereof, or the nucleotide sequence encoding the HMW protein or a fragment thereof, including vaccines.

10 Claims, 11 Drawing Sheets

Figure 1:
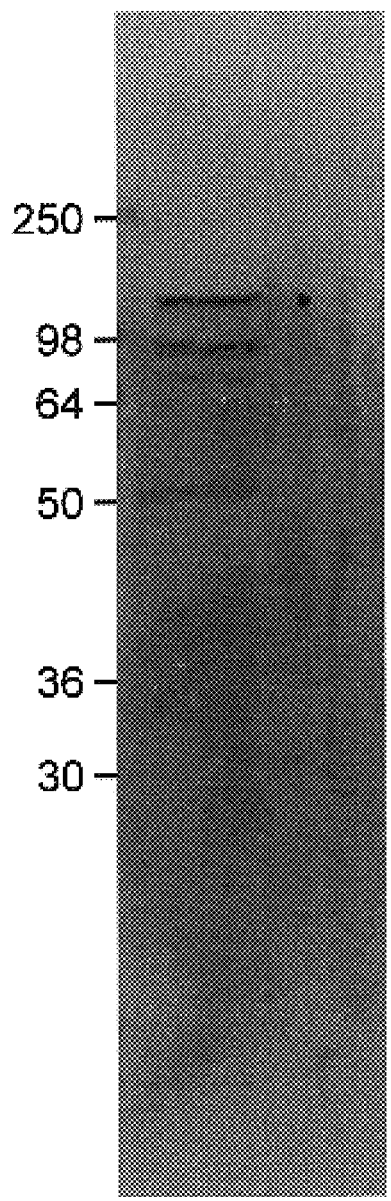

```
GGGCAAAACTCTTCCCCCCGGGATTTATATGGGAAAGGGGAAACTTTGGC
CCGTATTCAAGCCGCCACGGGTTTTGGGGCGGAATGAATTTTTTCGTTCCG
GAAAAAGTAATTCCCCGGGAACGTAGGGTATCGGTTTCATAGGCTCGCCA
AATGGGATATAGGTGGAAAGGTAAAAAAAACTGAGCCAAGCAAAGGATAG
AGAAGTCTTGTAATCATCGCAGGTTAAAGGGGGGATGTTATTTTAGCCTG
CAAATAGTGTAATTATTGGATCCTGTAAAGAGAAAAGGACGAATGCGCTG
AAGATAAGAACATTTATTGATATTAAATTATTAATTTTTTATGAAGCGGA
GTAATTAATTTTATCTCTCAGCTTTTGTGTGATGCAAACGTCTTTCCATA
AGTTCTTTCTTTCAATGATTCTAGCTTATTCTTGCTGCTCTTTAAATGGG
GGGGGATATGCAGCAGAAATCATGGTTCCTCAAGGAATTTACGATGGGGA
GACGTTAACTGTATCATTTCCCTATACTGTTATAGGAGATCCGAGTGGGA
CTACTGTTTTTTCTGCAGGAGAGTTAACATTAAAAAATCTTGACAATTCT
ATTGCAGCTTTGCCTTTAAGTTGTTTTGGGAACTTATTAGGGAGTTTTAC
TGTTTTAGGGAGAGGACACTCGTTGACTTTCGAGAACATACGGACTTCTA
CAAATGGGGCAGCTCTAAGTAATAGCGCTGCTGATGGACTGTTTACTATT
GAGGGTTTTAAAGAATTATCCTTTTCCAATTGCAATTCATTACTTGCCGT
ACTGCCTGCTGCAACGACTAATAAGGGTAGCCAGACTCCGACGACAACAT
CTACACCGTCTAATGGTACTATTTATTCTAAAACAGATCTTTTGTTACTC
AATAATGAGAAGTTCTCATTCTATAGTAATTTAGTCTCTGGAGATGGGGG
AGCTATAGATGCTAAGAGCTTAACGGTTCAAGGAATTAGCAAGCTTTGTG
TCTTCCAAGAAAATACTGCTCAAGCTGATGGGGGAGCTTGTCAAGTAGTC
ACCAGTTTCTCTGCTATGGCTAACGAGGCTCCTATTGCCTTTGTAGCGAA
TGTTGCAGGAGTAAGAGGGGGAGGGATTGCTGCTGTTCAGGATGGGCAGC
AGGGAGTGTCATCATCTACTTCAACAGAAGATCCAGTAGTAAGTTTTTCC
AGAAATACTGCGGTAGAGTTTGATGGGAACGTAGCCCGAGTAGGAGGAGG
GATTTACTCCTACGGGAACGTTGCTTTCCTGAATAATGGAAAAACCTTGT
TTCTCAACAATGTTGCTTCTCCTGTTTACATTGCTGCTAAGCAACCAACA
AGTGGACAGGCTTCTAATACGAGTAATAATTACGGAGATGGAGGAGCTAT
CTTCTGTAAGAATGGTGCGCAAGCAGGATCCAATAACTCTGGATCAGTTT
CCTTTGATGGAGAGGGAGTAGTTTTCTTTAGTAGCAATGTAGCTGCTGGG
AAAGGGGGAGCTATTTATGCCAAAAAGCTCTCGGTTGCTAACTGTGGCCC
TGTACAATTTTTAAGGAATATCGCTAATGATGGTGGAGCGATTTATTTAG
GAGAATCTGGAGAGCTCAGTTTATCTGCTGATTATGGAGATATTATTTTC
```

FIG. 2A

```
GATGGGAATCTTAAAAGAACAGCCAAAGAGAATGCTGCCGATGTTAATGG
CGTAACTGTGTCCTCACAAGCCATTTCGATGGGATCGGGAGGGAAAATAA
CGACATTAAGAGCTAAAGCAGGGCATCAGATTCTCTTTAATGATCCCATC
GAGATGGCAAACGGAAATAACCAGCCAGCGCAGTCTTCCAAACTTCTAAA
AATTAACGATGGTGAAGGATACACAGGGGATATTGTTTTTGCTAATGGAA
GCAGTACTTTGTACCAAAATGTTACGATAGAGCAAGGAAGGATTGTTCTT
CGTGAAAAGGCAAAATTATCAGTGAATTCTCTAAGTCAGACAGGTGGGAG
TCTGTATATGGAAGCTGGGAGTACATGGGATTTTGTAACTCCACAACCAC
CACAACAGCCTCCTGCCGCTAATCAGTTGATCACGCTTTCCAATCTGCAT
TTGTCTCTTTCTTCTTTGTTAGCAAACAATGCAGTTACGAATCCTCCTAC
CAATCCTCCAGCGCAAGATTCTCATCCTGCAGTCATTGGTAGCACAACTG
CTGGTTCTGTTACAATTAGTGGGCCTATCTTTTTTGAGGATTTGGATGAT
ACAGCTTATGATAGGTATGATTGGCTAGGTTCTAATCAAAAAATCAATGT
CCTGAAATTACAGTTAGGGACTAAGCCCCCAGCTAATGCCCCATCAGATT
TGACTCTAGGGAATGAGATGCCTAAGTATGGCTATCAAGGAAGCTGGAAG
CTTGCGTGGGATCCTAATACAGCAAATAATGGTCCTTATACTCTGAAAGC
TACATGGACTAAAACTGGGTATAATCCTGGGCCTGAGCGAGTAGCTTCTT
TGGTTCCAAATAGTTTATGGGGATCCATTTTAGATATACGATCTGCGCAT
TCAGCAATTCAAGCAAGTGTGGATGGGCGCTCTTATTGTCGAGGATTATG
GGTTTCTGGAGTTTCGAATTTCTTCTATCATGACCGCGATGCTTTAGGTC
AGGGATATCGGTATATTAGTGGGGGTTATTCCTTAGGAGCAAACTCCTAC
TTTGGATCATCGATGTTTGGTCTAGCATTTACCGAAGTATTTGGTAGATC
TAAAGATTATGTAGTGTGTCGTTCCAATCATCATGCTTGCATAGGATCCG
TTTATCTATCTACCCAACAAGCTTTATGTGGATCCTATTTGTTCGGAGAT
GCGTTTATCCGTGCTAGCTACGGGTTTGGGAATCAGCATATGAAAACCTC
ATATACATTTGCAGAGGAGAGCGATGTTCGTTGGGATAATAACTGTCTGG
CTGGAGAGATTGGAGCGGGATTACCGATTGTGATTACTCCATCTAAGCTC
TATTTGAATGAGTTGCGTCCTTTCGTGCAAGCTGAGTTTTCTTATGCCGA
TCATGAATCTTTTACAGAGGAAGGCGATCAAGCTCGGGCATTCAAGAGCG
GACATCTCCTAAATCTATCAGTTCCTGTTGGAGTGAAGTTTGATCGATGT
TCTAGTACACATCCTAATAAATATAGCTTTATGGCGGCTTATATCTGTGA
TGCTTATCGCACCATCTCTGGTACTGAGACAACGCTCCTATCCCATCAAG
AGACATGGACAACAGATGCCTTTCATTTAGCAAGACATGGAGTTGTGGTT
AGAGGATCTATGTATGCTTCTCTAACAAGTAATATAGAAGTATATGGCCA
TGGAAGATATGAGTATCGAGATGCTTCTCGAGGCTATGGTTTGAGTGCAG
```

FIG. 2B

```
GAAGTAGAGTCCGGTTCTAAAAATATTGGTTAGATAGTTAAGTGTTAGCG
ATGCCTTTTTCTTTGAGATCTACATCATTTTGTTTTTTAGCTTGTTTGTG
TTCCTATTCGTATGGATTCGCGAGCTCTCCTCAAGTGTTAACGCCTAATG
TAACCACTCCTTTTAAGGGAGACGATGTTTACTTGAATGGAGACTGCGCT
TTTGTCAATGTCTATGCAGGAGCTGAAGAAGGTTCGATTATCTCAGCTAA
TGGCGACAATTTAACGATTACCGGACAAAACCATACATTATCATTTACAG
ATTCTCAAGGGCCAGTTCTTCAAAATTATGCCTTCATTTCAGCAGGAGAG
ACACTTACTCTGAGAGATTTTCGAGTCTGATGTTCTCGAAAAATGTTTC
TTGCGGAGAAAAGGGAATGATCTCCGGGAAAACCGTGAGTATTTCCGGAG
CAGGCGAAGTGATTTTCTGGGATAACTCCGTGGGGTATTCTCCTTTATCT
ACTGTGCCAACCTCATCATCAACTCCGCCTGCTCCAACAGTTAGTGATGC
TCGGAAAGGGTCTATTTTTTCTGTAGAGACTAGTTTGGAGATCTCAGGCG
TCAAAAAAGGGGTCATGTTCGATAATAATGCCGGGAATTTCGGAACAGTT
TTTCGAGGTAAGAATAATAATAATGCTGGTGGTGGAGGCAGTGGGTTCCG
CTACACCATCAAGTACGACTTTTACAGTTAAAAACTGTAAAGGGAAAGTT
TCTTTCACAGATAACGTAGCCTCTTGCGGAGGCGGAGTGGTTTATAAAGG
CATTGTGCTTTTCAAAGACAATGAAGGAGGCATATTCTTCCGAGGGAACA
CAGCATACGATGATTTAAGGATTCTTGCTGCTACTAATCAGGATCAGAAT
ACGGAGACAGGAGGCGGTGGAGGAGTTATTTGCTCTCCAGATGATTCTGT
AAAGTTTGAAGGCAATAAAGGTTCTATTGTTTTTGATTACAACTTTGCAA
AAGGCAGAGGCGGAAGCATCCTAACGAAAGAATTC
```

FIG. 2C

MQTSFHKFFLSMILAYSCCSLNGGGYAAEIMVPQGIYDGETLTVSFPYTV
IGDPSGTTVFSAGELTLKNLDNSIAALPLSCFGNLLGSFTVLGRGHSLTF
ENIRTSTNGAALSNSAADGLFTIEGFKELSFSNCNSLLAVLPAATTNKGS
QTPTTTSTPSNGTIYSKTDLLLLNNEKFSFYSNLVSGDGGAIDAKSLTVQ
GISKLCVFQENTAQADGGACQVVTSFSAMANEAPIAFVANVAGVRGGGIA
AVQDGQQGVSSSTSTEDPVVSFSRNTAVEFDGNVARVGGGIYSYGNVAFL
NNGKTLFLNNVASPVYIAAKQPTSGQASNTSNNYGDGGAIFCKNGAQAGS
NNSGSVSFDGEGVVFFSSNVAAGKGGAIYAKKLSVANCGPVQFLRNIAND
GGAIYLGESGELSLSADYGDIIFDGNLKRTAKENAADVNGVTVSSQAISM
GSGGKITTLRAKAGHQILFNDPIEMANGNNQPAQSSKLLKINDGEGYTGD
IVFANGSSTLYQNVTIEQGRIVLREKAKLSVNSLSQTGGSLYMEAGSTWD
FVTPQPPQQPPAANQLITLSNLHLSLSSLLANNAVTNPPTNPPAQDSHPA
VIGSTTAGSVTISGPIFFEDLDDTAYDRYDWLGSNQKINVLKLQLGTKPP
ANAPSDLTLGNEMPKYGYQGSWKLAWDPNTANNGPYTLKATWTKTGYNPG
PERVASLVPNSLWGSILDIRSAHSAIQASVDGRSYCRGLWVSGVSNFFYH
DRDALGQGYRYISGGYSLGANSYFGSSMFGLAFTEVFGRSKDYVVCRSNH
HACIGSVYLSTQQALCGSYLFGDAFIRASYGFGNQHMKTSYTFAEESDVR
WDNNCLAGEIGAGLPIVITPSKLYLNELRPFVQAEFSYADHESFTEEGDQ
ARAFKSGHLLNLSVPVGVKFDRCSSTHPNKYSFMAAYICDAYRTISGTET
TLLSHQETWTTDAFHLARHGVVVRGSMYASLTSNIEVYGHGRYEYRDASR
GYGLSAGSRVRF

FIG.3

```
L2                                        EIMVPQGIYDGETLTVSFPYTVIGDPSGTTVF
F
B

100*
L2    SAGELTLKNLDNSIAALPLSCFGNLLGSFTVLGRGHSLTFENIRTSTNGAALSNSAADGL
F                                                             D  NS
B                                                             D  NS

L2    FTIEGFKELSFSNCNSLLAVLPAATTNKGSQTPTTTSTPSNGTIYSKTDLLLLNNEKFSFY
F                    |              N       |
B                    P              N        S

200*
L2    SNLVSGDGGAIDAKSLTVQGISKLCVFQENTAQADGGACQVVTSFSAMANEAPIAFVA
F        |        T                                          I
B        S

L2    NVAGVRGGGIAAVQDGQQGVSSSTSTEDPVVSFSRNTAVEFDGNVARVGGGIYSYGNV
F
B

*300
L2    AFLNNGKTLFLNNVASPVYIAAKQPTSGQASNTSNNYGDGGAIFCKNGAQAGSNNSGS
F              E        N       D                    [A]
B              E        N       D                    [A]

400*
L2    VSFDGEGVVFFSSNVAAGKGGAIYAKKLSVANCPGPVQFLRNIANDGGAIYLGESGELSL
F                                          |  G
B                                          L  G

L2    SADYGDIIFDGNLKRTAKENAADVNGVTVSSQAISMGSGGKITTLRAKAGHQILFNDPIE
F             |
B             M

500*                              EcoRI-I
L2    MANGNNQPAQSSKLLKINDGEGYTGDIVFANGSSTLYQNVTIEQGRIVLREKAKLSVNSL
F              EP                       N
B              EP                       N
```

FIG. 6A

```
L2  SQTGGSLYMEAGSTWDFVTPQPPQQPPAANQL ITLSNLHLSLSSLLANNAV TNPPTNP
F                                  V
B                                  L           S

600*
L2  PAQDSHPAVIGSTTAGSVTISGPIFFEDLDDTAYDRYDWLGSNQKINVLKLQLGTKPPA
F         P         P      F                      D        Q S
B                                                 D        Q S

700*
L2  NAPSDLTLGNEMPKYGYQGSWKLAWDPNTANNGPYTLKATWTKTGYNPGPERVASLV
F
B

L2  PNSLWGSILDIRSAHSAIQASVDGRSYCRGLWVSGVSNFFYHDRDALGQGYRYISGGYS
F                                        S
B

800*
L2  LGANSYFGSSMFGLAFTEVFGRSKDYVVCRSNHHACIGSVYLSTQQALCGSYLFGDAFI
F                                  K                  V
B                                  K                  V

L2  RASYGFGNQHMKTSYTFAEESDVRWDNNCLAGEIGAGLPIVITPSKLYLNELRPFVQAEF
F               I          V  V          T
B               C          V  V

900*
L2  SYADHESFTEEGDQARAFKSGHLLNLSVPVGVKFDRCSSTHPNKYSFMAAYICDAYRTI
F                       R  M                              G
B                       R  M                              G

1000*
L2  SGTETTLLSHQETWTTDAFHLARHGVVVRGSMYASLTSNIEVYGHGRYEYRDASRGYGL
F      Q                    I                        T
B      Q                    I                        T

1013*
L2  SAGSRVRF
F        K
B        K
```

FIG. 6B

CHLAMYDIA PROTEIN, GENE SEQUENCE AND USES THEREOF

This application is a continuation of PCT/US98/20737 filed Oct. 1, 1998 which is a continuation-in-part of U.S. patent application No. 08/942,596 filed Oct. 2, 1997.

1. FIELD OF THE INVENTION

The present invention generally relates to a high molecular weight ("HMW") protein of *Chlamydia*, the amino acid sequence thereof and antibodies, including cytotoxic antibodies, that specifically bind the HMW protein. The invention further encompasses prophylactic and therapeutic compositions comprising the HMW protein, a fragment thereof, or an antibody that specifically binds the HMW protein or a portion thereof or the nucleotide sequence encoding the HMW protein or a fragment thereof, including vaccines. The invention additionally provides methods of preventing, treating or ameliorating disorders in mammals and birds related to *Chlamydia* infections and for inducing immune responses to *Chlamydia*. The invention further provides isolated nucleotide sequences and degenerate sequences encoding the HMW protein, vectors having said sequences, and host cells containing said vectors. Diagnostic methods and kits are also included.

2. BACKGROUND OF THE INVENTION

*Chlamydia* are prevalent human pathogens causing disorders such as sexually transmitted diseases, respiratory diseases including pneumonia, neonatal conjunctivitis, and blindness. *Chlamydia* are obligate intercellular bacteria that infect the epithelial lining of the lung, conjunctivae or genital tract. The most common species of *Chlamydia* include *Chlamydia trachomatis, Chlamydia psittaci, Chlamydia pecorum* and *Chlamydia pneumoniae*. Recently, the newly designated species of *Chlamydia, C. pneumoniae* (formerly *C. trachomatis* TWAR), has been implicated as a major cause of epidemic human pneumonitis and perhaps may play a role in atherosclerosis.

There are currently 18 recognized *C. trachomatis* serovars, causing trachoma and a broad spectrum of sexually transmitted diseases: with the A, B and C serovars being most frequently associated with trachoma, while the D-K serovars are the most common cause of genital infections.

*C. trachomatis* is the major cause of sexually transmitted disease in many industrialized countries, including the United States. While the exact incidence of *C. trachomatis* infection in the U.S. is not known, current epidemiological studies indicate that more than 4 million chlamydial infections occur each year, compared to an estimated 2 million gonococcal infections. While all racial, ethnic and socioeconomic groups are affected, the greatest prevalence of chlamydial infections occur among young, 12 to 20 year-old, sexually active individuals. Most genitourinary chlamydial infections are clinically asymptomatic. Prolonged carriage in both men and women is common. As many as 25% of men and 75% of women diagnosed as having chlamydial infections have no overt signs of infection. As a consequence, these asymptomatic individuals constitute a large reservoir that can sustain transmission of the agent within the community.

Far from being being, serious disease can develop from these infections including: urethritis, lymphogranuloma venereum (LGV), cervicitis, and epididymitis in males. Ascending infections from the endocervix commonly gives rise to endometritis, pelvic inflammatory disease (PID) and salpingitis which can cause tubal occlusion and lead ultimately to infertility.

*C. trachomatis* infection of neonates results from perinatal exposure to the mother's infected cervix. Nearly 70% of neonates born vaginally to mothers with chlamydial cervicitis become infected during delivery. The mucus membranes of the eye, oropharynx, urogenital tract and rectum are the primary sites of infection. Chlamydial conjunctivitis has become the most common form of ophthalmia neonatorum. Approximately 20–30% of exposed infants develop inclusion conjunctivitis within 14 days of delivery even after receiving prophylaxis with either silver nitrate or antibiotic ointment. *C. trachomatis* is also the leading cause of infant pneumonia in the United States. Nearly 10–20% of neonates delivered through an infected cervix will develop chlamydial pneumonia and require some type of medical intervention.

In developing countries, ocular infections of *C. trachomatis* cause trachoma, a chronic follicular conjunctivitis where repeated scar formation leads to distortion of the eyelids and eventual loss of sight. Trachoma is the world's leading cause of preventable blindness. The World Health Organization estimates that over 500 million people worldwide, including about 150 million children, currently suffer from active trachoma and over 6 million people have been blinded by this disease.

In industrialized countries, the costs associated with treating chlamydial infections are enormous. In the U.S., the annual cost of treating these diseases was estimated at $2.5–3 billion in 1992 and has been projected to exceed $8 billion by the year 2000.

One potential solution to this health crisis would be an effective chlamydial vaccine. Several lines of evidence suggest that developing an effective vaccine is feasible.

Studies in both humans and primates have shown that short-term protective immunity to *C. trachomatis* can be produced by vaccinating with whole *Chlamydia*. However, protection was characterized as short lived, serovar specific, and due to mucosal antibody. Additionally, in some vaccinees disease was exacerbated when these individuals became naturally infected with a serovar different from that used for immunization. This adverse reaction was ultimately demonstrated to be due to a delayed-type hypersensitivity response. Thus, the need exists to develop a subunit-based chlamydial vaccine capable of producing an efficacious but nonsensitizing immune response. Such a subunit vaccine may need to elicit both mucosal neutralizing secretory IgA antibody and/or cellular immune response to be efficacious.

Subunit vaccine development efforts to date have focused almost exclusively on the major outer membrane protein (MOMP). MOMP is an integral membrane protein of approximately 40 kDa in size and comprises up to about 60% of the infectious elementary body (EB) membrane protein (Caldwell, H. D., J. Kromhout, and L. Schachter. 1981. *Infect. Immun.*, 31:1161–1176). MOMP imparts structural integrity to the extracellular EB and is thought to function as a porin-like molecule when the organism is growing intracellularly and is metabolically active. With the exception of four surface exposed variable domains (VDI-VDIV), MOMP is highly conserved among all 18 serovars. MOMP is highly immunogenic and can elicit a local neutralizing anti-Chlamydia antibody. However, problems exists with this approach.

To date, most MOMP-specific neutralizing epitopes that have been mapped are located within the VD regions and thus give rise only to serovar-specific antibody. Attempts to combine serovar-specific epitopes in various vaccine vectors (e.g. poliovirus) to generate broadly cross-reactive neutralizing antibodies have been only marginally successful (Murdin, A. D., H. Su, D. S. Manning, M. H. Klein, M. J. Parnell, and H. D. Caldwell. 1993. *Infect. Immun.,* 61:4406–4414; Murdin, A. D., H. Su, H. H. Klein, and H. D. Caldwell. 1995. *Infect. Immun.,* 63:1116–1121).

Two other major outer membrane proteins in *C. trachomatis,* the 60 kDa and 12 kDa cysteine-rich proteins, as well as the surface-exposed lipoplysaccharide, are highly immunogenic but, unlike MOMP, have not been shown to induce a neutralizing antibody (Cerrone et al., 1991, *Infect. Immun.,* 59:79–90). therefore, there remains a need for a novel subunit-based chlamydial vaccine.

3. SUMMARY OF THE INVENTION

An object of the present invention is to provide an isolated and substantially purified high molecular weight protein of a *Chlamydia sp.* ("HMW protein"), wherein the HMW protein has an apparent molecular weight of about 105–115 kDa, as determined by SDS-PAGE, or a fragment or analogue thereof. Preferably the HMW protein has substantially the amino acid sequence of any of SEQ ID Nos.: 2, 15 and 16. Preferred fragments of the HMW protein include SEQ ID Nos: 3, 17, and 25–37. As used herein, "substantially the sequence" is intended to mean that the sequence is at least 80%, more preferably at least 90% and most preferably at least 95% identical to the referenced sequence. Preferably, the HMW protein is an outer membrane protein. More preferably, the outer membrane HMW protein is surface localized. Preferably, the HMW protein has a heparin binding domain. Preferably, the HMW Protein has a porin-like domain. It is intended that all species of *Chlamydia* are included in this invention, however preferred species include *Chlamydia trachomatis, Chlamydia psittaci, Chlamydia percorum* and *Chlamydia pneumoniae.* The substantially purified HMW protein is at least 70 wt % pure, preferably at least about 90 wt % pure, and may be in the form of an aqueous solution thereof.

Also included in this invention are recombinant forms of the HMW protein, wherein in transformed *E. coli* cells, the expressed recombinant form of the HMW protein has an apparent molecular weight of about 105–115 kDa, as determined by SDS-PAGE, or a fragment or analogue thereof. The term HMW-derived polypeptide is intended to include fragments of the HMW protein; variants of wild-type HMW protein or fragment thereof, containing one or more amino acid deletions, insertions or substitutions; and chimeric proteins comprising a heterologous polypeptide fused to the C-terminal or N-terminal or internal segment of a whole or a portion of the HMW protein.

As used herein and in the claims, the term "HMW protein" refers to a native purified or recombinant purified high molecular weight protein of a species of *Chlamydia* wherein the apparent molecular weight (as determined by SDS-PAGE) is about 105–115 kDa. As used herein and in the claims, the term "rHMW protein" refers to recombinant HMW protein.

Another object of the present invention is to provide an isolated substantially pure nucleic acid molecule encoding a HMW protein or a fragment or an analogue thereof. Preferred is the nucleic acid sequence wherein the encoded HMW protein comprises the amino acid sequence of any of SEQ ID Nos.: 2, 15 and 16, or a fragment thereof, particularly SEQ ID Nos.: 3, 17, 25–37. Also included is an isolated nucleic acid molecule comprising a DNA sequence of any of SEQ ID Nos.: 1, 23–24 or a complementary sequence thereof; a fragment of the HMW DNA sequence having the nucleic acid sequence of any of SEQ ID Nos.: 4–14, 18–22 or the complimentary sequence thereto; and a nucleic acid sequence which hybridizes under stringent conditions to any one of the sequences described above. The nucleic acid that hybridizes under stringent conditions preferably has a sequence identity of about 70% with any of the sequences identified above, more preferably about 90%.

The production and use of derivatives and analogues of the HMW protein are within the scope of the present invention. In a specific embodiment, the derivative or analogue is functionally active, i.e., capable of exhibiting one or more functional activities associated with a full-length, wild-type HMW protein. As one example, such derivatives or analogues which have the desired immunogenicity or antigenicity can be used, for example, in immunoassays, for immunization, etc. A specific embodiment relates to a HMW fragment that can be bound by an anti-HMW antibody. Derivatives or analogues of HMW can be tested for the desired activity by procedures known in the art.

In particular, HMW derivatives can be made by altering HMW sequences by substitutions, additions or deletions that provide for functionally equivalent molecules. Due to the degeneracy of nucleotide coding sequences, other DNA sequences which encode substantially the same amino acid sequence as a HMW gene may be used in the practice of the present invention. These include but are not limited to nucleotide sequences comprising all or portions of genes which are altered by the substitution of different codons that encode a functionally equivalent amino acid residue within the sequence, thus producing a silent change. Likewise, the HMW derivatives of the invention include, but are not limited to, those containing, as a primary amino acid sequence, all or part of the amino acid sequence of a HMW protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a HMW protein consisting of at least 6 (continuous) amino acids of the HMW protein is provided. In other embodiments, the fragment consists of at least 7 to 50 amino acids of the HMW protein. In specific embodiments, such fragments are not larger than 35, 100 or 200 amino acids. Derivatives or analogues of HMW include but are not limited to those molecules comprising regions that are substantially homologous to HMW or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding HMW sequence, under stringent, moderately stringent, or nonstringent conditions.

By way of example and not limitation, useful computer homology programs include the following: Basic Local Alignment Search Tool (BLAST) (www.ncbi.nlm.nih.gov) (Altschul et al., 1990, J. of Molec. Biol., 215:403–410, "The BLAST Algorithm; Altschul et al., 1997, Nuc. Acids Res. 25:3389–3402) a heuristic search algorithm tailored to searching for sequence similarity which ascribes significance using the statistical methods of Karlin and Altschul 1990, Proc. Nat'l Acad. Sci. USA, 87:2264–68; 1993 Proc. Nat'l Acad. Sci. USA 90:5873–77. Five specific BLAST programs perform the following tasks:

1) The BLASTP program compares an amino acid query sequence against a protein sequence database.
2) The BLASTN program compares a nucleotide query sequence against a nucleotide sequence database.
3) The BLASTX program compares the six-frame conceptual translation products of a nucleotide query sequence (both strands) against a protein sequence database.
4) The TBLASTN program compares a protein query sequence against a nucleotide sequence database translated in all six reading frames (both strands).
5) The TBLASTX program compares the six-frame translations of a nucleotide query sequence against the six-frame translations of a nucleotide sequence database.

Smith-Waterman (database: European Bioinformatics Institute wwwz.ebi.ac.uk/bic_sw/) (Smith-Waterman, 1981, J. of Molec. Biol., 147:195–197) is a mathematically rigorous algorithm for sequence alignments.

FASTA (see Pearson et al., 1988, Proc. Nat'l Acad. Sci. USA, 85:2444–2448) is a heuristic approximation to the Smith-Waterman algorithm. For a general discussion of the procedure and benefits of the BLAST, Smith-Waterman and FASTA algorithms see Nicholas et al. 1998, "A Tutorial on Searching Sequence Databases and Sequence Scoring Methods" (www.psc.edu) and references cited therein.

The HMW derivatives and analogues of the invention can be produced by various methods known in the art. The manipulations which results in their production can occur at the gene or protein level. For example, the cloned HMW gene sequence can be modified by any of numerous strategies known in the art (Sambrook et al., 1989, Molecular Cloning, A Laboratory Manual, 2d Ed., Cold Spring Harbor Laboratory Press, Cold Spring Harbor, New York). The sequence can be cleaved at appropriate sites with restriction endonuclease(s), followed by further enzymatic modification if desired, isolated, and ligated in vitro. In the production of the gene encoding a derivative or analogue of HMW, care should be taken to ensure that the modified gene remains within the same translational reading frame as HMW, uninterrupted by translational stop signals, in the gene region where the desired HMW activity is encoded.

Additionally, the HMW-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the HMW sequence may also be made at the protein level. Included within the scope of the invention are HMW protein fragments or other derivatives or analogues which are differentially modified during or after translation, e.g., by glycosylation, lipidation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogues and derivatives of HMW can be chemically synthesized. For example, a peptide corresponding to a portion of a HMW protein which comprises the desired domain, or which mediates the desired activity in vitro, can be synthesized by use of a peptide synthesizer. Furthermore, if desired, nonclassical amino acids or chemical amino acid analogues can be introduced as a substitution or addition into the HMW sequence. Non-classical amino acids include but are not limited to the D-isomers of the common amino acids, α-amino, isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

Another object of the invention is to provide a recombinant expression vector adapted for transformation of a host or for delivery of a HMW protein to a host comprising the nucleic acid molecule of SEQ ID No.: 1, 23 or 24 or any fragment thereof. Preferably, the recombinant expression vector is adapted for transformation of a host and comprises an expression means operatively coupled to the nucleic acid molecule for expression by the host of said HMW protein or the fragment or analogue thereof. More preferred is the expression vector wherein the expression means includes a nucleic acid portion encoding a leader sequence for secretion from the host or an affinity domain coupled to either the N- or C-terminus of the protein or the fragment or analogue thereof.

A further aspect of the invention includes a transformed host cell containing an expression vector described above and the recombinant HMW protein or fragment or analogue thereof producible by the transformed host cell.

Still a further aspect of the invention is directed to a HMW protein recognizable by an antibody preparation that specifically binds to a peptide having the amino acid sequence of SEQ ID No. 2, 15–16 or a fragment or conservatively substituted analogue thereof.

Antigenic and/or immunogenic compositions are another aspect of the invention wherein the compositions comprise at least one component selected from the following group:

a) a HMW protein, wherein the molecular weight is about 105–115 kDa, as determined by SDS-PAGE, or a fragment or analogue thereof;
b) an isolated nucleic acid molecule encoding a HMW protein, or a fragment or analogue thereof;
c) an isolated nucleic acid molecule having the sequence of SEQ ID Nos. 1, 22, 23 or 24, the complimentary sequence thereto or a nucleic acid sequence which hybridizes under stringent conditions thereto or fragment thereof;

d) an isolated recombinant HMW protein, or fragment or analogue thereof, producible in a transformed host comprising an expression vector comprising a nucleic acid molecule as defined in b) or c) and expression means operatively coupled to the nucleic acid molecule for expression by the host of said HMW protein or the fragment or analogue thereof;

e) a recombinant vector comprising a nucleic acid encoding a HMW protein or fragment or analogue thereof;

f) a transformed cell comprising the vector of e) and optionally an adjuvant, and a pharmaceutically acceptable carrier or diluent therefor, said composition producing an immune response when administered to a host.

Preferred adjuvants include cholera holotoxin or subunits, *E. coli* heat labile holotoxin, subunits and mutant forms thereof, alum, QS21, and MPL. Particularly, preferred are alum, LTR192G, mLT and QS21.

Also included are methods for producing an immune response in a mammal or a bird comprising administering to said mammal, an effective amount of the antigenic or the immunogenic composition described above.

Another aspect of the invention is directed to antisera raised against the antigenic or immunogenic composition of the invention, and antibodies present in the antisera that specifically bind a HMW protein or a fragment or analogue thereof. Preferably the antibodies bind a HMW protein having the amino acid sequence of SEQ ID Nos.: 2, 15–16 or fragment or a conservatively substituted analogue thereof. Also included are monoclonal antibodies that specifically bind a HMW protein or a fragment or analogue thereof.

A further aspect of the invention includes pharmaceutical and vaccine compositions comprising an effective amount of at least one component selected from the following group:

a) a HMW protein, wherein the isolated protein molecular weight is about 105–115 kDa, as determined by SDS-PAGE, or a fragment or analogue thereof;

b) an isolated nucleic acid molecule encoding a HMW protein, or a fragment or analogue thereof;

c) an isolated nucleic acid molecule having the sequence of SEQ ID Nos.: 1, 22, 23 or 24 the complimentary sequence thereto or a nucleic acid sequence which hybridizes under stringent conditions thereto or a fragment thereof;

d) an isolated recombinant HMW protein, or fragment or analogue thereof producible in a transformed host comprising an expression vector comprising a nucleic acid molecule as defined in b) or c) and expression means operatively coupled to the nucleic acid molecule for expression by the host of said HMW protein of a *Chlamydia* species or the fragment or analogue thereof;

e) a recombinant vector, comprising a nucleic acid encoding a HMW protein or fragment or analogue thereof;

f) a transformed cell comprising the vector of e), g) antibodies that specifically bind the component of a), b), c), d) or e), and a pharmaceutically acceptable carrier or diluent therefor. Preferred are vaccine compositions which are effective at the mucosal level.

The invention also includes a diagnostic reagent which may include any one or more of the above mentioned aspects, such as the native HMW protein, the recombinant HMW protein, the nucleic acid molecule, the immunogenic composition, the antigenic composition, the antisera, the antibodies, the vector comprising the nucleic acid, and the transformed cell comprising the vector.

Methods and diagnostic kits for detecting *Chlamydia* or anti-*Chlamydia* antibodies in a test sample are also included, wherein the methods comprise the steps of:

a) contacting said sample with an antigenic composition comprising *Chlamydia* HMW protein or a fragment or analogue thereof or immunogenic composition or antibodies thereto to form *Chlamydia* antigen: anti-*Chlamydia* antibody immunocomplexes, and further, b) detecting the presence of or measuring the amount of said immunocomplexes formed during step a) as an indication of the presence of said *Chlamydia* or anti-*Chlamydia* antibodies in the test sample.

The diagnostic kits for detecting *Chlamydia* or antibodies thereto comprises antibodies, or an antigenic or immunogenic composition comprising *Chlamydia* HMW protein or a fragment or analogue thereof, a container means for contacting said antibodies or composition with a test sample suspected of having anti-*Chlamydia* antibodies or *Chlamydia* and reagent means for detecting or measuring *Chlamydia* antigen: anti-*Chlamydia* antibody immunocomplexes formed between said antigenic or immunogenic composition or said antibodies and said test sample.

A further aspect of the present invention provides methods for determining the presence of nucleic acids encoding a HMW protein or a fragment or analogue thereof in a test sample, comprising the steps of:

a) contacting the test sample with the nucleic acid molecule provided herein to produce duplexes comprising the nucleic acid molecule and any said nucleic acid molecule encoding the HMW protein in the test sample and specifically hybridizable therewith; and b) determining the production of duplexes.

The present invention also provides a diagnostic kit and reagents therefor, for determining the presence of nucleic acid encoding a HMW protein or fragment or analogue thereof in a sample, comprising:

a) the nucleic acid molecule as provided herein;

b) means for contacting the nucleic acid with the test sample to produce duplexes comprising the nucleic acid molecule and any said nucleic acid molecule encoding the HMW protein in the test sample and specifically hybridizable therewith; and c) means for determining the production of duplexes.

Also included in this invention are methods of preventing, treating or ameliorating disorders related to *Chlamydia* in an animal including mammals and birds in need of such treatment comprising administering and effective amount of the pharmaceutical or vaccine composition of the invention. Preferred disorders include a *Chlamydia* bacterial infection, trachoma, conjunctivitis, urethritis, lymphogranuloma venereum (LGV), cervicitis, epididymitis, or endometritis, pelvic inflammatory disease (PID), salpingitis, tubal occlusion, infertility, cervical cancer, and artherosclerosis. Preferred vaccine or pharmaceutical compositions include those formulated for in vivo administration to a host to confer protection against disease or treatment therefor caused by a species of *Chlamydia*. Also preferred are compositions formulated as a microparticle, capsule, liposome preparation or emulsion.

4. ABBREVIATIONS

| | |
|---|---|
| anti-HMW = | HMW polypeptide antibody or antiserum |
| ATCC = | American Type Culture Collection |
| immuno-reactive = | capable of provoking a cellular or humoral immune response |
| kDa = | kilodaltons |
| OG = | n-octyl β-D-glucopyranoside or octyl glucoside |
| OMP = | outer membrane protein |
| OMPs = | outer membrane proteins |
| PBS = | phosphate buffered saline |
| PAGE = | polyacrylamide gel electrophoresis |
| polypeptide = | a peptide of any length, preferably one having ten or more amino acid residues |
| SDS = | sodium dodecylsulfate |
| SDS-PAGE = | sodium dodecylsulfate polyacrylamide gel electrophoresis |

Nucleotide or nucleic acid sequence defined herein are represented by one-letter symbols for the bases as follows:
A (adenine)
C (cytosine)
G (guanine)
T (thymine)
U (uracil)
M (A or C)
R (A or G)
W (A or T/U)
S (C or G)
Y (C or T/U)
K (G or T/U)
V (A or C or G; not T/U)
H (A or C or T/U; not G)
D (A or G or T/U; not C)
B (C or G or T/U; not A)
N (A or C or G or T/U) or (unknown)

Peptide and polypeptide sequences defined herein are represented by one-letter symbols for amino acid residues as follows:
A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)
X (unknown)

The present invention may be more fully understood by reference to the following detailed description of the invention, non-limiting examples of specific embodiments of the invention and the appended figures.

5. BRIEF DESCRIPTION OF THE FIGURES

FIG. 1: Western blot analysis of *C. trachomatis* $L_2$ elementary bodies (EBs). Gradient purified EBs were solubilized in standard Laemmli SDS-PAGE sample buffer containing 2-mercaptoethanol, boiled for ~3 minutes and loaded onto a 4–12% Tris-glycine gradient gel containing SDS and electrophoresed at 100V. Immediately following electrophoresis, proteins were electroblotted onto PVDF membranes at 4° C. for ~2.5 hours at ~50V. The blocked membrane was probed using a $\frac{1}{5,000}$ dilution of anti-rHMWP' antibody (K196) for 1.5 hours at room temperature. Following washing, the membrane was treated with a $\frac{1}{5,000}$ dilution of a goat anti-rabbit IgG antibody conjugated to HRP for 1 hour at room temperature. The blot was developed using a standard TMB substrate system. Three immunoreactive bands detected in EBs and RBs. Dot indicates HMW Protein of about 105–115 kDa.

FIG. 2. Consensus Nucleic Acid Sequence encoding the open reading frame of the HMW protein from *C. trachomatis* LGV $L_2$ (SEQ ID NO.:1).

FIG. 3. Deduced Amino Acid Sequence of the HMW protein from the PCR open reading frame from *C. trachomatis* LGV $L_2$ (SEQ ID NO.:2).

Figure 4:
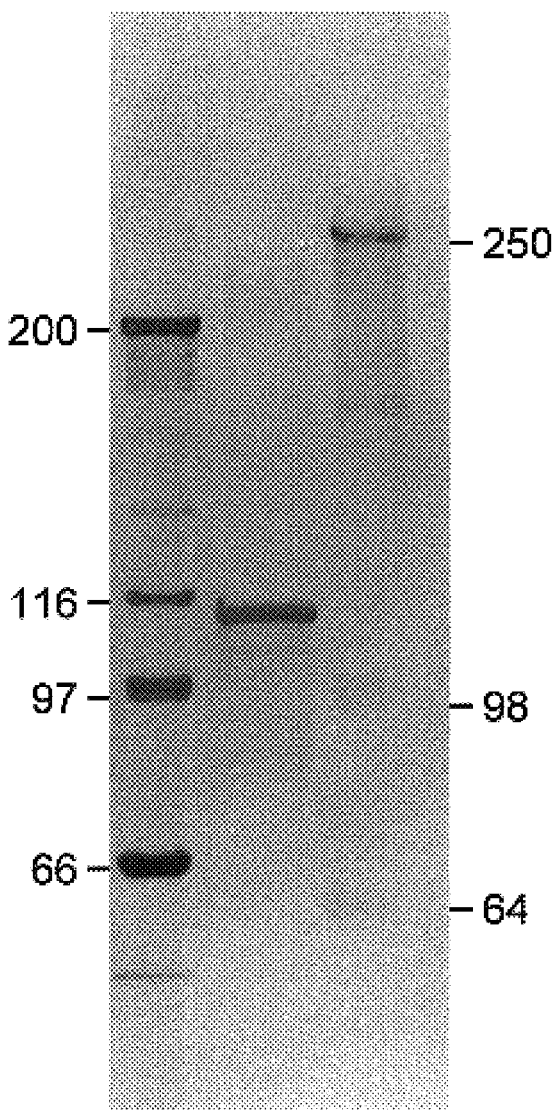

FIG. 4. SDS-PAGE of partially purified recombinant HMW protein from *C. trachomatis* LGV$L_2$ expressed in *E. coli*. Counterstained and prestained SDS-PAGE standards were used as molecular weight markers. The positions of the molecular weight markers in the gel are noted on the left and right side of the figure by lines to the molecular weights (kDa) of some of the markers. See Text Example 10 for details. Lane A: Mark 12 Wide Range Molecular Weight Markers (Novex); myosin, 200 Kdal; B-galactosidase, 116.3 Kdal; phosphorylase B, 97.4 Kdal; bovine serum albumin, 66.3 Kdal. Lane B: *C. trachomatis* L2 recombinant HMWP. Lane C: SeeBlue Prestained Molecular Weight markers (Novex); myosin, 250 Kdal; bovine serum albumin, 98 Kdal; glutamic dehydrogenase, 64 Kdal.

Figure 5:
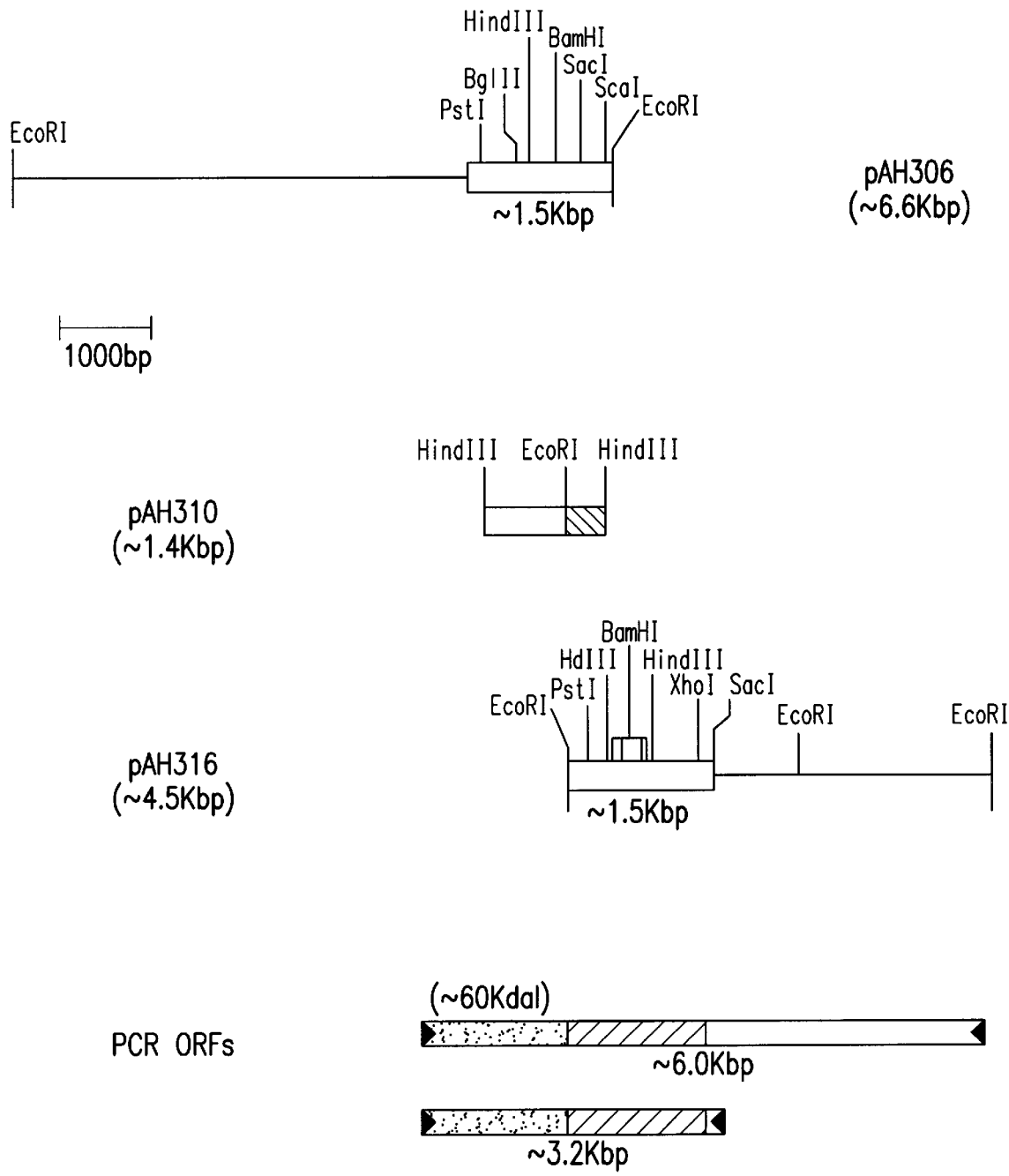

FIG. 5. Map of plasmids pAH306, pAH310, pAH312, pAH316 and the PCR open reading frame.

FIG. 6. Predicted amino acid sequences, of HMW protein for *C. trachomatis* $L_2$, B and F. The *C. trachomatis* $L_2$ sequence (SEQ ID NO.:43) is given in the top line and begins with the first residue of the mature protein, E (see amino acid residues 29-1012 of SEQ ID NO.:2). Potential eucaryotic N-glycosylation sequences are underlined. A hydrophobic helical region flanked by prolinerich segments and of suitable length to span the lipid bilayer is underlined and enclosed in brackets. Amino acid differences identified in the B (see amino acid residues 29-1013 of SEQ ID NO.:15) and F (see amino acid residues 29-1013 of SEQ ID NO.;16) serovars are designated below the $L_2$ HMWP protein sequence.

Figure 7A:
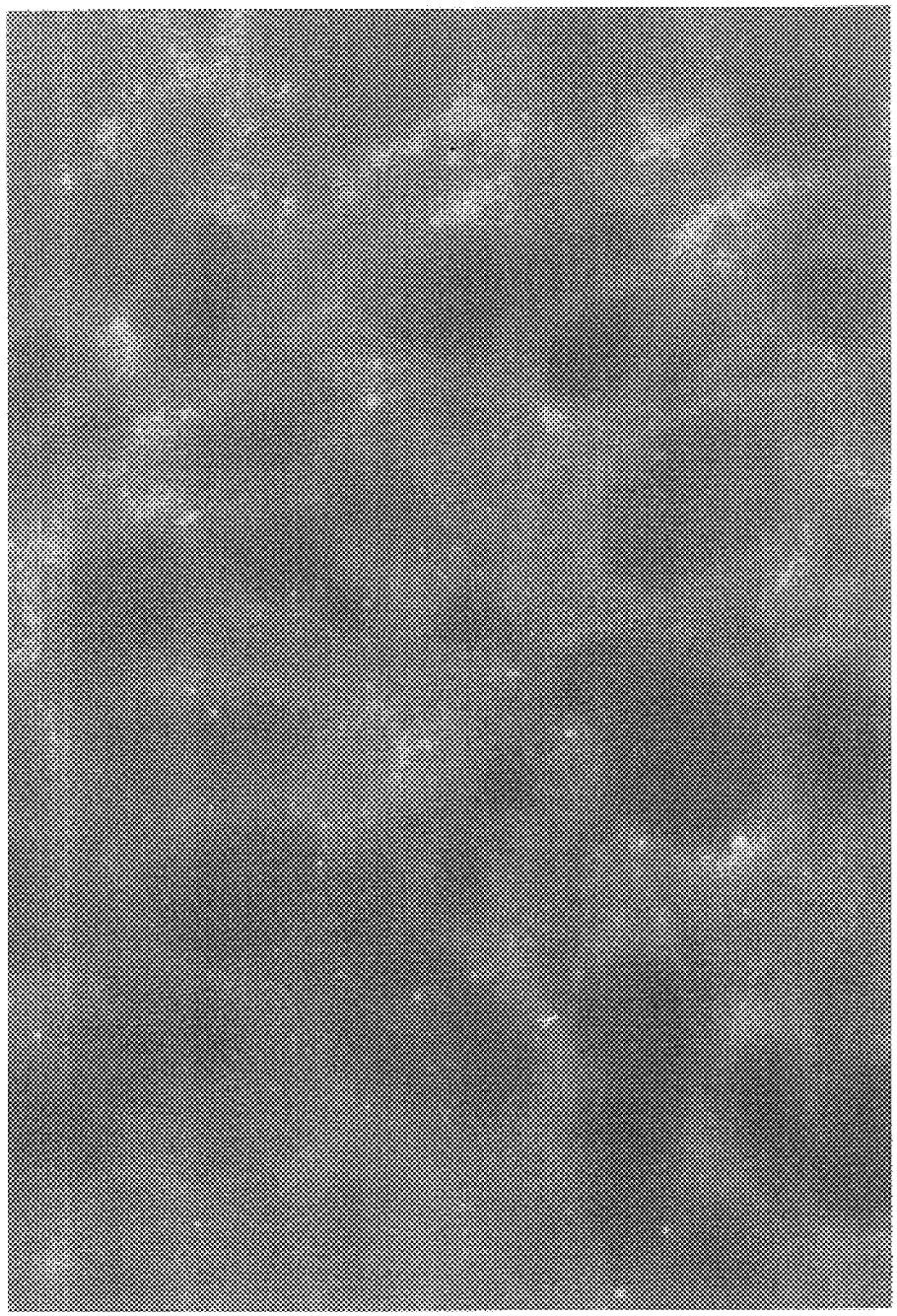
Figure 7B:
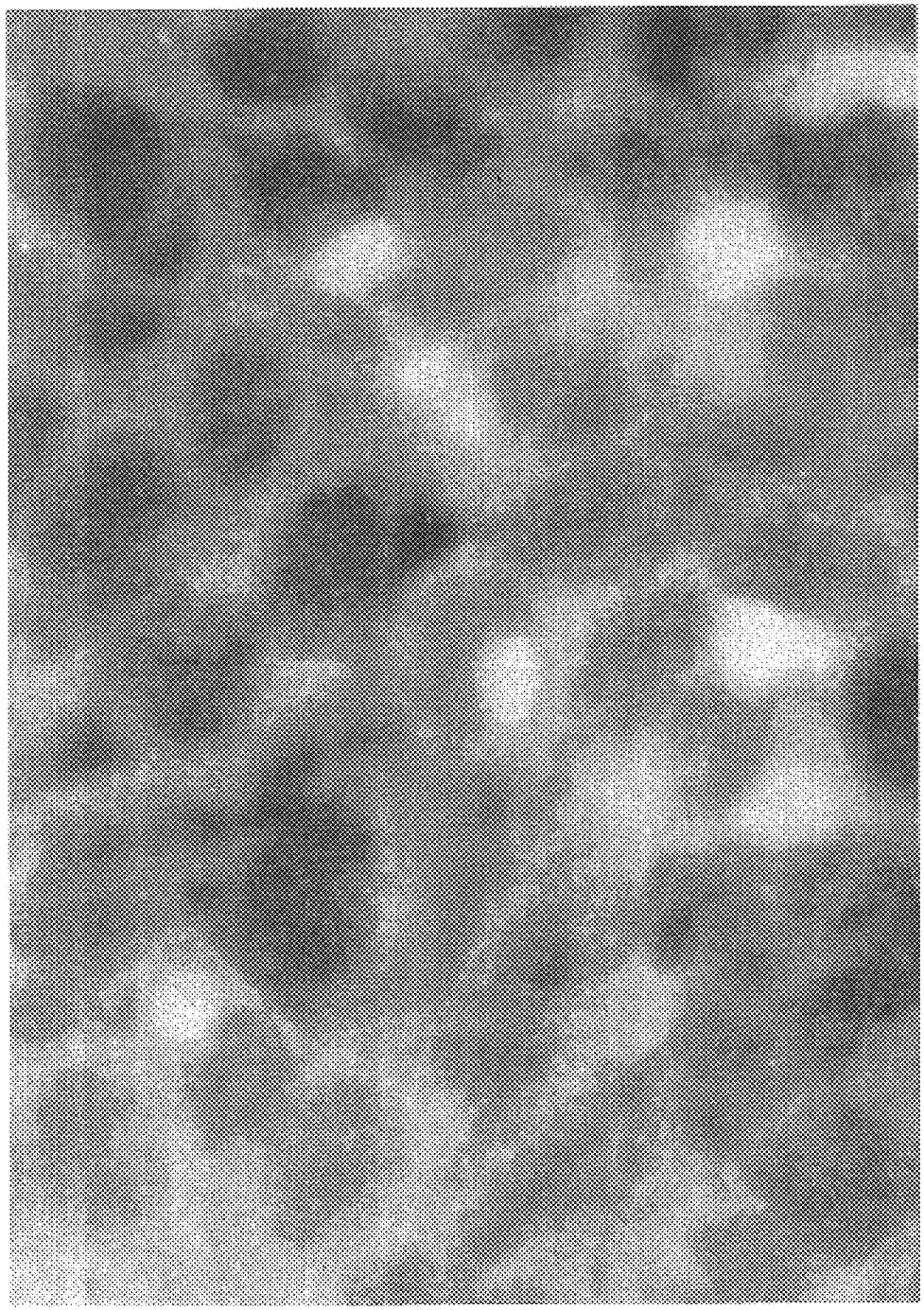

FIGS. 7A and B. Indirect florescence antibody staining of *C. trachomatis* N11 (serovar F) inclusion bodies using anti-rHMWP' antibody. Panel A: Post-immunization sera from rabbit K196. *Chlamydia* inclusion bodies are stained. Panel B: Pre-immunization sera from rabbit K196.

6. DETAILED DESCRIPTION OF THE INVENTION

The term "antigens" and its related term "antigenic" as herein and in the claims refers to a substance that binds specifically to an antibody or T-cell receptor. Preferably said antigens are immunogenic.

The term "immunogenic" as used herein and in the claims refers to the ability to induce an immune response, e.g., an antibody and/or a cellular immune response in a an animal, preferably a mammal or a bird.

The term "host" as used herein and in the claims refers to either in vivo in an animal or in vitro in mammalian cell cultures.

An effective amount of the antigenic, immunogenic, pharmaceutical, including, but not limited to vaccine, composition of the invention should be administered, in which "effective amount" is defined as an amount that is sufficient to produce a desired prophylactic, therapeutic or ameliorative response in a subject, including but not limited to an immune response. The amount needed will vary depending upon the immunogenicity of the HMW protein, fragment, nucleic acid or derivative used, and the species and weight of the subject to be administered, but may be ascertained using standard techniques. The composition elicits an immune response in a subject which produces antibodies, including anti-HMW protein antibodies and antibodies that are opsonizing or bactericidal. In preferred, non-limiting embodiments of the invention, an effective amount of a composition of the invention produces an elevation of antibody titer to at least three times the antibody titer prior to administration. In a preferred, specific, non-limiting embodiment of the invention, approximately 0.01 to 2000 µg and preferably 0.1 to 500 µg are administered to a host. Preferred are compositions additionally comprising an adjuvant.

Immunogenic, antigenic, pharmaceutical and vaccine compositions may be prepared as injectables, as liquid solutions or emulsions. The HMW protein may be mixed with one or more pharmaceutically acceptable excipient which is compatible with the HMW protein. Such excipients may include, water, saline, dextrose, glycerol, ethanol, and combinations thereof.

Immunogenic, antigenic, pharmaceutical and vaccine compositions may further contain one or more auxiliary substance, such as wetting or emulsifying agents, pH buffering agents, or adjuvants to enhance the effectiveness thereof. Immunogenic, antigenic, pharmaceutical and vaccine compositions may be administered parenterally, by injection, subcutaneously or intramuscularly.

Alternatively, the immunogenic, antigenic, pharmaceutical and vaccine compositions formed according to the present invention, may be formulated and delivered in a manner to evoke an immune response at mucosal surfaces. Thus, the immunogenic, antigenic, pharmaceutical and vaccine compositions may be administered to mucosal surfaces by, for example, the nasal, oral (intragastric), ocular, branchiolar, intravaginal or intrarectal routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 0.001 to 95% of the HMW protein. The immunogenic, antigenic, pharmaceutical and vaccine compositions are administered in a manner compatible with the dosage formulation, and in such amount as will be therapeutically effective, protective or immunogenic.

Further, the immunogenic, antigenic, pharmaceutical and vaccine compositions may be used in combination with or conjugated to one or more targeting molecules for delivery to specific cells of the immune system, such as the mucosal surface. Some examples include but are not limited to vitamin B12, bacterial toxins or fragments thereof, monoclonal antibodies and other specific targeting lipids, proteins, nucleic acids or carbohydrates.

The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of 0.1 to 1000 micrograms of the HMW protein, fragment or analogue thereof. Suitable regimes for initial administration and booster doses are also variable, but may include an initial administration followed by subsequent administrations. The dose may also depend on the route(s) of administration and will vary according to the size of the host.

The concentration of the HMW protein in an antigenic, immunogenic or pharmaceutical composition according to the invention is in general about 0.001 to 95%. A vaccine which contains antigenic material of only one pathogen is a monovalent vaccine. Vaccines which contain antigenic material of several pathogens are combined vaccines and also belong to the present invention. Such combined vaccines contain, for example, material for various pathogens or from various strains of the same pathogen, or from combinations of various pathogens.

The antigenic, immunogenic or pharmaceutical preparations, including vaccines, may comprise as the immunostimulating material a nucleotide vector comprising at least a portion of the gene encoding the HMW protein, or the at least a portion of the gene may be used directly for immunization.

To efficiently induce humoral immune responses (HIR) and cell-mediated immunity (CMI), immunogens are typically emulsified in adjuvants. Immunogenicity can be significantly improved if the immunogen is co-administered with an adjuvant. Adjuvants may be act by retaining the immunogen locally near the site of administration to produce a depot effect facilitating a slow, sustained release of antigen to cells of the immune system. Adjuvants can also attract cells of the immune system to an immunogen depot and stimulate such cells to elicit immune responses.

Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit either CMI or HIR or both to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically noncovalently linked to antigens and are formulated to enhance the host immune responses. Thus, adjuvants have been identified that enhance the immune response to antigens delivered parenterally. Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum.

Other extrinsic adjuvants may include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. International Patent Application, PCT/US95/09005 incorporated herein by reference describes mutated forms of heat labile toxin of enterotoxigenic E. coli ("mLT"). U.S. Pat. No. 5,057,540, incorporated herein by reference, describes the adjuvant, Qs21, and HPLC purified non-toxic fraction of a saponin from the bark of the South American tree Quiliaja saponanria molina 3D-MPL is described in great Britain Patent 2,220,211, and is incorporated herein by reference.

U.S. Pat. No. 4,855,283 granted to Lockhoff et al on Aug. 8, 1989 which is incorporated herein by reference, teaches glycolipid analogues including N-glycosylamides, N-glycosylureas and N-glycosylcarbamates, each of which is substituted in the sugar residue by an amino acid, as immuno-modulators or adjuvants. Lockhoff reported that N-glycosphospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Lipidation of synthetic peptides has also been used to increase their immunogenicity.

Therefore, according to the invention, the immunogenic, antigenic, pharmaceutical, including vaccine, compositions comprising a HMW protein, or a fragment or derivative thereof or a HMW encoding nucleic acid or fragment thereof or vector expressing the same, may further comprise an adjuvant, such as, but not limited to alum, mLT, QS21 and all those listed above. Preferably, the adjuvant is selected from alum, LT, 3D-mPL, or Bacille Calmette-Guerine (BCG) and mutated or modified forms of the above, particularly mLT and LTR192G. The compositions of the present invention may also further comprise a suitable pharmaceutical carrier, including but not limited to saline, bicarbonate, dextrose or other aqueous solution. Other suitable pharmaceutical carriers are described in *Remington's Pharmaceutical Sciences,* Mack Publishing Company, a standard reference text in this field, which is incorporated herein by reference in its entirety.

Immunogenic, antigenic and pharmaceutical, including vaccine, compositions may be administered in a suitable, nontoxic pharmaceutical carrier, may be comprised in microcapsules, and/or may be comprised in a sustained release implant.

Immunogenic, antigenic and pharmaceutical, including vaccine, compositions may desirably be administered at several intervals in order to sustain antibody levels, and/or may be used in conjunction with other bacteriocidal or bacteriostatic methods.

As used herein and in the claims, "antibodies" of the invention may be obtained by any conventional methods known to those skilled in the art, such as but not limited to the methods described in *Antibodies A Laboratory Manual* (E. Harlow, D. Lane, Cold Spring Harbor Laboratory Press, 1989) which is incorporated herein by reference in its entirety. The term "antibodies" is intended to include all forms, such as but not limited to polyclonal, monoclonal, purified IgG, IgM, IgA and fragments thereof, including but not limited to fragments such as Fv, single chain Fv (scFv), F(ab')$_2$, Fab fragments (Harlow and Leon, 1988, Antibody, Cold Spring Harbor); single chain antibodies (U.S. Pat. No. 4,946,778) chimeric or humanized antibodies (Morrison et al., 1984, Proc. Nat'l Acad. Sci. USA 81:6851); Neuberger et al., 1984, Nature 81:6851) and complementary determining regions (CDR), (see Verhoeyen and Windust, in Molecular Immunology 2ed., by B. D. Hames and D. M. Glover, IRL Press, Oxford University Press, 1996, at pp. 283–325), etc.

In general, an animal (a wide range of vertebrate species can be used, the most common being mice, rats, guinea pig, bovine, pig, hamsters, sheep, birds and rabbits) is immunized with the HMW protein or nucleic acid sequence or immunogenic fragment or derivative thereof of the present invention in the absence or presence of an adjuvant or any agent that enhances the immunogen's effectiveness and boosted at regular intervals. The animal serum is assayed for the presence of desired antibody by any convenient method. The serum or blood of said animal can be used as the source of polyclonal antibodies.

For monoclonal antibodies, animals are treated as described above. When an acceptable antibody titre is detected, the animal is euthanized and the spleen is aseptically removed for fusion. The spleen cells are mixed with a specifically selected immortal myeloma cell line, and the mixture is then exposed to an agent, typically polyethylene glycol or the like, which promotes the fusion of cells. Under these circumstances fusion takes place in a random selection and a fused cell mixture together with unfused cells of each type is the resulting product. The myeloma cell lines that are used for fusion are specifically chosen such that, by the use of selection media, such as HAT: hypoxanthine, aminopterin, and thymidine, the only cells to persist in culture from the fusion mixture are those that are hybrids between cells derived from the immunized donor and the myeloma cells. After fusion, the cells are diluted and cultured in the selective media. The culture media is screened for the presence of antibody having desired specificity towards the chosen antigen. Those cultures containing the antibody of choice are cloned by limiting dilution until it can be adduced that the cell culture is single cell in origin.

Antigens, Immunogens and Immunoassays

The HMW protein or nucleic acid encoding same, and fragments thereof are useful as an antigen or immunogen for the generation of anti-HMW protein antibodies or as an antigen in immunoassays including enzyme-linked immunosorbent assays (ELISA), radioimmunoassays (RIA) and other non-enzyme linked antibody binding assays or procedures known in the art for the detection of anti-bacterial, anti-*Chlamydia,* and anti-HMW protein antibodies. In ELISA assays, the HMW protein is immobilized onto a selected surface, for example, a surface capable of binding proteins such as the wells of a polystyrene microtiter plate.

After washing to remove incompletely absorbed HMW protein, a nonspecific protein solution that is known to be antigenically neutral with regard to the test sample may be bound to the selected surface. This allows for blocking of nonspecific absorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of bovine gamma globulin (BGG) and/or phosphate buffered saline (PBS)/Tween. The sample is then allowed to incubate for from 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound HMW protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG.

To provide detecting means, the second antibody may have an associated activity such as an enzymatic activity that will generate, for example, a color development upon incubating with an appropriate chromogenic substrate. Detection may then be achieved by detecting color generation. Quantification may then be achieved by measuring the degree of color generation using, for example, a visible spectrophotometer and comparing to an appropriate standard. Any other detecting means known to those skilled in the art are included.

Another embodiment includes diagnostic kits comprising all of the essential reagents required to perform a desired immunoassay according to the present invention. The diagnostic kit may be presented in a commercially packaged form as a combination of one or more containers holding the necessary reagents. Such a kit may comprise HMW protein or nucleic acid encoding same or fragment thereof, a monoclonal or polyclonal antibody of the present invention in combination with several conventional kit components. Conventional kit components will be readily apparent to those skilled in the art and are disclosed in numerous publications, including *Antibodies A Laboratory Manual* (E. Harlow, D. Lane, Cold Spring Harbor Laboratory Press, 1989) which is incorporated herein by reference in its entirety. Conventional kit components may include such items as, for example, microtitre plates, buffers to maintain the pH of the assay mixture (such as, but not limited to Tris, HEPES, etc.), conjugated second antibodies, such as peroxidase conjugated anti-mouse IgG (or any anti-IgG to the animal from which the first antibody was derived) and the like, and other standard reagents.

Nucleic Acids and Uses Thereof

The nucleotide sequences of the present invention, including DNA and RNA and comprising a sequence encoding the HMW protein or a fragment or analogue thereof, may be synthesized using methods known in the art, such as using conventional chemical approaches or polymerase chain reaction (PRC) amplification using convenient pairs of oligonucleotide primers and ligase chain reaction using a battery of contiguous oligonucleotides. The sequences also allow for the identification and cloning of the HMW protein gene from any species of *Chlamydia*, for instance for screening chlamydial genomic libraries or expression libraries.

The nucleotide sequences encoding the HMW protein of the present invention are useful for their ability to selectively form duplex molecules with complementary stretches of other protein genes. Depending on the application, a variety of hybridization conditions may be employed to achieve varying sequence identities. In specific aspects, nucleic acids are provided which comprise a sequence complementary to at least 10, 15, 25, 50, 100, 200 or 250 nucleotides of the HMW protein gene (FIG. 2). In specific embodiments, nucleic acids which hybridize to an HMW protein nucleic acid (e.g. having sequence SEQ ID NO: 1, 23 or 24) under annealing conditions of low, moderate or high stringency conditions.

For a high degree of selectivity, relatively stringent conditions are used to form the duplexes, such as, by way of example and not limitation, low salt and/or high temperature conditions, such as provided by 0.02 M to 0.15 M NaCl at temperatures of between about 50° C. to 70° C. For some applications, less stringent hybridization conditions are required, by way of example and not limitation such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. By way of example and not limitation, in general, convenient hybridization temperatures in the presence of 50% formamide are: 42° C. for a probe which is 95 to 100% homologous to the target fragment, 37° C. for 90 to 95% homology and 32° C. for 70 to 90% homology.

Low, moderate and high stringency conditions are well known to those of skill in the art, and will vary predictably depending on the base composition and length of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y. which is incorporate herein, by reference.

In the preparation of genomic libraries, DNA fragments are generated, some of which will encode parts or the whole of *Chlamydia* HMW protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, bacmids and yeast artificial chromosome (YAC). (See, for example, Sambrook et al., 1989, *Molecular Cloning,* A Laboratory Manual, 2D Ed., Cold spring Harbor Laboratory Press, Cold Spring Harbor, N.Y.; Glover, D. M. (ed.), 1985, *DNA Cloning: A Practical Approach,* MRL Press, Ltd., Oxford, U.K. Vol. I, II.) The genomic library may be screened by nucleic acid hybridization to labeled probe (Benton and Davis, 1977, *Science* 196:180; Grunstein and Hogness, 1975, *Proc. Natl. Acad. Sci. U.S.A.* 72:3961).

The genomic libraries may be screened with labelled degenerate oligonucleotide probes corresponding to the amino acid sequence of any peptide of HMW protein using optimal approaches well known in the art. In particular embodiments, the screening probe is a degenerate oligonucleotide that corresponds to the sequence of SEQ ID NO: 4. In another embodiment, the screening probe may be a degenerate oligonucleotide that corresponds to the sequence of SEQ ID NO:5. In an additional embodiment, any one of the oligonucleotides of SEQ ID Nos: 6–9, 12–14 and 18–21 are used as the probe. In further embodiments, any one of the sequences of SEQ ID NOs: 1, 10–11, 22–24 or any fragments thereof, or any complement of the sequence or fragments may be used as the probe. Any probe used preferably is 15 nucleotides or longer.

Clones in libraries with insert DNA encoding the HMW protein or fragments thereof will hybridize to one or more of the degenerate oligonucleotide probes. Hybridization of such oligonucleotide probes to genomic libraries are carried out using methods known in the art. For example, hybridization with the two above-mentioned oligonucleotide probes may be carried out in 2X SSC, 1.0% SDS at 50° C. and washed using the same conditions.

In yet another aspect, clones of nucleotide sequences encoding a part or the entire HMW protein or HMW-derived polypeptides may also be obtained by screening *Chlamydia* expression libraries. For example, *Chlamydia* DNA or *Chlamydia* cDNA generated from RNA is isolated and random fragments are prepared and ligated into an expression vector (e.g., a bacteriophage, plasmid, phagemid or cosmid) such that the inserted sequence in the vector is capable of being expressed by the host cell into which the vector is then introduced. Various screening assays can then be used to select for the expressed HMW protein or HMW-derived polypeptides. In one embodiment, the various anti-HMW antibodies of the invention can be used to identify the desired clones using methods known in the art. See, for example, Harlow and Lane, 1988, *Antibodies: A Laboratory Manual,* Cold Spring Harbor Laboratory Press, Cold Spring Harbor, N.Y., Appendix IV. Clones or plaques from the library are brought into contact with the antibodies to identify those clones that bind.

In an embodiment, colonies or plaques containing DNA that encodes HMW protein or HMW-derived polypeptide could be detected using DYNA Beads according to Olsvick et al., 29th ICAAC, Houston, Tex. 1989, incorporated herein by reference. Anti-HMW antibodies are crosslinked to tosylated DYNA Beads M280, and these antibody-containing beads would then be used to adsorb to colonies or plaques expressing HMW protein or HMW-derived polypeptide. Colonies or plaques expressing HMW protein or HMW-derived polypeptide is identified as any of those that bind the beads.

Alternatively, the anti-HMW antibodies can be nonspecifically immobilized to a suitable support, such as silica or Celite™ resin. This material would then be used to adsorb to bacterial colonies expressing HMW protein or HMW-derived polypeptide as described in the preceding paragraph.

In another aspect, PCR amplification may be used to produce substantially pure DNA encoding a part of or the whole of HMW protein from *Chlamydia* genomic DNA. Oligonucleotide primers, degenerate or otherwise, corresponding to known HMW protein sequences can be used as primers. In particular embodiments, an oligonucleotide, degenerate or otherwise, encoding the peptide having an amino acid sequence of SEQ ID NO: 2, 3 or 15–17 or any portion thereof may be used as the 5' primer. For fragment examples, a 5' primer may be made from any one of the nucleotide sequences of SEQ ID NO: 4–7, 10, 12, 22–24 or any portion thereof. Nucleotide sequences, degenerate or otherwise, that are reverse complements of SEQ ID NO: 11, 13 or 14 may be used as the 3' primer.

PCR can be carried out, e.g., by use of a Perkin-Elmer Cetus thermal cycler and Taq polymerase (GENE Amp™). One can choose to synthesize several different degenerate primers, for use in the PCR reactions. It is also possible to vary the stringency of hybridization conditions used in priming the PCR reactions, to allow for greater or lesser degrees of nucleotide sequence similarity between the degenerate primers and the corresponding sequences in *Chlamydia* DNA. After successful amplification of a segment of the sequence encoding HMW protein, that segment may be molecularly cloned and sequenced, and utilized as a probe to isolate a complete genomic clone. This, in turn, will permit the determination of the gene's complete nucleotide sequence, the analysis of its expression, and the production of its protein product for functional analysis, as described infra.

In a clinical diagnostic embodiment, the nucleic acid sequences of the HMW protein genes of the present invention may be used in combination with an appropriate indicator means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing HMW protein gene sequences.

The nucleic acid sequences of the HMW protein genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, semen, urine, tears, mucus, bronchoalveolar lavage fluid) or even tissues, is absorbed or otherwise affixed to a selected matrix or surface. The fixed, single-stranded nucleic acid is then subjected to specific hybridization with selected probes comprising the nucleic acid sequences of the HMW protein encoding genes or fragments or analogues thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of *Chlamydia*. The selected probe may be at least 15 bp and may be in the range of about 30 to 90 bp.

Expression of the HMW protein Gene

Plasmid vectors containing replicon and control sequences which are derived from species compatible with the host cell may be used for the expression of the genes encoding the HMW protein or fragments thereof in expression systems. Expression vectors contain all the necessary elements for the transcription and translation of the inserted protein coding sequence. The vector ordinarily carries a replication site, as well as marking sequences which are capable of providing phenotype selection in transformed cells. For example, *E. coli* may be transformed using pBR322 which contains genes for ampicillin and tetracycline resistance cells. Other commercially available vectors are useful, including but not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx. The plasmids or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be matter of choice depending upon the desired results.

In accordance with this invention, it is preferred to make the HMW protein by recombinant methods, particularly when the naturally occurring HMW protein as isolated from a culture of a species of *Chlamydia* may include trace amounts of toxic materials or other contaminants. This problem can be avoided by using recombinantly produced HMW protein in heterologous systems which can be isolated from the host in a manner to minimize contaminants in the isolated material. Particularly desirable hosts for expression in this regard include Gram positive bacteria which do not have LPS and are, therefore endotoxin free. Such hosts include species of *Bacillus* and may be particularly useful for the production of non-pyrogenic rHMW protein, fragments or analogues thereof.

A variety of host-vector systems may be utilized to express the protein-coding sequence. These include but are not limited to mammalian cell systems infected with virus (e.g., vaccinia virus, adenovirus, etc.); insect cell systems infected with virus (e.g., baculorvirus); microorganisms such as yeast containing yeast vectors, or bacteria transformed with bacteriophage DNA, plasmid DNA, or cosmid DNA. Hosts that are appropriate for expression of the HMW protein genes, fragments, analogues or variants thereof, may include *E. coli, Bacillus* species, *Haemophilus,* fungi, yeast, such as *Saccharomyces pichia, Bordetella,* or the baculovirus expression system may be used. Preferably, the host cell is a bacterium, and most preferably the bacterium is *E. coli, B. subtilis* or *Salmonella.*

The expression elements of vectors vary in their strengths and specificities. Depending on the host-vector system utilized, any one of a number of suitable transcription and translation elements may be used. In a preferred embodiment, a chimeric protein comprising HMW protein or HMW-derived polypeptide sequence and a pre and/or pro sequence of the host cell is expressed. In other preferred embodiments, a chimeric protein comprising HMW protein or HMW-derived polypeptide sequence fused with, for example, an affinity purification peptide, is expressed. In further preferred embodiments, a chimeric protein comprising HMW protein or HMW-derived polypeptide sequence and a useful immunogenic peptide or protein is expressed. In preferred embodiments, HMW-derived protein expressed contains a sequence forming either an outer-surface epitope or the receptor-binding domain of native HMW protein.

Any method known in the art for inserting DNA fragments into a vector may be used to construct expression vectors containing a chimeric gene consisting of appropriate transcriptional/translation control signals and the protein coding sequences. These methods may include in vitro recombinant DNA and synthetic techniques and in vivo recombinants (genetic recombination). Expression of a nucleic acid sequence encoding HMW protein or HMW-derived polypeptide may be regulated by a second nucleic acid sequence so that the inserted sequence is expressed in a host transformed with the recombinant DNA molecule. For example, expression of the inserted sequence may be controlled by any promoter/enhancer element known in the art. Promoters which may be used to control expression of inserted sequences include, but are not limited to the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thymidine kinase promoter (Wagner et al., 1981, *Proc. Natl. Acad. Sci.* U.S.A. 78:1441–1445), the regulatory sequences of the metallothionein gene (Brinster et al., 1982, *Nature* 296:39–42) for expression in animal cells; the promoters of β-lactamase (Villa-Kamaroff et al., 1978, *Proc. Natl. Acad. Sci. U.S.A.* 75:3727–3731), tac (DeBoer et al., 1983, *Proc. Natl. Acad. Sci. U.S.A.* 80:21–25), $P_L$, or trc for expression in bacterial cells (see also "Useful proteins from recombinant bacteria" in Scientific American, 1980, 242:74–94); the nopaline synthetase promoter region or the cauliflower mosaic virus 35S RNA promoter (Gardner et al., 1981, *Nucl. Acids Res.* 9:2871), and the promoter of the photosynthetic enzyme ribulose biphosphate carboxylate (Herrera-Estrella et al., 1984, *Nature* 310:115–120) for expression implant cells; promoter elements from yeast or other fungi such as the Gal4 promoter, the ADC (alcohol dehydrogenase) promoter, PGK (phosphoglycerol kinase) promoter, alkaline phosphatase promoter.

Expression vectors containing HMW protein or HMW-derived polypeptide coding sequences can be identified by three general approaches: a) nucleic acid hybridization, (b) presence or absence of "marker" gene functions, and (c) expression of inserted sequences such as reactivity with anti-HMW antibody. In the first approach, the presence of a foreign gene inserted in an expression vector can be detected by nucleic acid hybridization using probes comprising sequences that are homologous to the inserted HMW protein or HMW-derived polypeptide coding sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the HMW protein or HMW-derived polypeptide coding sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of HMW protein or HMW-derived polypeptide in in vitro assay systems, e.g., binding to an HMW ligand or receptor, or binding with anti-HMW antibodies of the invention, or the ability of the host cell to hemagglutinate or the ability of the cell extract to interfere with hemagglutination by *Chlamydia*.

Once a particular recombinant DNA molecule is identified and isolated, several methods known in the art may be used to propagate it. Once a suitable host system and growth conditions are established, recombinant expression vectors can be propagated and prepared in quantity. As explained above, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain induces; thus, expression of the genetically engineered HMW protein or HMW-derived HMW may be controlled. Furthermore, different host cells have characteristic and specific mechanisms for the translational and post-translation processing and modification of proteins. Appropriate cell lines or host systems can be chosen to ensure the desired modification and processing of the foreign protein expressed.

The proteins, polypeptides, peptides, antibodies and nucleic acids of the invention are useful as reagents for clinical or medical diagnosis of *Chlamydia* infections and for scientific research on the properties of pathogenicity, virulence, and infectivity of *Chlamydia,* as well as host defense mechanisms. For example, DNA and RNA of the invention can be used as probes to identify the presence of *Chlamydia* in biological specimens by hybridization or PCR amplification. The DNA and RNA can also be used to identify other bacteria that might encode a polypeptide related to the *Chlamydia* HMW protein. The proteins of the invention may be used to prepare polyclonal and monoclonal antibodies that can be used to further purify compositions containing the proteins of the invention by affinity chromatography. The proteins can also be used in standard immunoassays to screen for the presence of antibodies to *Chlamydia* in a sample.

7. BIOLOGICAL DEPOSITS

Certain plasmids that contain portions of the gene having the open reading frame of the gene encoding the HMW protein of *Chlamydia* that are described and referred to herein have been deposited with the America Type Culture Collection (ATCC) located at 10801 University Boulevard, Manassas, Va. 20110-2209, U.S.A., pursuant to the Budapest Treaty and pursuant to 37 CFR 1.808 and prior to the filing of this application. The identifications of the respective portions of the genes present in these plasmids are shown below.

Samples of the deposited materials will become available to the public upon grant of a patent based upon this United States patent application. The invention described and claimed herein is not to be limited by the scope of the plasmids deposited, since the deposited embodiment is intended only as an illustration of the invention. Any equivalent or similar plasmids that encode similar or equivalent proteins or fragments or analogues thereof as described in this application are within the scope of the invention.

| Microorganism | ATCC Accession No. | Date Deposited |
|---|---|---|
| *E. coli* BL21 pAH342 | ATCC 98538 | Sep. 8, 1997 |
| *E. coli* TOP10 (pJJ 36-J) | ATCC PTA-3719 | Sep. 20, 2001 |
| *E. coli* TOP 10 (pJJ 701) | ATCC PTA-4123 | Mar. 6, 2002 |

8. EXAMPLES

The above disclosure generally describes the present invention. A more specific description is provided below in the following examples. The examples are described solely for the purpose of illustration and are not intended to limited the scope of the invention. Changes in form and substitution of equivalents are contemplated as circumstances suggest or render expedient. Although specific terms have been employed herein, such terms are intended in a descriptive sense and not for purposes of limitation.

Methods of molecular genetics, protein biochemistry and immunology used but not explicitly described in the disclosure and examples are amply reported in the scientific literature and are well within the ability of those skilled in the art.

8.1 Example 1

Isolation and Purification of Mature Chlamydia Proteins

McCoy cells were cultured either in standard 225 $cm^2$ tissue culture flasks or in Bellco spinner flasks (Cytodex microcarrier, Pharmacia) at 37° C. in 5% $CO_2$ using DMEM media supplemented with 10% Chlamydia-antibody free fetal bovine serum, glucose and nonessential amino acids. *C. trachomatis* $L_2$ elementary bodies (ATCC VR-902B) were prepared from lysates of infected McCoy cells. Basically, McCoy cells infected with *C. trachomatis* $L_2$ (LGV) were sonicated and cellular debris was removed by centrifugation. The supernatant containing chlamydial elementary bodies (EBs) was then centrifuged and the pellet containing EBs was resuspended in Hanks' balanced salts solution (HBSS). RNase/DNase solution was added and incubated at 37° C. for 1 hour with occasional mixing. The EB containing solution was layered onto a discontinuous density gradient (40%, 44% and 54%) of Angiovist 370 (mixture of diatrizoate melgumine and diatrizoate sodium, Berlex Laboratories, Wayne, N.J.) and ultracentrifuged for separation of the EBs on the gradient. After centrifugation the EBs were harvested from the gradient between the interface of the 44% and 54% Angiovist 370 layers. The EBs were washed in phosphate buffered saline and resuspended in HBSS.

Purified EBs were sequentially extracted with 0.1% OGP [high ionic strength] in HBSS to remove peripheral surface proteins and held on ice. The same EB preparation was then extracted with 1.0% OGP, 10 mM DTT, 1 mM PMSF, 10 mM EDTA, in a 50 mM Tris pH 7.4 buffer. Extracts were dialyzed (3500 MWCO) to remove detergent and other reagents and concentrated by lyophilization. Protein containing extracts were diluted in HBSS and passed over commercially available heparin-sepharose columns (HiTrap Col., Pharmacia). After samples were applied to the heparin column nonadhered proteins were removed by washing with excess HBSS. Bound proteins were batch eluted with PBS containing 2 M sodium chloride. Eluents were dialyzed extensively to remove salt and then lyophilized. The heparin-binding proteins were size fractionated by SDS-PAGE and visualized by silver staining or analyzed by Western blotting. Protein(s) of about 105–115 KDa present in moderate amounts were detected as shown in FIG. 1. The isoelectric point of the native HMW protein was determined to be about 5.95.

To obtain one N-terminal amino acid sequence, sufficient quantities of the HMW protein ($\geq 5$ μg) were electroblotted onto a PVDF membrane (Applied Biosystems), and stained with Coomassie blue. Immobilized HMW protein was released from the membrane and treated in situ with low levels of endopeptidase Lys-C, endopeptidase Arg-C and/or endopeptidase Glu-C to fragment the native protein. The resulting peptide fragments were purified by HPLC and their N-terminal amino acid sequences determined using an ABI 430 Protein Sequenator and standard protein sequencing methodologies. The N-terminal amino acid sequence is:

E-I-M-V-P-Q-G-I-Y-D-G-E-T-L-T-V-S-F-X-Y and is denoted SEQ ID No.: 3.

When a composite PDB+SwissProt+PIR+GenPept database (>145 K unique sequences) was searched with the HMW protein N-terminal sequence (20 residues) using rigorous match parameters, no precise homologies were found. Thus the HMW protein is a novel chlamydial protein. Since this protein was isolated under conditions that should release only peripheral membrane proteins (e.g. Omp2), these data indicate that the HMW protein is a surface-associated protein.

8.2. Example 2

Preparation of Antibodies to Whole Chlamydia EBs

To aid in the characterization of the HMW protein, hyperimmune rabbit antisera was raised against whole EBs from *C. trachomatis* $L_2$. Each animal was given a total of three immunizations of about 250 μg of Chlamydia EBs per injection (beginning with complete Freund's adjuvant and followed with incomplete Freund's adjuvant) at approximately 21 day intervals. At each immunization, approximately half of the material was administered intramuscularly (i.m.) and half was injected intranodally. Fourteen days after the third vaccination a fourth booster of about 100 μg of EBs was given i.m. and the animals exsanguinated 7–10 days later. A titre of 1:100,000 was obtained as determined by ELISA.

8.3. Example 3

Determination of Post-Translational Modifications

Recently, several *C. trachomatis* membrane-associated proteins have been shown to be post-translationally modified. The 18 kDa and 32 kDa cysteine-rich EB proteins, which are lectin-binding proteins, have been shown to carry specific carbohydrate moieties (Swanson, A. F. and C. C. Kuo. 1990. *Infect. Immun.* 58:502–507). Incorporation of radiolabelled palmitic acid has been used to demonstrate that the about 27 kDa *C. trachomatis* Mip-like protein is lipidated (Lundemose, A. G., D. A. Rouch, C. W. Penn, and J. H. Pearce. 1993. *J. Bacteriol.* 175:3669–3671). Swanson et al. have discovered that the MOMP from the $L_2$ serovar contains N-acetylglucosamine and/or N-acetylgalactosamine and these carbohydrate moieties mediate binding of MOMP to Hela cell membranes.

To ascertain whether the HMW protein is glycosylated, EBs are grown on McCoy cells in the presence of tritiated galactose or glucosamine, subjected to heparin affinity chromatography and the heparin binding proteins analyzed by SDS-PAGE and autoradiography. Briefly, McCoy cells are grown in T225 flasks under standard conditions (DMEM+ 10% FCS, 35 ml per flask, 10% $CO_2$) to about 90% confluency and inoculated with sufficient EBs to achieve 90%–100% infectivity. Following a 3 hour infection period at 37° C. cycloheximide is added (1 μg/ml) to inhibit host cell protein synthesis and the cultures reincubated for an additional 4–6 hours. Approximately 0.5 mCi of tritiated galactose (D-[4,5-$^3$H(N)]galactose, NEN) or glucosamine (D-[1,6-$^3$H(N)glucosamine, NEN) is then be added to each flask and the cultures allowed to incubate for an additional 30–40 hours. Cells are harvested by scraping and EBs purified by gradient centrifugation. HMW protein is isolated from 1.0% OGP surface extracts by affinity chromatography, eluted with NaCl and analyzed by SDS-PAGE using $^{14}$C-labelled molecular weight markers (BRL) then subjected to autoradiography. Dried gels are exposed for 1–4 weeks to Kodak X-AR film at −70° C.

To determine post synthesis lipid modification, *C. trachomatis* serovar $L_2$ is cultivated on monolayers of McCoy cells according to standard procedures. Approximately 24 hours postinfection, conventional culture media (DMEM+ 10% FCS) is removed and replaced with a serum-free medium containing cycloheximide (1 μg/ml) and [U-$^{14}$C] palmitic acid (0.5 mCi/T225 flask, NEN) and incubated for a further 16–24 hours to allow protein lipidation to occur. Surface EB extracts are prepared, heparin-binding proteins are isolated and analyzed by autoradiography as described above.

The functionality of glycosylated or lipidated moieties is assessed by treating whole EBs or OGP surface extracts with appropriate glycosidases. Following carbohydrate removal, extracts are subjected to affinity chromatography and SDS-PAGE to determine whether the HMW protein retains the ability to bind to heparin sulfate.

8.4. Example 4

Cloning of the N-terminal Segment of the HMW Protein Gene

Degenerate oligonucleotides were designed based on the N-terminal amino acid sequence of the HMW protein and were synthesized. These oligonucleotides were then used to generate gene-specific PCR products that were employed as hybridization probes to screen a *C. trachomatis* $L_2$ λZAPII DNA library to isolate the gene for the HMW protein.

Briefly, appropriate low degeneracy peptide segments were identified from the N-terminal and internal amino acid sequence data by computer analysis (MacVector, IBI) and used to guide the design of low degeneracy sequence-specific oligonucleotide PCR primer sets.

Using the N-terminal primary sequence as a guide, four degenerate oligonucleotide probes complementary to the nucleotides encoding the first six residues of the HMW peptide E-I-M-V-P-Q (SEQ ID NO.: 42 corresponding to residues 1–6 of SEQ ID NO.: 3), and comprising all possible nucleotide combinations (total degeneracy=192 individual sequences), have been designed and employed as forward amplification primers.

SEQ ID No.4 5'-GAA-ATH-ATG-GTN-CCN-CAA-3'.
SEQ ID No.5 5'-GAA-ATH-ATG-GTN-CCN-CAG-3'
SEQ ID No.6 5'-GAG-ATH-ATG-GTN-CCN-CAA-3'

SEQ ID No.7 5'-GAG-ATH-ATG-GTN-CCN-CAG-3'

Two additional oligonucleotide probes representing the reverse complement DNA sequence of the internal five residue peptide Y-D-G-E-T (residues 9–13 of SEQ ID No.: 3), and comprising all possible nucleotide combinations (total degeneracy=128 individual sequences), have been designed and employed as reverse amplification primers.

SEQ ID No.8 5'-NGT-YTC-NCC-RTC-ATA-3'

SEQ ID No.9 5'-NGT-YTC-NCC-RTC-GTA-3'

Oligonucleotides were synthesized on an ABI Model 380B DNA synthesizer using a 0.2 μmol scale column (tritylon, auto-cleavage) and standard phosphoramidite chemistry. Crude oligonucleotides were manually purified over C-18 syringe columns (OP Columns, ABI). Purity and yield were ascertained spectrophotometrically (230/260/280 ratios).

Standard PCR amplification reactions (2 mM $Mg^{2+}$, 200 umol dNTPs, 0.75 units AmpliTaq, 50 μl final volume) were programmed using about 0.2 μg C. trachomatis $L_2$ DNA (about $3 \times 10^7$ copies of the HMW protein gene if single copy) and about 100 pmol of each forward (N-terminal oligo) and reverse (internal oligo) primer. Higher than normal concentrations of primers (~20 pmol/50 μl) were used for amplification, at least initially, in order to compensate for primer degeneracy. Amplification of target sequences was achieved using a standard 30-cycle, three-step thermal profile, i.e. 95° C., 30 sec; 60° C., 45 sec, 72° C., 1 min. Amplification was carried out in sealed 50 μl glass capillary tubes using a Idaho Technologies thermal cycler. To verify that the PCR products generated during these amplification reactions were specific for the HMW protein coding sequence and were not "primer-dimer" or other DNA amplification artifacts, amplimers were purified using silica-gel spin columns (QIAGEN), cloned into the PCR cloning vector pZERO (StrataGene), and subjected to direct DNA sequence analysis.

The DNA sequence for the cloned PCR products were determined using conventional dideoxy-terminator sequencing chemistry and a modified T7 DNA polymerase (Sequenase, USB). Briefly, each double stranded plasmid template was denatured by a brief treatment with NaOH. Following neutralization, each denatured template was used to program 4 separate sequencing reactions. Each reaction contained the M13 universal forward sequencing primer (21-mer) but a different ddNTP/dNTP termination mix (i.e. A,G,C, or T). Termination products were labelled by including [α-$^{35}$S]dATP in the reaction (~50 uCi/reaction, >3000 Ci/mmol, Amersham). Individual extension products were denatured (formamide, ~95° C.) and subjected to high resolution denaturing polyacrylamide gel electrophoresis (6% acrylamide, 8M urea, TAE buffer, ~500 V, ~90 min). Sequencing gels were then transferred to filter paper (Whatmann 3MM), dried under vacuum, and then autoradiographed at −70° C. for 24–72 hours. Base ladders were read manually from each gel and a consensus sequence determined.

HMW protein-specific amplimers suitable for library screening and/or Southern blotting were produced by PCR and uniformly radiolabelled during the amplification process by adding [α-$^{32}$P]dNTPs (about 50 μCi each dNTP, Amersham, >5000 Ci/mmol) to the reaction mixture. Labelling reactions were performed as above except reactions were performed in 0.5 ml microcentrifuge tubes using a Bellco Thermal Cycler. Unincorporated label and amplification primers were removed from the reaction mixture using centrifugal size-exclusion chromatography columns (BioSpin 6 columns, BioRad).

A highly redundant *C. trachomatis* serovar $L_2$ DNA library (>50,000 primary clones) has been constructed by cloning size-fractionated fragments ≧10 Kbp produced from a partial EcoRI digest of genomic DNA into the lambda cloning vector λZAPII (Stratagene). Radiolabelled HMW protein-specific PCR products were used to screen this library for recombinant clones that carry all or part of the HMW protein coding sequence. Standard recombinant DNA procedures and methodologies were employed for these experiments. All phage that hybridized with these probes were purified to homogeneity by sequential rounds of plating and hybridization screening. Once reactive phage were purified, insert-containing phagmids (pBluescript SK-derivatives) were excision-rescued from the parental phage by coinfecting host cells with an appropriate helper phage, e.g. R408 or VCSM13 (Stratagene). Individual phagmids were further purified by streak-plating on LB agar containing ampicillin (100 μg/ml) and selecting for individual colonies.

To confirm purified phagemid derivatives carried the HMW protein sequences, plasmid DNA was prepared and used to program amplification reactions containing the HMW protein-specific PCR primer sets. The presence of HMW protein-specific inserts was confirmed by the production of the appropriate sized PCR product.

Plasmid pAH306 is one HMW protein-containing derivative that was isolated by these methodologies.

Physical Mapping of pAH306

The inserts from pAH306 were physically mapped and the location of HMW protein gene determined using appropriate six-base restriction endonucleases (e.g. EcoRI, HindIII, BamHI, PstI, SmaI, KpnI, etc.) and HMW protein coding sequences localized by Southern hybridization employing radiolabelled N-terminal-specific PCR products as probes. The orientation and extent of HMW protein-specific sequences were determined by PCR analysis using primer sets consisting of HMW protein-specific forward primers and reverse primers complementary to either the T3 or T7 promoter sequences located in the cloning vector.

Plasmid pAH306 was determined to contain a single ~6.6 Kbp EcoRI fragment of chlamydial origin. Directional PCR analysis of pAH306 demonstrated this derivative encodes roughly 1.5 Kbp of the N-terminal region of the HMW protein gene.

The DNA sequence for the HMW protein gene encoded on pAH306 was obtained for both strands via conventional "sequence-walking" coupled with asymmetric PCR cycle sequencing methodologies (ABI Prism Dye-Terminator Cycle Sequencing, Perkin-Elmer). Sequencing reactions were programmed with undigested plasmid DNA (~0.5 μg/rxn) as a template and appropriate HMW protein-specific sequencing primers (~3.5 pmol/rxn).

In addition to the template and sequencing primer, each sequencing reaction (~20 μl) contained the four different dNTPs (i.e. A,G,C, and T) and the four corresponding ddNTPs (i.e. ddA, ddG, ddC, and ddT) terminator nucleotides; with each terminator being conjugated to one of four different fluorescent dyes. Single strand sequencing elongation products were terminated at random positions along the template by the incorporation of the dye-labelled ddNTP terminators. Fluorescent dye-labelled termination products were purified using microcentrifuge size-exclusion chromatography columns (Princeton Genetics), dried under vacuum, suspended in a Template Resuspension Buffer (Perkin-Elmer), denatured at 95° C. for ~5 min, and resolved by high resolution capillary electrophoresis on an ABI 310 Automated DNA Sequenator (Perkin-Elmer).

DNA sequence data produced from individual reactions were collected and the relative fluorescent peak intensities analyzed automatically on a PowerMAC computer using ABI Sequence Analysis Software (Perkin-Elmer). Individually autoanalyzed DNA sequences were edited manually for accuracy before being merged into a consensus sequence "string" using AutoAssembler software (Perkin-Elmer). Both strands of the HMW protein gene segment encoded by pAH306 were sequenced and these data compiled to create a composite sequence for the HMW protein gene segment. The sequence encoding the segment of HMW protein is listed as SEQ ID NO.: 10 and is represented by nucleotides 466 to 1976 in FIG. 2. A map of pAH306 is shown in FIG. 5.

Database analysis (e.g. primary amino acid homologies, hydropathy profiles, N-/O-glycosylation sites, functional/conformational domain analyses) of the DNA and predicted amino acid sequences for the HMW protein was performed using GeneRunner and Intelligentics software, indicating the HMW protein is novel.

8.5. Example 5

Cloning of the C-terminal Segment of the HMW Protein Gene

Chromosome walking was employed to isolate the C-terminal portion of the HMW protein gene. A ~0.6 Kbp BamHI-EcoRI fragment distal to the N-terminal sequence of the mature HMW protein and proximal to the T3 promoter sequence of the vector was chosen as the probe for the initial chromosome walk. Briefly, pAH306 was digested to completion with BamHI and EcoRI and the digestion products size fractionated by agarose gel electrophoresis (0.8% agarose in TAE buffer). The desired ~0.6 Kbp BamHI/EcoRI (B/E) band was excised from the gel and purified using commercially available silica gel microcentrifuge chromatography columns and reagents (QIAGEN).

The purified 0.6 Kbp B/E fragment was radiolabelled with [α-dATP] (>3000 Ci/mmol, Amersham) via random-priming labelling methodologies employing commercially available reagents (Boehringer Mannheim) and used to probe Southern blots of C. trachomatis $L_2$ genomic DNA that had been digested to completion with HindIII.

The 0.6 Kbp B/E probe from pAH306 hybridized to a ~1.4 Kbp HindIII genomic fragment. Based on the experimentally derived restriction map of the HMW protein gene segment encoded on pAH306, this fragment encodes ~0.2 Kbp of the C-terminal HMW protein sequence.

The radiolabelled 0.6 Kbp B/E fragment was used subsequently to probe a moderately redundant (~5,000 primary clones) C. trachomatis L2 library to identify clones that contain the ~1.4 Kbp HindIII fragment. Briefly, *C. trachomatis* $L_2$ genomic DNA was digested to completion using a ~10-fold excess of the restriction endonuclease HindIII (~10 units per 1 μg of genomic DNA, 37° C., 18–24 hours). Digestion products were size fractionated by agarose gel electrophoresis (0.8% agarose, TAE) and DNA fragments ranging in size from ~1.0 Kbp to 2.0 Kbp were excised from the gel. Excised agarose strips contain the desired DNA fragment sizes were dissolved in a solubilization/binding solution (QX1,QIAGEN) and purified using commercially available silica-gel spin columns (QIAGEN). Purified 1.0–2.0 Kbp genomic HindIII fragments were then cloned into the pBlueScript SK-plasmid which had been previously digested to completion with HindIII and treated with calf intestinal phosphatase to prevent vector religation.

Vector/insert ligations were performed in a ~50 μl final reaction volume (50 mM Tris-HCl, pH 7.00; 10 mM NaCl; 1 mM ATP; 0.5 mM DTT) at 25° C. for ~15–24 hours using T4 DNA ligase (~10 units/reaction) and a vector:insert molar ratio of approximately 1:10. Following ligation, aliquots (~50 ng ligated DNA) were used to electroporate a competent *E. coli* host, e.g. *E. coli* TOP10. Electroporated cells were then plated onto LB agar containing ~100 μg/ml ampicillin to select for plasmid-harboring clones. Approximately 1,000 plasmid-harboring $Ap^R$ transformants were transferred directly from LB $Ap^{100}$ agar plates onto nylon membranes (HyBond N+, Amersham) by capillary action.

Following transfer, plates were re-incubated at 37° C. to regenerate viable colonies for further manipulation. Colonies transferred to membranes were lysed and DNA liberated by treating the colony blots with a denaturing SDS/NaOH solution. A Tris buffered NaCl solution was used to neutralize and stabilize lysis material. Released DNA was immobilized onto the membrane by UV irradiation. Standard recombinant DNA procedures and methodologies were employed to probe the colony blots with the radiolabelled 0.6 Kbp B/E fragment and identify recombinant derivatives which carry the desired ~1.4 Kbp HindIII fragment.

Plasmid pAH310 was one derivative isolated by these procedures and the coding segment of the HMW protein is represented by nucleotides 994–2401 in FIG. 2.

Restriction analysis using HindIII and EcoRI, individually and in combination, together with DNA sequence analysis of purified plasmid DNA confirmed pAH310 encodes the expected ~1.4 Kbp HindIII fragment. These analyses also demonstrated that the ~1.4 Kbp insert consists of the same ~1.2 Kbp HindIII-EcoRI fragment that is present in pAH306 and a unique ~0.2 Kbp EcoRI-HindIII fragment that encodes C-terminal HMW protein-specific DNA.

The ~0.2 Kbp EcoRI-HindIII (E/H) fragment was chosen as the probe for the second chromosome walk. Briefly, pAH310 was digested to completion with EcoRI and HindIII and the digestion products size fractionated by agarose gel electrophoresis (0.8% agarose in TAE buffer). The desired ~0.2 Kbp (E/H) band was excised from the gel, purified, radiolabelled with [$\alpha$-$P^{32}$]dATP, and used as a probe to identify clones in the original *C. trachomatis* $L_2$ λZAPII genomic library that encode the C-terminal segment of the HMW protein gene.

Plasmid pAH316 is one derivative isolated by these procedures. Restriction analysis of pAH316 demonstrated that this derivative contains a *C. trachomatis* $L_2$ insert of ~4.5 Kbp which consists of two EcoRI fragments of ~2.5 Kbp and ~2.0 Kbp in size. Southern hybridization analysis using the ~0.2 Kbp E/H fragment as a probe localized this sequence to the ~2.5 Kbp EcoRI fragment of pAH316. Directional PCR analyses employing purified pAH316 plasmid DNA as a template and amplification primer sets specific for ~0.2 Kbp E/H fragment and T3 and T7 vector sequences demonstrated pAH316 encodes the C-terminal segment of the HMW protein gene. The coding segment of the HMW protein is represented by nucleotides 1977 to 3420 in FIG. 2, and is listed as SEQ ID NO.: 11.

8.6. Example 6

Production of Truncated HMW Recombinant Protein

The N-terminal half of the HMW protein was PCR cloned as a ~1.5 Kbp fragment into the commercially available *E. coli* expression plasmid pTrcHisB (Invitrogen). The forward primer used in these reactions was designated 140FXHO (57-mer), listed as SEQ ID No. 18, and contains sequences complementary to the first 10 N-terminal residues of the mature HMW protein. In addition to the HMW proteincoding sequences, this forward primer also carries a unique XhoI restriction site located optimally located upstream of the first residue of the mature HMW protein (Glu/E) for proper fusion to the $(His)_6$ affinity purification domain encoded on the vector plasmid, and 5' terminal 6 base G/C clamp for effective amplification and a 12 base internal spacer for effective endonuclease recognition and digestion.

SEQ ID No. 18 5'-AAG-GGC-CCA-ATT-ACG-CAG-AGC-TCG-AGA-GAA-ATT-ATG-GTT-CCT-CAA-GGA-ATT-TAC-GAT-3'

SEQ ID No. 19 5'-CGC-TCT-AGA-ACT-AGT-GGA-TC-3'

The commercially available reverse sequencing primer SK (20mer, StrataGene), SEQ ID No. 19, which is complementary to phagemid sequences downstream of the EcoRI site in pAH306, was used as the reverse amplification primer in these reactions. To obtain acceptable yields of the HMW protein ORF product (~1.5 Kbp), PCR amplification was performed using a mixture of thermostable DNA polymerases consisting of *T. thermophilus* DNA polymerase (Advantage Polymerase), as the primary amplification polymerase and a minor amount of a second high fidelity thermostable DNA polymerase to provide additional 5'-3' proofreading activity (CloneTech). An anti-Tth DNA polymerase antibody was added to the reaction mixture to provide automatic "hot-start" conditions which foster the production of large >2 Kbp amplimers. pAH306 plasmid DNA purified using a commercially available alkaline/SDS system (QIAGEN) and silica gel spin columns (QIAGEN) was used to program these amplification reactions (~0.2 ng/reaction).

The ~1.5 Kbp amplimer was purified from unincorporated primers using silica gel spin columns and digested to completion using an excess of XhoI and EcoRI (~10 units per 1 μg DNA). The purified and digested N-terminal truncated HMW protein ORF was then be cloned into the commercially available expression plasmid pTrcHisB that had been previously digested with both XhoI and EcoRI (5:1, insert:vector ratio). Aliquots from the ligation reaction were then be used to electrotransform a suitable *E. coli* host (e.g. TOP10).

Mini-prep DNA from ampicillin-resistant transformants picked at random were prepared, digested to completion with XhoI, EcoRI, or a combination of both and examined for the presence and orientation of the ~1.5 Kbp truncated HMW protein ORF insert by agarose gel electrophoresis. Mini-prep DNA from clones determined to carry the ~1.5 Kbp XhoI/EcoRI insert was prepared and used to program asymmetric PCR DNA sequencing reactions to confirm the fidelity of the junction formed between the HMW protein fragment and the $(His)_6$ affinity purification domain of the expression vector. Plasmid pJJ36-J was one recombinant derivative isolated by these procedures and is represented by nucleotides 466 to 1980 in FIG. 2. The deduced amino acid sequence of the truncated fragment of HMW protein is represented by amino acids 29 to 533 in FIG. 3 and is listed as SEQ ID NO.: 17.

8.7. Example 7

Determination of Presence in Other Species

Polymerase chain reaction analyses were undertaken to establish the presence of the HMW gene in several clinically recognized *C. trachomatis* strains and as well as other *chlamydial* species, e.g., *C. pneumoniae. Chlamydia trachomatis* strains as frozen stocks from the ATCC (Rockville, Md.) were used to infect subconfluent monolayers (about 80%) of McCoy cells according to standard procedures. Infected monolayers were either centrifuged in a Sorvall RT6000B centrifuge (~1,300 rpm, 25° C., 30 min) and/or treated with dextran sulfate (~50 $\mu$g/ml) at the time of infection to enhance initial attachment of the low infectivity biovars (non-LGV) to host cells and thus increase the final EB yield. Roughly 48 hours later, infected monolayers were collected by scraping and host cells disrupted by sonication to release elementary bodies (EBs). Total DNA was extracted from purified EBs (~$10^7$–$10^8$) of each strain using the proteinase K/Nonidet P40 method described by Denamur, et al., *J. Gen. Microbiol.* 137:2525–2530 (1991), incorporated herein by reference, and further purified by phenol/chloroform extraction and salt precipitation. Purified *Chlamydia pneumoniae* (AR-139) genomic DNA was purchased from Advanced Biotechnologies Inc.

To determine the presence of the HMW protein gene in these strains, amplification reactions were programmed using total Chlamydia DNA as template and the HMW protein segment-specific oligonucleotide primer (21mers) sets listed below.

SEQ ID No.20 5'-ATG-GTT-CCT-CAA-GGA-ATT-TAC-G-3'

SEQ ID No.21 5'-GGT-CCC-CCA-TCA-GCG-GGA-G-3'

Briefly, standard PCR amplification reactions (2 mM $Mg^{2+}$, 100 $\mu$mol dNTPs, 0.75 units AmpliTaq polymerase, 50 $\mu$l final volume) were programmed using approximately 15 $\mu$l of the crude *C. trachomatis* DNA extracts (~10 $\mu$l of the commercially available *C. pneumoniae* DNA) and ~20 pmol of each forward and reverse HMW protein-specific amplification primers of SEQ ID No. 20 and 21. Amplification of small target sequences (≦2 Kbp) was achieved using a 32-cycle, three-step thermal profile, i.e. 95° C., 30 sec; 60° C., 30 sec, 72° C., 1 min. Amplification of longer target sequences for ORF-cloning and sequencing was carried out using the crude DNA extracts in an identical fashion except that a MAb-inactivated Tth/Vent DNA polymerase enzyme combination was employed (Advantage PCR, Clontech) and a 72° C. extension time was used that matched the size of the desired PCR product plus 2 min (i.e. desired PCR product=6 Kbp, extension time=8 min).

Both conventional and long-distance PCRs were carried out using 0.2 ml thin-walled polypropylene microcentrifuge tubes in an ABI 2400 Thermal Cycler (Perkin-Elmer). Following thermal cycling, aliquots (~20 $\mu$l) of the reactions were analyzed and PCR products identified by standard agarose gel electrophoresis (0.8% agarose in TAE buffer) and ethidium bromide staining. The results showed that the HMW protein is highly conserved in clinically relevant serovars; the HMW gene was present in all Chlamydia samples strains tested, including serovars B, Ba, D, E, F, G, H, I, J, K, $L_1$, $L_2$ and MoPn and in *C. pneumoniae.*

8.8. Example 8

Determination of Sequence Variation

To establish the degree of DNA and amino acid sequence variation among different Chlamydia strains, the gene for the HMW protein was PCR-cloned from both a *C. trachomatis* B serovar (representing the trachoma group of organisms) and from a *C. trachomatis* F serovar (representing the low infectivity STD biovars) and compared to the HMW protein consensus *C. trachomatis* $L_2$ sequence.

Briefly, LD-PCR was used to generate ~6 Kbp HMW protein-specific DNA fragments from *C. trachomatis* B and F genomic DNA that contain the complete coding sequence for the mature HMW protein. Amplification conditions for these LD-PCR PCR exercises were as described in Example 6. The reverse amplification primer employed in these reactions (p316Kpn-RC, 56mer), listed as SEQ ID No. 13, is complementary to a sequence located ~3 Kbp downstream of the predicted HMW protein termination codon. As an aide to cloning the desired ~6 Kbp amplimer, a single KpnI restriction endonuclease site 5' to the chlamydial sequence was engineered into the p316Kpn-RC primer. The forward amplification primer used for these reactions (p306Kpn-F, 56mer), listed as SEQ ID No. 12, contains the sequence complementary to the first 10 amino acid residues (30 nucleotides) specifying the mature HMW protein as well as a 5' sequence specifying a KpnI site. p306Kpn-F was designed such that the sequence encoding the N-terminus of the mature HMW protein could be linked in-frame to a hexa-His affinity domain encoded downstream of the highly efficient trc promoter on the *E. coli* expression vector pTrcHisB (ClonTech) when the ~6 Kbp amplimer was inserted into the KpnI site of this vector.

SEQ ID No.12 5'-AAG-GGC-CCA-ATT-ACG-CAG-AGG-GTA-CCG-AAA-TTA-TGG-TTC-CTC-AAG-GAA-TTT-ACG-AT-3'

SEQ ID No.13 5'-AAG-GGC-CCA-ATT-ACG-CAG-AGG-GTA-CCC-TAA-GAA-GAA-GGC-ATG-CCG-TGC-TAG-CGG-AG-3'

The ~6 Kbp HMW protein products were purified using silica-gel spin columns (QIAGEN) and the fragments subjected to two 8–10 hour cycles of KpnI digestion using a 10-fold excess of KpnI (~10 units per 1 μg of purified fragment, 37° C.). Following the second digestion, residual restriction enzyme activity was removed using QIAGEN spin columns and the ~6 Kbp KpnI HMW protein fragments cloned into the pTrcHisB plasmid which had been previously digested to completion with KpnI and treated with calf intestinal phosphatase to prevent vector religation.

Vector/insert ligations were performed in a ~50 μl final reaction volume (50 mM Tris-HCl, pH 7.00; 10 mM NaCl; 1 mM ATP; 0.5 mM DTT) at 25° C. for ~2 hours using T4 DNA ligase (~10 units/reaction) and a vector:insert molar ratio of approximately 1:5. Following ligation, aliquots (~50 ng ligated DNA) was used to electroporate a competent *E. coli* host, e.g. *E. coli* TOP10. Plasmid-harboring transformants were selected by plating electrotransformed cells onto LB agar containing 100 μg/ml ampicillin. Ampicillin-resistant ($Ap^R$) transformants appearing after a ~18–24 hour incubation period at 37° C. were picked at random and restreaked onto the same selective media for purification.

A single, purified $Ap^R$ colony from each initial transformant was used to inoculate ~5 ml of LB broth and grown overnight at 37° C. in a incubator shaker with mild aeration (~200 rpm). Cells from broth cultures were harvested by centrifugation and used to prepare small quantities of plasmid DNA. Commercially available reagents (QIAGEN Plasmid Mini Kits) were employed for these plasmid extractions. Plasmid derivatives carrying inserts were presumptively identified by electrophoresing the non-digested plasmid DNA in agarose gels (0.8% agarose in TAE buffer) and identifying derivatives greater in size than vector plasmid. Insert-containing derivatives were confirmed and the orientation of the HMW protein inserts relative to vector sequences were determined using appropriate restriction endonucleases (KpnI, EcoRI, HindIII, BamHI, etc.), either separately or together in various combinations.

The DNA sequence of the *C. trachomatis* B and F HMW protein genes were obtained for both strands using "sequence walking" the asymmetric dye-terminator PCR cycle sequencing methodology (ABI Prism Dye-Terminator Cycle Sequencing, Perkin-Elmer) described in Example 4. Reactions were programmed with plasmid mini-prep DNA and individual HMW protein sequence-specific primers that were employed in the sequencing of the HMW protein gene from the $L_2$ type strain.

DNA sequence data were collected using the ABI 310 Sequenator and analyzed automatically on a PowerMAC computer and appropriate computer software as described in Example 4. Individually autoanalyzed DNA sequences were edited manually for accuracy before being merged into a consensus sequence "string" using AutoAssembler software (Perkin-Elmer). Both strands of the HMW protein gene from the *C. trachomatis* B and F seovars were sequences for both the *C. trachomatis* B and F HMW protein genes. The amino acid sequences encoded are listed as SEQ ID NOS.: 15 and 16. Sequence comparisons of the $L_2$, F and B strains are presented in FIG. 6.

8.9. Example 9

Production of Recombinant Protein

To produce sufficient quantities of recombinant HMW protein for both immunogenicity and animal protection studies, the HMW gene has been PCR cloned into suitable *E. coli* and baculovirus expression systems. Large quantities of rHMW protein are produced in an *E. coli*—based system as a chimeric fusion protein containing an N-terminal $(His)_6$ affinity purification domain. The complete HMW protein open reading frame (ORF) was PCR-cloned from the *C. trachomatis* $L_2$ genome as a single KpnI fragment and fused in the proper orientation and in the correct reading frame to the $(His)_6$ affinity purification domain encoded on the high expression plasmid vector pTrcHisB (CloneTech) as described in Example 5.

The $(His)_6$ affinity purification domain is part of a high expression locus consisting of the highly efficient tac promoter (IPTG-inducible) and consensus Shine and Delgarno ribosome binding site (RBS) located immediately upstream of the $(His)_6$ affinity purification domain. The HMW protein genes from *C. trachomatis* LGV $L_2$, *C. trachomatis* B, and *C. trachomatis* F were PCR cloned as ~3.0 Kbp fragments. The forward primer (56-mer) used in these reactions was designated p306Kpn-F and contains sequences complementary to the first 10 N-terminal amino acid residues of the mature HMW protein, listed as SEQ ID No 12. In addition to the HMW protein coding sequences, this forward primer also carries a unique KpnI restriction site located optimally located upstream of the first residue of the mature HMW protein (Glu) for proper fusion to the $(His)_6$ affinity purification domain encoded on the vector plasmid, and 5' terminal 6 base G/C clamp for effective amplification and a 12 base internal spacer for effective endonuclease recognition/digestion. The reverse PCR primer, designated p316Kpn-3RC, contains a reverse complement sequence to a *C. trachomatis* sequence located ~0.2 Kbp downstream of the HMW protein termination codon, listed as SEQ ID No. 14. As with p306Kpn-F, the reverse primer also contains a KpnI restriction site 5' to the *C. trachomatis* sequences, a 6 base G/C clamp, and a 12 base internal spacer.

To obtain acceptacle yields of the HMW protein ORF product (about 3,500 bp), PCR amplification was performed using a mixture of thermostable DNA polymerases consisting of *T. thermophilus* DNA polymerase as the primary amplification polymerase and a minor amount of a second high fidelity thermostable DNA polymerase to provide additional 5'-3' proofreading activity (Advantage Polymerase, CloneTech). An anti-Tth DNA polymerase antibody was added to the reaction mixture to provide automatic 'hot-start' conditions which foster the production of large (>2 Kbp) amplimers.

Genomic DNA from the various *C. trachomatis* strains was isolated from EBs as described in the example above and used to program these reactions. Following amplification, the desired reaction products were purified from excess primers using commercially available silica-gel spin columns and reagents (QIAGEN) and digested to completion with an excess of KpnI (~10 units per 1 µg DNA). The purified and digested KpnI HMW protein ORF was then be cloned into the KpnI predigested pTrcHisB expression plasmid (5:1, insert:vector ratio). Aliquots from the ligation reaction were then used to electrotransform a suitable *E. coli* host (e.g. TOP10).

Mini-prep DNA from ampicillin-resistant transformants picked at random were prepared, digested to completion with KnI, HindIII, or a combination of both and examined for the presence and orientation of the ~3.2 Kbp HMW protein ORF insert by agarose gel electrophoresis and ethidium bromide staining. Mini-prep DNA was used to program asymmetric PCR DNA sequencing reactions as described in example(s) above to confirm the fidelity of the junction formed between the HMW protein fragment and the $(His)_6$ affinity purification domain of the vector. Plasmid pAH342 was one derivative isolated by these procedures, which contains the HMW protein gene ORF from *C. trachomatis* $L_2$ and is represented by nucleotides 466 to 3421 in FIG. 2.

Recombinants were grown in 2X-YT broth containing 100 $\mu$g/ml Ap to mid-log phase (~0.5 $O.D._{600}$) and induced with IPTG (1 mM final) for an additional 4–5 hours to activate transcription from the vectors trc promoter. Cells were harvested by centrifugation and crude cell lysates prepared by lysis using a French pressure cell.

Alternatively, expression of rHMW protein may be obtained by using a baculovirus expression system. Here, the HMW protein ORF from *C. trachomatis* $L_2$ and *C. trachomatis* F were PCR-cloned as ~3 Kbp PCR products into a baculovirus transfer vector (e.g. pFastBacHTb) that had been previously digested to completion with KpnI and treated with CIP to minimize vector religation in essentially the same manner as described for pTrcHisB. The HMW protein expression cartridge generated in this cloning exercise (i.e. the baculovirus polyhedron promoter, N-terminal $(His)_6$ affinity purification domain, HMW protein gene ORF) was then transferred to the baculovirus genome by site-specific transposition using a commercially available bacmid system (Bac-to-Bac, Gibco)

Briefly, the HMW protein baculovirus expression plasmid was used to transform competent *E. coli* DH10bac (Gibco) cells containing a bacmid (a hybrid baculovirus-plasmid replicon) to gentamicin resistance using standard transformation and selection methodologies. Transformants where the HMW protein expression cartridge had successfully transposed from the expression plasmid to the appropriate receptor site within the lacZ gene located on the bacmid replicon were identified using a standard IPTG/X-gal blue-white selection.

White, $Gm^R$ transformants were picked at random and restreaked for purification. Bacmid DNA was prepared from broth cultures by the method of Ish-Horowitz, *N. A. R.* 9:2989–2993 (1981) incorporated herein by reference, and is used to transfect *Spodoptera frugiperda* 9 cells. Following plaque purification, recombinant HMW protein baculovirus is used to infect large scale Spodoptera suspension cultures. A yeast expression system is used to generate a glycosylated form of HMW protein.

8.10. Example 10

Purification of Recombinant Protein

Recombinant HMW protein was purified to homogeneity using standard preparative immobilized metal affinity chromatography (IMAC) procedures. Briefly, an *E. coli* strain harboring an expression plasmid containing HMW protein gene was grown in Luria broth in a 5 l fermenter (New Brunswick) at 37° C. with moderate aeration until mid-log phase (~0.5 $O.D._{600}$) and induced with IPTG (1 mM final) for 4–5 hours. Cell paste was collected, washed in PBS and stored at −20° C. Aliquots of frozen cell paste (~9–10 grams wet weight) were suspended in ~120 ml of D-PBS by mechanical agitation and lysed by passage through a French pressure cell (2×, 14,000 psi, 4° C.). Soluble protein was then removed from rHMW protein inclusion bodies by high speed centrifugation (~10,000×g, 4° C., 30 min).

The insoluble pellet containing rHMW protein was suspended in ~20 ml of ice cold D-PBS by homogenization and centrifuged as above. Washed rHMW protein inclusion bodies were then denatured by suspension in a sodium phosphate buffer (0.1 M, pH 7.0) containing 6M guanidine hydrochloride and loaded onto a $Ni^{2+}$-affinity column (1.5 cm×25 cm, bed volume ~15 ml) prepared from Fast-Flow Chelating Sepharose (Pharmacia) and charged with $Ni^{2+}$ or $Zn^{2+}$ ions by standard procedures. Unbound material was removed by washing the column with ~5–10 column volumes of a sodium phosphate buffer (0.1 M, pH 7.0) containing 8M urea.

Recombinant HMW protein bound to the affinity resin by virtue of the N-terminal $(His)_6$ affinity purification domain was eluted using a pH 4.0 sodium phosphate/8M urea buffer (~20 ml). Eluted material was neutralized by the addition of 1.0 M Tris-HCl (~2.5 ml, pH 7.5) and dialyzed against TE buffer containing SDS (0.5%) to remove the urea. Dialyzed material was concentrated using a Centricon-30 centrifugal concentrator (Amicon, 30,000 MWCO) and mixed with a 1/5 volume of 5× SDS gel sample buffer containing 1 mM 2-mercaptoethanol (Lammeli) and boiled at 100° C. for 5 minutes.

Samples were loaded onto Tris/glycine preparative acrylamide gels (4% stacking gel, 12% resolving gel, 30:0.8 acrylamide:bis solution, 3 mm thickness). A prestained molecular weight standard (See Blue, Novex) was run in parallel with the rHMW protein samples to identify size fractions on the gel. The area of the gel containing proteins having molecular masses of ~110 Kdal was excised and the proteins electroplated using an Elu-Trap device and membranes (S&S) as specified by the manufacturer. Electroplated protein was dialyze to remove SDS. The protein concentration of the sample was determining using a Micro-BCA system (Pierce) and BSA as a concentration standard. The purity of rHMW protein was determined using conventional SDS-PAGE and commercially available silver staining reagents (Silver Stain Plus, Novel) as shown in FIG. 4.

The apparent molecular weight of the isolated mature rHMW is about 105–115 kDa as determined by SDS-PAGE.

8.11. Example 11

Preparation of Antibodies to HMW Protein

Polyvalent antisera directed against the HMW protein were generated by vaccinating rabbits with the purified HMW protein or fragments thereof. Each animal was given a total of three immunizations of about 250 μg HMW protein or fragment thereof per injection (beginning with complete Freund's adjuvant and followed with incomplete Freund's adjuvant) at approximately 21 day intervals. At each immunization, approximately half of the material was administered intramuscularly (i.m.) and half was injected intranodally. Fourteen days after the third vaccination a fourth booster of about 100 μg HMW protein was given i.m. and the animals exsanguinate 7–10 days later. Anti-HMW protein titers were measured by ELISA using purified HMW protein (1.0 μg/well) or C. trachomatis $L_2$ EBs (whole and crude protein extracts) as capture ligands. Immunogen specific IgG ELISA titres of 1/320,000 were observed using purified rHMW truncated protein and 1/2500 using either EBs and RBs.

Serial dilutions of antisera were made in PBS and tested by ELISA in duplicate. Goat HRP-conjugated anti-rabbit antibody diluted 1/1000 was used as the second reporter antibody in these assays. Titers are expressed as the greatest dilution showing a positive ELISA reaction, i.e. an O.D.$_{450}$ value >2SD above the mean negative control value (prebleed rabbit sera). Hyperimmune antisera was then used to probe Western blots of crude EB or RB extracts as well as 1.0% OGP EB extract preparations to determine whether other C. trachomatis serovars and Chlamydia species express the HMW protein. C. trachomatis serovars B, Ba, D, F, G, I, J, K, $L_1$, $L_2$, $L_3$, MoPn and Chlamydia pneumoniae were tested and found to have a protein of an apparent molecular weight of 105–115 KDa reactive with antisera generated against HMW protein.

8.12. Example 12

Surface Localization

Surface localization of the HMW protein on different Chlamydia strains and derivatives were examined by indirect fluorescence antibody (IFA). IFA was performed using the procedures generally known in the art using hyperimmune anti-HMW protein as the primary antibody. Hak cells infected with whole EBs from one of C. trachomatis serovars $L_2$, B, and F, C. pneumoniae or C. psittaci are achieved by the following method.

McCoy or Hak cells were grown to confluence in D-MEM media on 12 mm plain coverslips inside 24 well tissue culture plates then centrifugally inoculated with $-5\times10^4$ inclusion forming units (IFU) of the *C. trachomatis* strain N11 (serover F). After ~24 hours incubation, the culture media was removed and infected cells fixed inmethanol for 10 min. The fixed monoloayer was then washed with PBS (1×) to remove fixative and overlayer with >300 μl of anti-60Kdal truncated HMWP rabbit antibody that had been diluted ~1/100 in PBS. After 1 hour incubation with the primary antibody, the cells were washed gently with PBS then incubated for ~30 min. with a 1/200 dilution of a mouse anti-rabbit IgG antibody conjugated with FITC. The second antibody was diluted using a PBS solution containing 0.0091% Evans Blue as a counter stain to visualize the monolayer. Cells were washed 2× in PBS to remove the secondary antibody, the coverslips removed from the culture plates, and mounted onto microscope slides using a fluorescent mounting medium.

Identical cell samples stained with prebleed rabbit antibody or FITC-conjugated second antibody alone were processed in parallel and served as antibody specificity (negative) controls. Counterstained samples were examined at a 1000-× magnification with a Zeiss Axioskop photomicroscope equipped with plan-neoflur objectives. Results using *C. trachomatis NI*1 (F serovar) are shown in FIG. 7. The results show that enhanced fluorescence of samples stained with HMW protein antibody compared to the controls confirmed the surface location of the HMW protein. Furthermore, fluorescence of samples stained with HMW protein antibodies show binding to surface localized HMW protein from $L_2$, B and MoPn serovars and *C. pneuomoniae.*

9. EXAMPLE

In Vitro Neutralization Model

The in vitro neutralization model has been used to show that protective antiserum inhibited chlamydial infection (neutralization) of various tissue culture cell lines. Animal models are also essential for testing vaccine efficacy with both small animal (non-primate) and primate models necessary for preclinical evaluation. The guinea-pig has been used for studying experimental ocular and genital infection by the Guinea-pig inclusion conjunctivitis agent (GPIC), *C. psittaci.*

The mouse offers a consistent and reproducible model of genital tract infection using human genital tract isolates. This mouse model is a generally accepted pre-clinical assay, and was used to evaluate MOMP as a subunit vaccine. Another model is known as the primate model of trachoma infection wherein the induction of secretory IgA was shown to be a prime component of protection. Vaccinogenic ability of new subunit antigen candidates is determined using the above-mentioned generally accepted in vitro neutralization and animal model systems.

As a preliminary exercise to the animal protection studies, hyperimmune anti-HMW antibody was evaluated for its ability to block the infectivity of various *C. trachomatis serovars (e.g. $L_2$*, B, F) in vitro. Although McCoy cells were used to propagate Chlamydia, these cells also allow antibody-mediated uptake via Fc receptors. Therefore, to evaluate anti-HMW antibody inhibition of infectivity, Hak cells, which do not display Fc receptors, were used in these analyses.

Cells were grown on coverslips in 24-well plates to a subconfluent monolayer (about 90% confluency=$1\times10^5$ cells/ml) at 37° C. in 5% $CO_2$. Anti-HMW-antibody was diluted to about 100 μg/ml (total protein) in sucrose-phosphate-glutamate (SPG) buffer and then serially diluted in SPG buffer. Frozen aliquots of pretitered Chlamydia was diluted in SPG buffer to about $2\times10^4$ IFU/ml. EBs were premixed with the diluted anti-HMW-antibody to about 10–20 IFU/μl and incubated 30 minutes at 37° C. on a rocking platform.

Prepared Hak cells were washed in HBSS and then incubated with the anti-HMW-antibody/Chlamydia EB mixture in triplicate for each antibody using 500 IFU/ml. Plates were incubated for 2 hours at 37° C., then the inoculum removed and plates washed 3 times with HBSS. Tissue culture media containing 1 μg/ml of cyclohexamide was added and plates incubated for about 24–36 hours at 37° C. in 5% $CO_2$ to allow inclusion bodies to develop. After incubation, the media was removed and cell monolayers washed 3× in PBS. Plates were fixed in methanol for 20 minutes and re-washed in PBS.

Cells were stained to visualize inclusions by incubating with anti-Chlamydia LPS antibody (diluted about 1:500, ViroStat), cells washed 3 times in PBS, followed by incubation with FITC-conjugated goat secondary antibody for 30 minutes at 37° C. Coverslips were washed, air dried, and mounted in glycerol on glass coverslips. Inclusions were counted in five fields through the midline of the coverslip on a Zeiss fluorescence photomicroscope. Results are reported as the percent reduction of inclusion-containing cells with respect to a heterogenous antibody control (rabbit prebleed sera).

10. EXAMPLE

Vaccine Efficacy (Mouse Model of Salpingitis and Fertility)

10.1. Methods

10.1.0. Immunization and Challenge

The Tuffrey murine infertility model was employed to evaluate the efficacy of rHMWP to protect animals against Chlamydia trachomatis-induced salpingitis and infertility. Three groups of 17 female C3H HeOuJ mice (~6 weeks of age, Jackson Labs) were employed for this evaluation. The test group of 17 animals was immunized at weeks 0, 2, and 3 by intranasal administration of ~20 µl of a vaccine formulation containing approximately 10–12 µg of gel-purified rHMWP and ~5 µg mLT (SmithKline Beecham) as adjuvant. Prior to immunization mice were sedated using an anesthesia cocktail consisting of 16% Ketaject and 16% Xylaject in 68% pyrogen-free PBS (100 µl i.p./animal). Sedated animals were placed on their backs and using a standard laboratory pipette administered the vaccine formulation; ~10 µl of the vaccine solution per nostril with a 5–10 minute wait period between applications.

Two groups of 17 female mice (per test group) were immunized similarly but with a preparation containing only 5 µg mLT (i.e. adjuvant only, no antigen). One of these groups was subsequently challenged with C. trachomatis (sham-immunized, infected) and served as the negative fertility control while the other group was not challenged (sham immunized, sham infected) and served as the positive fertility control.

At week 4, all animals were administered a single i.p. dose of progesterone (2.5 mg in pyrogen-free PBS, Depo-Provera, Upjohn) to stabilize the uterine epithelium. At week 5, animals immunized with rHMWP and animals in the negative control group were infected by bilateral intrauterine inoculation with ~5×10$^5$ inclusion forming units (IFU) of C. trachomatis NI1 (serovar F) in 100 µl of sucrose phosphate glutamate buffer (SPG). To mimic the manipulations to the reproductive tract experienced by the other two groups, animals in the positive control were bilaterally inoculated with 100 µl of a McCoy cell extract that contained no C. trachomatis. At week 7, 5–7 animals from each group were sacrificed by $CO_2$ asphyxiation and the complete genital tract (both upper and lower reproductive tracts) removed for histopathological analysis. At week 9, the remaining females from each group were caged with 8–10 week old male C3H mice for a 2 month breeding period to assess fertility (1 male for every 2 females per cage with weekly rotation of the males within each group, animals from different experimental groups were not mixed). Palpation and periodic weighing were used to determine when animals in each pair became pregnant. The parameters used to estimate group fertility were: F, the number of mice which littered at least once during the mating period divided by the total number of mice in that study group; M, the number of newborn mice (born dead or alive) divided by the number of litters produced in that group during the mating period; and N, the number of newborn mice (born dead or alive) divided by the total number of mice in that group.

10.1.2. Histopathology

Genital tracts were treated for ≧24 hrs in Bouin's fixative, progressively dehydrated in 50%, 70%, and 100% methanol, soaked in toluol, and either paraffin embedded or directly embedded in OCT compound (Tissue-TEK, Miles) and subsequently snap frozen in liquid nitrogen. Tissue sections (~6 µm) were stained with hematoxylin and eosin (after deparaffinization of the Bouin fixed samples). Inflammatory changes in the oviducts and ovaries were graded as follows: 0, no apparent inflammatory reaction; 1, a few mononuclear cells infiltrating the periovarial space or the submucosa of the oviduct; 2, same as 1 but to a greater extent; 3, same as 2 but with a thickened oviductal submucosa and the presence of inflammatory cells in the oviductal lumen; 4, same as 3 but to a greater extent. Inflammation in the cervix/vagina was scored based on the level of the intraepithelial infiltrate observed.

10.1.3. Determination of rHMWP-Specific Humoral Responses

Blood samples were collected periodically during the immunization and challenge phases by retroorbital bleeding and serum prepared by centrifugation. Vaginal secretions were collected by repeated injection of 50 µl of sterile PBS into the vagina with a standard laboratory pipettor and immediately withdrawing the solution. Two-to-three injection/withdrawal cycles were performed.

Quantitation of antibody (Ab) responses by ELISA were performed as described in Section 8.11. Microwell ELISA plates (Maxisorb, NUNC) for determining Ab levels were coated overnight at 4° C. with ~0.5–1.0 µg of gel-purified rHMWP per well in 10 mM carbonate/bicarbonate buffer (pH 9.6), washed with PBS containing 0.1% Tween-20 (washing buffer) and blocked for ~1 hr at 37° C. with a PBS solution containing 3% BSA. For the determination of antigen-specific serum IgG levels, test sera were serially diluted in washing buffer containing 0.5% BSA and aliquots (100 µl) incubated in the antigen-coated wells for ~2 hr at 37° C. The plates were then washed and incubated for ~1 hr at 37° C. with a horseradish peroxidase (HRP)-conjugated goat anti-mouse IgG second antibody (Sigma). A HRP-conjugated goat anti-mouse IgA secondary antibody was used to detect the presence of—rHMWP-specific IgA in vaginal secretions. After incubation with the appropriate secondary Ab, the plates were washed and incubated for ~20–30 minutes at room temperature with TMB substrate (Sigma). Reactions were stopped by the addition of 2M $H_2SO_4$ and the absorbance determined at 450 nm on a Molecular Devices SpectroMax microplate reader. Titers were determined as the reciprocal of the sample dilution corresponding to an optical density of 1.0 at 450 nm.

10.1.4. Determination of rHMWP-Specific Cellular Responses

Groups of 6 female C3H HeOuJ mice (Jackson Labs) were sedated and immunized at weeks 0, 2 and 3 by intranasal administration with the rHMWP+mLT vaccine as described in Section 10.1.3. At weeks 4 and 5 immediately prior to progesterone treatment and intrauterine challenge, respectively, 3 animals from each group were sacrificed by $CO_2$ asphyxiation and spleens aseptically removed and single cell suspensions prepared using conventional methodologies. Spleen cells from immunized animals were analyzed separately. For both the positive control group (sham immunized and sham infected) and the negative control group (sham immunized, infected) spleen cells were pooled and tested for restimulation.

For the measurement of spleen cell proliferation, spleens were ground (5 to 10 rounds) in 5 ml of RPMI 1640 Glutamax I supplemented with 10% fetal calf serum, 25 mM HEPES, 50 U/ml penicillin, 50 μg/ml streptomycin, 1 mm sodium pyruvate, nonessential amino acids, and 50 μM 2-mercaptoethanol (Gibco-BRL). Live cells were counted by Trypan Blue staining and diluted in the same media to reach a density of $1.0-2.0 \times 10^6$ cells/ml (Falcon 2063 polypropylene tubes). Triplicate cultures were set-up in round bottom 96-well culture plates (Nunclon, Nunc) using $\sim 5 \times 10^5$ responder cells per well in 200 μl of media Cells were stimulated with either 1.0 μg/ml of rHMWP (antigen-specific proliferation) or with 4 μg/ml concanavalin A (Boerhinger Mannheim) as a positive stimulation control; unrestimulated cell cultures were used as a negative control of cellular activation. After 72–96 hours of incubation at 37° C. in 5% $CO_2$ cells were pulsed labelled for ~18 hrs with 1.0 μCi $^3$H-thymidine (Amersham) per well. Pulsed cells were harvested onto glass-fiber sheets using a Tomtec Cell Harvester (Mk III) and counted for beta-emission in a 3-channel Wallac 1450 Trilux Liquid Scintillation Counter. The stimulation index (SI) for a sample (individual or pooled) was defined as the mean of the antigen or ConA-stimulated T-cell uptake of $^3$H-thymidine for triplicate wells divided by the mean of the unstimulated uptake for triplicate wells. SIs for both antigen-specific (rHMWP-specific) and ConA-specific proliferation were determined.

10.2. Results 10.2.1. Effect on Mouse Fertility After a Heterotypic Challenge

Evidence that mucosal immunization with rHMWP combined with mLT can afford protection against infertility caused by a human clinical isolate of C. trachomatis (strain NI1, serovar F) is shown in Table 1. Animals immunized with the rHMWP displayed a significantly higher fertility rate (70%, i.e. number of fertile females in group/total number of animals in the group) than animals in the negative control group (30%, sham immunized and infected). Similarly, the rHMWP immunized group produced more offspring and exhibited a group fecundity greater than those observed in the negative control group (51 vs 24 offspring and 5.1±4.7 vs 2.4±4.6 fecundity scores, respectively). As a group, animals immunized with the rHMWP vaccine displayed a comparable fertility rate, total number of offspring, and a fecundity score to those observed in the sham infected positive control group (80% fertility rate, 56 total offspring, 4.9±2.7 fecundity).

The protection against C. trachomatis-induced infertility obtained in this experiment also demonstrates the utility of the rHMWP to afford cross-biovar and cross-serovar protection against C. trachomatis disease. The recombinant HMWP antigen employed in this experiment was cloned from a strain belonging to the C. trachomatis lymphogranuloma venereum (LGV) group (strain L2) which causes systemic as well as more localized mucosal infections of the eye and genital tract. The C. trachomatis challenge organism used in these experiments, strain NI1 is an F serovar organism that belongs to the trachoma biovar which causes numerous urogenital tract infections.

TABLE 1

Fertility Assessments Observed After ~2 Breeding Cycles

| Group | Number of Animals per Group | Percent Fertile Animals | Number of Off-spring | Group Fecundity[1] (Mean + SD) |
|---|---|---|---|---|
| rHMWP-Immunized | 10 | 70<br>p = 0.089[2] | 51 | 5.10 ± 4.68<br>p = 0.105[3] |
| Sham Immunized Sham Infected (Positive Control) | 10 | 80<br>p = 0.035 | 56 | 4.90 ± 2.70<br>p = 0.078 |
| Sham Immunized Infected (Negative Control) | 10 | 30 | 24 | 2.40 ± 4.61 |

[1]Mean number of pups per group
[2]Fisher's exact test, one-sided, 95% confidence interval
p-values are given relative to the negative control
[3]Student's t-test, unpaired, Gausian distribution, 95% confidence interval
p-values are given relative to the negative control 10.2.2. Effect on Cellular Immune Response The rHMWP-specific activation of the cellular immune system was demonstrated using a conventional spleen cell proliferation assay. When spleen cells were tested during week 4 (immediately prior to progesterone treatment) (Table 2) and week 5 (~7 days after hormone treatment but before intrauterine challenge) (Table 3), all samples collected from rHMWP-immunized animals developed a strong antigen-specific proliferative immune response. The antigen-specific Stimulation Indexes (SIs) obtained prior to progesterone treatment from rHMWP-immunized animals were equal to or greater than the SIs obtained via mitogenic stimulation with ConA (mean values for antigen and ConA stimulation obtained from 3 rHMWP-immunized animals: 26.2 vs 18.4, respectively). Spleen cells obtained from either sham immunized animals or naive animals (i.e. animals that were not exposed to either the rHMWP antigen or mLT) did not respond to in vitro restimulation with the rHMWP material, thus establishing the specificity of the proliferative response observed in the immunized animals. Progesterone treatment did not affect the antigen-specific proliferative response observed in rHMWP immunized animals. Antigen-specific SIs obtained with spleen cells obtained after hormone treatment were greater than obtained via mitogenic stimulation (mean values for antigen and ConA stimulation obtained from 3 rHMWP-immunized animals: 92.4 vs 37.8, respectively). Again samples collected from sham immunized or naive animals failed to demonstrate any antigen-specific proliferative response.

TABLE 2 rHMWP-Specific Cell Proliferation Before Hormone Treatment

| Group | Cell Proliferation (cpm) Untreated/ConA/rHMWP | Stimulation Index (Treated cpm/ Untreated cpm) ConA/rHMWP |
|---|---|---|
| rHMWP Immunized Animal #1 | 1557/20739/65741 | 13.3/42.2 |
| rHMWP Immunized Animal #2 | 1508/26975/28361 | 17.9/18.8 |
| rHMWP Immunized Animal #3 | 1238/29991/23453 | 24.0/18.9 |
| Sham-Immunized Animals (Pooled) | 1687/30546/1292 | 18/<1.0 |
| Naive Animals (Pooled) | 335/23886/838 | 71/2.5 |

TABLE 3 rHMWP-Specific Cell Proliferation After Hormone Treatment

| Group | Cell Proliferation (cpm) Untreated/ConA/rHMWP | Stimulation Index (Treated cpm/ Untreated cpm) ConA/rHMWP |
|---|---|---|
| rHMWP Immunized Animal #1 | 767/15934/97458 | 20.8/127.0 |
| rHMWP Immunized Animal #2 | 546/17212/28172 | 31.5/51.6 |
| rHMWP Immunized Animal #3 | 297/18139/29300 | 61.1/98.6 |
| Sham-Immunized Animal (Pooled) | 273/18094/150 | 66.3/<1.0 |
| Naive Animals (Pooled) | 345/16740/1341 | 48.5/3.9 |

10.2.3. Effect of Humoral Immune Response

To demonstrate that immunization with the full length rHMWP produces a humoral immune response, IgG titers were measured by ELISA on sera collected at week 5 immediately prior to challenge (i.e. approximately 2 weeks after the third immunization). As shown in Table 4, immunization of C3H mice with three doses of ~10–12 µg rHMWP produced detectable levels of anti-rHMWP IgG in all animals. Vaginal secretions were also collected from these animals at the same time and tested for the presence of anti-rHMWP mucosal IgA. Antigen-specific vaginal IgA was detected in three animals (Table 4).

TABLE 4 rHMWP-Specific Humoral Response

| rHMWP Immunized Animal | Anti-rHMWP Serum IgG ELISA Titer | Presence of Anti-rHMWP Vaginal IgA |
|---|---|---|
| 4.4 | 5,000 | |
| 4.5 | 6,000 | |
| 4.6 | 12,000 | + |
| 4.7 | 130 | |
| 4.8 | 100 | |
| 4.9 | 54,000 | + |
| 4.10 | 670 | |
| 4.11 | 100 | |
| 4.12 | 570 | |
| 4.13 | 100,000 | + |
| 4.14 | 4,500 | |
| 4.15 | 400 | |
| 4.16 | 1,600 | |
| 4.17 | 2,500 | |
| 4.18 | 700 | |
| 4.19 | 70,000 | |
| 4.20 | 500 | |
| 4.21 | 2,000 | |
| 4.22 | 18,000 | |
| 4.23 | 3,000 | |
| Mean ± S.D. | 18.5 ± 29.6 | |

11. EXAMPLE

Construction of PJJ701

A plasmid containing the entire *C. trachomatis* $L_2$ HMWP gene was constructed by selectively removed the EcoRI site upstream to the HMWP N-terminus in pAH306 (Described in Section 8.4). This was accomplished by digesting pAH306 to completion with XhoI and then religating the plasmid to create pAH306-XhoΔ-1. The ~2.5 Kbp EcoRI fragment from pAH316 (described in Section 8.5) which contains the remaining HMWP C-terminus was isolated from preparative agarose gels that had been loaded with a complete EcoRI digestion of pAH316. An agarose gel slice containing the appropriate ~2.5 Kbp fragment was then excised, dissolved with NaI buffer and purified from residual agarose by hydroxyapatite spin column chromatography (QiaGen). The purified C-terminal HMWP EcoRI fragment was then ligated into the single EcoRI site of pAH306-XhoΔ-1, located at the 3'-end of the HMWP N-terminal coding sequence, using T4 DNA ligase and standard molecular biology protocols. *E. coli* Top10 cells were transformed with an aliquot of the pAH306-XhoΔ-1 (EcoRI digested and phosphatase treated vector) and the 2.5 Kbp EcoRI C-terminal fragment ligation reaction and recombinants selected on 2X-YT agar containing 100 $\mu$g/ml ampicillin. Ampicillin-resistant transformants were picked at random. Plasmid DNA was isolated from individual $Ap^R$ transformants using a QiaGen Mini-Prep Plasmid DNA Isolation System and screened for the presence of plasmids greater in size than pAH306-XhoΔ-1 by conventional agarose gel electrophoresis and ethidium bromide staining. Derivatives of pAH306-XhoΔ-1 carrying the 2.5 Kbp HMWP fragment in the proper orientation that would allow expression of the full length HMWP were identified by restriction analyses using EcoRI and/or XhoI. Plasmid pAH374 was one derivative isolated from this experiment.

A PCR-based site-directed mutagenesis procedure (QuikChange Site-Directed Mutagenesis System, Stratagene) was employed to effect a desired DNA change, namely to remove the NdeI site within the HMWP coding sequence of pAH374. Mutagenic PCR primers, 41 bases in length and complementary to the sequencing containing the NdeI site and designated 140-Nde-FX and 140-NdeRCX, were designed so as to eliminate the NdeI recognition site but not change the corresponding protein coding sequence. The sequences of the two PCR mutagenic primers employed to remove the NdeI site in pAH374 are given below.

140-Nde-FX(SEQ ID NO: 38)

5'-GGG TTT GGG AAT CAG CAC ATG AAA ACC TCA TAT ACA TTT GC-3'

140-Nde-RCX(SEQ ID NO:39)

5'-GCA AAT GTA TAT GAG GTT TTC ATG TGC TGA TTC CCA AAC CC-3'

Following Pfu DNA polymerase (Stratagene) mutagenesis and DpnI digestion, to cleave any unaltered pAH374 parental plasmid, mutated plasmid DNA was then transformed into E. coli XL1-Blue. Plasmid harboring transformants were selected on 2X-YT agar containing 100 µg/ml ampicillin. Antibiotic resistant transformants were picked at random and screened for plasmids of the size as pAH374. The identity of plasmids isolated from transformants was determined by restriction enzyme digestion using EcoRI. The absence of the NdeI site in these plasmids was determined by digestion using NdeI. To verify the loss of the HMWP NdeI site and to ensure no unwanted DNA sequence changes had occurred in this region during the mutagenesis procedure, mutagenized plasmids were further subjected to DNA sequence analysis using a sequence-specific sequencing primer located upstream of the NdeI site. Plasmid pAH374-NdeΔ-1 was one plasmid isolated from this experiment.

A DNA fragment encoding the C. trachomatis $L_2$ HMWP without the internal NdeI site, plasmid pAH374-NdeΔ-1, was PCR amplified from reactions programmed with plasmid pAH374-NdeΔ-1 (~50 ng) and primers 306-Nde-Met1 and 312H6Xba1. Primer 306NdeMet1 was designed to contain a central NdeI site for directed cloning onto pMG81. The NdeI site in 306NdeMet1 overlapped the ATG start codon for HMWP signal sequence and was flanked by a 20 base G/C clamp on the 5' side and sequences complementary to the first 15 residues of the HMWP signal sequence on the 3' side. Primer 312H6Xba1 was designed to contain sequences complementary to the C-terminus of the HMWP followed by a $(CAT)_6$ motif specifying a hexa-histidine affinity purification domain. This primer also contained two UAA termination codons, an XbaI recognition sequence, and a 20 base G/C clamp at the 3' end of the primer. The sequences of the 306NdeMet1 and 312H6Xba1 PCR primers are given below.

306NdeMet1 (SEQ ID NO: 40)

5'-AAG GGC CCA ATT ACG CAG ACA TAT GGA AAC GTC TTT CCA TAA GTT CTT TCT TTC A-3'

312H6Xba1 (SEQ ID NO: 41)

5'-AAG GGC CCA ATT ACG CAG AGT CTA GAT TAT TAA TGA TGA TGA TGA TGA TGG AAC CGG ACT CTA CTT CCT GCA CTC AAA CC-3'

PCR amplification conditions described in Section 8.4 were used to generate the NdeI-XbaI HMWP gene cassette. Following amplification, the PCR product was purified using hydroxyapatite spin columns (QiaGen) and digested overnight at 37° C. with a ~10-fold excess of NdeI and XbaI to generate the required 'overhangs' at the ends of the fragment. The digested fragment was again purified using spin columns and ~250 ng ligated to ~50 ng pMG81 plasmid DNA that had been previously digested to completion with NdeI and XbaI and subsequently treated with CIP to prevent vector religation. An aliquot of the ligation reaction was used to transform E. coli strain AR58 which had been made competent by the method of Lederberg and Cohen. Transformants were selected on 2X-YT agar containing 40 µg/ml kanamycin sulfate. Due to the temperature inducible promoter on pMG81, the transformed cells were grown at 30° C. Kanamycin-resistant transformants were picked at random and screened for the presence of plasmids ~3.0 Kbp larger in size than pMG81. Insert containing derivatives of pMG81 were confirmed by restriction enzyme analysis using NdeI, XbaI, EcoRI and NcoI. Plasmid pJJ701 was one plasmid isolated from this exercise.

12. EXAMPLE 16

Production of Full Length rHMWP from AR58 (PJJ701)

One milliliter of a frozen stock of E. coli strain AR58 containing plasmid pJJ701 was used to inoculate ~100 ml of 2X-YT broth containing 40 µg/ml kanamycin and grown overnight at 30° C. to prepare a fermentor seed culture. Approximately 20 ml of the overnight seed culture was then used to inoculate a New Brunswick Bioflow 3000 fermentor loaded with ~2.01 of 2X-YT broth containing 40 µg/ml kanamycin. The AR58 (pJJ701) culture was grown at 30° C. with vigorous aeration until an $O.D._{625}$ value of 0.5–0.6 was attained. Expression of rHMWP was induced by increasing the temperature of the fermentor culture to ~39° C. to 42° C. Incubation at the elevated temperature was continued for approximately 4–5 hours.

At the end of the induction period, the E. coli culture, with some cells displaying classic recombinant protein inclusion bodies, was harvested by continuous flow centrifugation using an Heraeus Contifuge 28RS centrifuge. Following centrifugation, cell mass was scraped from the centrifuge bowl and stored at −70° C. until processed.

Approximately 15 gm of the AR58 (pJJ701) frozen cell paste was resuspended by vortexing and trituration in ~40 ml of ice cold 10 mM sodium phosphate buffer, pH7.3. Once suspended, lysozyme (Chicken egg white, Sigma) and DNase I (Bovine pancreas, Sigma) were added to final concentrations of 1.0 mg/ml and 0.01 mg/ml, respectively, and the mixture incubated on ice for 30–45 minutes. Cells were disrupted by 2 sequential passes through a pre-cooled (~4° C.) SLM Aminco French Pressure Cell (~14 Kpsi, 1" diameter bore). The cell lysate was then centrifuged for 5 min at ~500×g (4° C.) in a Sorvall SS34 rotor to remove unbroken cells. Insoluble material containing the rHMWP was isolated (pelleted) by centrifugation for 45 min at ~20,000×g (4° C.) in a Sorvall SS34 rotor. The supernatant from this centrifugation was discarded and the insoluble fraction stored at −20° C. in pellet form.

To selectively extract contaminating proteins and remove endotoxin, the rHMWP-containing insoluble pellet was thawed on ice and washed twice with 10 ml of PBS buffer containing 2.0% Triton X-100. Washing was performed at room temperature and suspension of the gelatinous rHMWP-containing pellet was accomplished by vortexing and homogenization in a conventional glass tissue grinder. Insoluble material containing the rHMWP was recovered after washing by centrifugation at ~10,000×g for 20 minutes (room temperature) in a Sorvall SS34 rotor. Insoluble material was then washed (again by vortexing and homogenization) 2-times with 10 ml of a 4.0 M urea solution containing 2.0 M NaCl. Washed rHMWP material was recovered by centrifugation as above. The insoluble rHMWP fraction was further washed 2-times with 10 ml of a PBS solution containing 1.0% Zwittergent 3-14 (Sigma).

The rHMWP pellet recovered after centrifugation of the final wash solution was then solubilized for 2 hours at room temperature in standard Laemelli SDS-PAGE sample buffer containing 4 M urea. Solubilized rHMWP was size fractionated into a single protein band of ~110 Kdal by electrophoresis through a standard ~14 cm×~20 cm×~3 mm 10% polyacrylamide (36:1, acrylamide:bis-acrylamide) Tris/glycine/SDS preparative gel. A 4% polyacrylamide stacking gel formed using a 5-well, ~500 μl/well preparative comb was polymerized on top of the resolving gel. Electrophoresis was carried out on a BioRad Protean unit for ~12 hours at ~22° C. (~80–85 volts, constant voltage) using a conventional Tris/glycine/SDS running buffer (BioRad). Prestained molecular weight standards (SeeBlue, Novex) were loaded into a parallel lane and were used to gauge the degree and efficiency of separation of the protein species. Following electrophoresis, the gel sandwich was disassembled and a vertical slice was removed from the rHMWP sample lane adjacent to the molecular weight markers and stained with coomassie blue R250 to visualize the rHMWP band. The stained section was then repositioned onto the remaining unstained preparative gel and the strip of acrylamide containing the rHMWP identified and excised.

rHMWP was eluted from the gel slice using a Schleicher and Schuell EluTrap electroelution device. Electroelution was carried out according to the manufacturers recommendations except 1/4-strength SDS running buffer (Novex) was used as the elution buffer. Elution was carried out at ~40 mA for ~12–14 hours, at room temperature. At the end of the elution period the polarity of the cell was reversed for ~2–3 minutes to remove any protein absorbed to the BT1 membrane. The rHMWP-containing solution was removed from the collection chamber and stored in a polypropylene conical tube at 4° C.

Excess SDS detergent was removed using an SDS precipitation system (SDS-OUT Precipitation kit, Pierce Chemical). Removal of excess detergent from the gel-eluted protein solution was accomplished following the manufacturer's protocol. Detergent extracted rHMWP was diluted approximately 15 fold with sterile, endotoxin-free 10 m Molar sodium phosphate buffer (pH 7.4) and concentrated to approximately 1.0 mg/ml by ultrafiltration in an Amicon stirred concentration cell using a YM30 ultrafiltration membrane.

Residual endotoxin was removed from the concentrated rHMWP solution by polymyxin B Affi-Prep Polymyxin Matrix (BioRad) treatment. Affi-Prep treatment was performed overnight at 4° C. in a batch mode according to the manufacturers recommendations.

The protein concentration of the concentrated, polymyxin B-treated rHMWP was determined using the Micro BCA method (Pierce Chem.) and BSA as a standard.

Purified rHMWP (~0.9–1.2 mg/ml protein concentration) was evaluated for purity, identity, and residual endotoxin burden by SDS-PAGE, Western blot, and a colorimetric endotoxin assay (BioWhittaker), respectively. The gel-purified rHMWP material displayed a purity of >95% as a single band of the expected molecular size (~110 Kdal) by gel analysis and reacted vigorously with rHMWP-specific K196 antibody in Western blots. Residual endotoxin was calculated to be ≦0.05 EU/μg.

---

What is claimed is:

1. A method of producing an immune response in an animal comprising, administering to said animal, an effective amount of an antigenic composition, comprising an adjuvant and an isolated *Chlamydia* species high molecular weight (HMW) protein, said HMW protein encoded by a nucleic acid comprising nucleotide residues 466 to 3417 of SEQ ID NO.:1, wherein the *Chlamydia* species is *Chlamydia trachomatis, Chlamydia pecorum,* or *Chlamydia pneumoniae.*

2. The method of claim 1, wherein said HMW protein comprises an amino acid sequence of amino acid residues 29 to 1012 of SEQ ID NO.:2.

3. The method of claim 1, wherein said HMW protein is obtained using plasmid pAH342 obtainable from *E. coli* BL21 (pAH342) assigned ATCC accession number 98538.

4. A method of producing an immune response in an animal, comprising administering to said animal, an effective amount of an antigenic composition, comprising a pharmaceutical carrier and an isolated recombinantly produced *Chlamydia* species HMW protein, said HMW protein encoded by a nucleic acid comprising a nucleotide sequence of SEQ ID NO.:1, wherein the *Chlamydia* species is *Chlamydia trachomatis, Chlamydia pecorum,* or *Chlamydia pneumoniae.*

5. A method of producing an immune response in an animal, comprising administering to said animal, an effective amount of an antigenic composition, comprising a pharmaceutical carrier and an isolated recombinantly produced *Chlamydia* species HMW protein, wherein said HMW protein comprises an amino acid sequence of SEQ ID NO.:2.

6. A method of producing an immune response in an animal, comprising administering to said animal, an effective amount of an antigenic composition, comprising a pharmaceutical carrier and an isolated recombinantly produced *Chlamydia* species HMW protein, wherein said HMW protein is obtained using plasmid pJJ701 obtainable from *E. coli* AR58 (pJJ701) assigned ATCC accession number PTA-4123.

7. A method of producing an immune response in an animal, comprising administering to said animal, an effective amount of an antigenic composition, comprising a pharmaceutical carrier and an isolated recombinantly produced *Chlamydia trachomatis, C. pecorum* or *C. pneumoniae* HMW protein, wherein said HMW protein is encoded by a nucleic acid having a nucleotide sequence which hybridizes under conditions comprising 50% formamide and 37° C. to a nucleotide sequence complementary to the nucleotide sequence of SEQ ID NO.:1 from residue 466 to residue 3417, and which HMW protein is recognized by an antibody that specifically binds to a peptide comprising an amino acid sequence of SEQ ID NO.:2.

8. The method of anyone of claims 1–7, wherein said composition is formulated as a microparticle, a capsule, a liposome preparation or an emulsion.

9. The method of anyone of claims 4–7, wherein said animal is a mammal or a bird.

10. The method of anyone of claims 4–7, wherein said composition further comprises an adjuvant.

* * * * *

SEQUENCE LISTING

```
<160> NUMBER OF SEQ ID NOS: 43

<210> SEQ ID NO 1
<211> LENGTH: 4435
<212> TYPE: DNA
<213> ORGANISM: Artificial Sequence
<220> FEATURE:
<223> OTHER INFORMATION: Description of Artificial Sequence: Recombinant
      Expression Vector
<221> NAME/KEY: CDS
<222> LOCATION: (382)..(3417)
<223> OTHER INFORMATION:

<400> SEQUENCE: 1
gggcaaaact cttcccccg ggatttatat gggaaagggg aaactttggc ccgtattcaa      60
gcgccacggg ttttggggcg gaatgaattt tttcgttccg gaaaaagtaa ttccccggga    120
acgtagggta tcggtttcat aggctcgcca aatgggatat aggtggaaag gtaaaaaaaa    180
ctgagccaag caaaggatag agaagtcttg taatcatcgc aggttaaagg ggggatgtta    240 tttagcctg caaatagtgt aattattgga tcctgtaaag agaaaaggac gaatgcgctg    300
aagataagaa catttattga tattaaatta ttaatttttt atgaagcgga gtaattaatt   360
ttatctctca gcttttgtgt g atg caa acg tct ttc cat aag ttc ttt ctt    411
                          Met Gln Thr Ser Phe His Lys Phe Phe Leu
                            1               5                  10 tca atg att cta gct tat tct tgc tgc tct tta aat ggg ggg gga tat    459
Ser Met Ile Leu Ala Tyr Ser Cys Cys Ser Leu Asn Gly Gly Gly Tyr
           15                  20                  25
```

```
gca gca gaa atc atg gtt cct caa gga att tac gat ggg gag acg tta    507
Ala Ala Glu Ile Met Val Pro Gln Gly Ile Tyr Asp Gly Glu Thr Leu
         30                  35                  40 act gta tca ttt ccc tat act gtt ata gga gat ccg agt ggg act act    555
Thr Val Ser Phe Pro Tyr Thr Val Ile Gly Asp Pro Ser Gly Thr Thr
             45                  50                  55 gtt ttt tct gca gga gag tta aca tta aaa aat ctt gac aat tct att    603
Val Phe Ser Ala Gly Glu Leu Thr Leu Lys Asn Leu Asp Asn Ser Ile
 60                  65                  70 gca gct ttg cct tta agt tgt ttt ggg aac tta tta ggg agt ttt act    651
Ala Ala Leu Pro Leu Ser Cys Phe Gly Asn Leu Leu Gly Ser Phe Thr
 75                  80                  85                  90 gtt tta ggg aga gga cac tcg ttg act ttc gag aac ata cgg act tct    699
Val Leu Gly Arg Gly His Ser Leu Thr Phe Glu Asn Ile Arg Thr Ser
                 95                 100                 105 aca aat ggg gca gct cta agt aat agc gct gct gat gga ctg ttt act    747
Thr Asn Gly Ala Ala Leu Ser Asn Ser Ala Ala Asp Gly Leu Phe Thr
             110                 115                 120 att gag ggt ttt aaa gaa tta tcc ttt tcc aat tgc aat tca tta ctt    795
Ile Glu Gly Phe Lys Glu Leu Ser Phe Ser Asn Cys Asn Ser Leu Leu
         125                 130                 135 gcc gta ctg cct gct gca acg act aat aag ggt agc cag act ccg acg    843
Ala Val Leu Pro Ala Ala Thr Thr Asn Lys Gly Ser Gln Thr Pro Thr
 140                 145                 150 aca aca tct aca ccg tct aat ggt act att tat tct aaa aca gat ctt    891
Thr Thr Ser Thr Pro Ser Asn Gly Thr Ile Tyr Ser Lys Thr Asp Leu
155                 160                 165                 170 ttg tta ctc aat aat gag aag ttc tca ttc tat agt aat tta gtc tct    939
Leu Leu Leu Asn Asn Glu Lys Phe Ser Phe Tyr Ser Asn Leu Val Ser
                 175                 180                 185 gga gat ggg gga gct ata gat gct aag agc tta acg gtt caa gga att    987
Gly Asp Gly Gly Ala Ile Asp Ala Lys Ser Leu Thr Val Gln Gly Ile
             190                 195                 200 agc aag ctt tgt gtc ttc caa gaa aat act gct caa gct gat ggg gga   1035
Ser Lys Leu Cys Val Phe Gln Glu Asn Thr Ala Gln Ala Asp Gly Gly
         205                 210                 215 gct tgt caa gta gtc acc agt ttc tct gct atg gct aac gag gct cct   1083
Ala Cys Gln Val Val Thr Ser Phe Ser Ala Met Ala Asn Glu Ala Pro
 220                 225                 230 att gcc ttt gta gcg aat gtt gca gga gta aga ggg gga ggg att gct   1131
Ile Ala Phe Val Ala Asn Val Ala Gly Val Arg Gly Gly Gly Ile Ala
235                 240                 245                 250 gct gtt cag gat ggg cag cag gga gtg tca tca tct act tca aca gaa   1179
Ala Val Gln Asp Gly Gln Gln Gly Val Ser Ser Ser Thr Ser Thr Glu
                 255                 260                 265 gat cca gta gta agt ttt tcc aga aat act gcg gta gag ttt gat ggg   1227
Asp Pro Val Val Ser Phe Ser Arg Asn Thr Ala Val Glu Phe Asp Gly
             270                 275                 280 aac gta gcc cga gta gga gga ggg att tac tcc tac ggg aac gtt gct   1275
Asn Val Ala Arg Val Gly Gly Gly Ile Tyr Ser Tyr Gly Asn Val Ala
         285                 290                 295 ttc ctg aat aat gga aaa acc ttg ttt ctc aac aat gtt gct tct cct   1323
Phe Leu Asn Asn Gly Lys Thr Leu Phe Leu Asn Asn Val Ala Ser Pro
 300                 305                 310 gtt tac att gct gct aag caa cca aca agt gga cag gct tct aat acg   1371
Val Tyr Ile Ala Ala Lys Gln Pro Thr Ser Gly Gln Ala Ser Asn Thr
315                 320                 325                 330 agt aat aat tac gga gat gga gga gct atc ttc tgt aag aat ggt gcg   1419
Ser Asn Asn Tyr Gly Asp Gly Gly Ala Ile Phe Cys Lys Asn Gly Ala
```

-continued

```
                      335                 340                 345
caa gca gga tcc aat aac tct gga tca gtt tcc ttt gat gga gag gga      1467
Gln Ala Gly Ser Asn Asn Ser Gly Ser Val Ser Phe Asp Gly Glu Gly
            350                 355                 360 gta gtt ttc ttt agt agc aat gta gct gct ggg aaa ggg gga gct att      1515
Val Val Phe Phe Ser Ser Asn Val Ala Ala Gly Lys Gly Gly Ala Ile
        365                 370                 375 tat gcc aaa aag ctc tcg gtt gct aac tgt ggc cct gta caa ttt tta      1563
Tyr Ala Lys Lys Leu Ser Val Ala Asn Cys Gly Pro Val Gln Phe Leu
380                 385                 390 agg aat atc gct aat gat ggt gga gcg att tat tta gga gaa tct gga      1611
Arg Asn Ile Ala Asn Asp Gly Gly Ala Ile Tyr Leu Gly Glu Ser Gly
395                 400                 405                 410 gag ctc agt tta tct gct gat tat gga gat att att ttc gat ggg aat      1659
Glu Leu Ser Leu Ser Ala Asp Tyr Gly Asp Ile Ile Phe Asp Gly Asn
            415                 420                 425 ctt aaa aga aca gcc aaa gag aat gct gcc gat gtt aat ggc gta act      1707
Leu Lys Arg Thr Ala Lys Glu Asn Ala Ala Asp Val Asn Gly Val Thr
        430                 435                 440 gtg tcc tca caa gcc att tcg atg gga tcg gga ggg aaa ata acg aca      1755
Val Ser Ser Gln Ala Ile Ser Met Gly Ser Gly Gly Lys Ile Thr Thr
    445                 450                 455 tta aga gct aaa gca ggg cat cag att ctc ttt aat gat ccc atc gag      1803
Leu Arg Ala Lys Ala Gly His Gln Ile Leu Phe Asn Asp Pro Ile Glu
460                 465                 470 atg gca aac gga aat aac cag cca gcg cag tct tcc aaa ctt cta aaa      1851
Met Ala Asn Gly Asn Asn Gln Pro Ala Gln Ser Ser Lys Leu Leu Lys
475                 480                 485                 490 att aac gat ggt gaa gga tac aca ggg gat att gtt ttt gct aat gga      1899
Ile Asn Asp Gly Glu Gly Tyr Thr Gly Asp Ile Val Phe Ala Asn Gly
            495                 500                 505 agc agt act ttg tac caa aat gtt acg ata gag caa gga agg att gtt      1947
Ser Ser Thr Leu Tyr Gln Asn Val Thr Ile Glu Gln Gly Arg Ile Val
        510                 515                 520 ctt cgt gaa aag gca aaa tta tca gtg aat tct cta agt cag aca ggt      1995
Leu Arg Glu Lys Ala Lys Leu Ser Val Asn Ser Leu Ser Gln Thr Gly
    525                 530                 535 ggg agt ctg tat atg gaa gct ggg agt aca tgg gat ttt gta act cca      2043
Gly Ser Leu Tyr Met Glu Ala Gly Ser Thr Trp Asp Phe Val Thr Pro
540                 545                 550 caa cca cca caa cag cct cct gcc gct aat cag ttg atc acg ctt tcc      2091
Gln Pro Pro Gln Gln Pro Pro Ala Ala Asn Gln Leu Ile Thr Leu Ser
555                 560                 565                 570 aat ctg cat ttg tct ctt tct tct ttg tta gca aac aat gca gtt acg      2139
Asn Leu His Leu Ser Leu Ser Ser Leu Leu Ala Asn Asn Ala Val Thr
            575                 580                 585 aat cct cct acc aat cct cca gcg caa gat tct cat cct gca gtc att      2187
Asn Pro Pro Thr Asn Pro Pro Ala Gln Asp Ser His Pro Ala Val Ile
        590                 595                 600 ggt agc aca act gct ggt tct gtt aca att agt ggg cct atc ttt ttt      2235
Gly Ser Thr Thr Ala Gly Ser Val Thr Ile Ser Gly Pro Ile Phe Phe
    605                 610                 615 gag gat ttg gat gat aca gct tat gat agg tat gat tgg cta ggt tct      2283
Glu Asp Leu Asp Asp Thr Ala Tyr Asp Arg Tyr Asp Trp Leu Gly Ser
620                 625                 630 aat caa aaa atc aat gtc ctg aaa tta cag tta ggg act aag ccc cca      2331
Asn Gln Lys Ile Asn Val Leu Lys Leu Gln Leu Gly Thr Lys Pro Pro
635                 640                 645                 650 gct aat gcc cca tca gat ttg act cta ggg aat gag atg cct aag tat      2379
Ala Asn Ala Pro Ser Asp Leu Thr Leu Gly Asn Glu Met Pro Lys Tyr
```

```
                Ala Asn Ala Pro Ser Asp Leu Thr Leu Gly Asn Glu Met Pro Lys Tyr
                            655                 660                 665 ggc tat caa gga agc tgg aag ctt gcg tgg gat cct aat aca gca aat              2427
Gly Tyr Gln Gly Ser Trp Lys Leu Ala Trp Asp Pro Asn Thr Ala Asn
            670                 675                 680 aat ggt cct tat act ctg aaa gct aca tgg act aaa act ggg tat aat              2475
Asn Gly Pro Tyr Thr Leu Lys Ala Thr Trp Thr Lys Thr Gly Tyr Asn
        685                 690                 695 cct ggg cct gag cga gta gct tct ttg gtt cca aat agt tta tgg gga              2523
Pro Gly Pro Glu Arg Val Ala Ser Leu Val Pro Asn Ser Leu Trp Gly
    700                 705                 710 tcc att tta gat ata cga tct gcg cat tca gca att caa gca agt gtg              2571
Ser Ile Leu Asp Ile Arg Ser Ala His Ser Ala Ile Gln Ala Ser Val
715                 720                 725                 730 gat ggg cgc tct tat tgt cga gga tta tgg gtt tct gga gtt tcg aat              2619
Asp Gly Arg Ser Tyr Cys Arg Gly Leu Trp Val Ser Gly Val Ser Asn
                735                 740                 745 ttc tat cat gac cgc gat gct tta ggt cag gga tat cgg tat att              2667
Phe Phe Tyr His Asp Arg Asp Ala Leu Gly Gln Gly Tyr Arg Tyr Ile
            750                 755                 760 agt ggg ggt tat tcc tta gga gca aac tcc tac ttt gga tca tcg atg              2715
Ser Gly Gly Tyr Ser Leu Gly Ala Asn Ser Tyr Phe Gly Ser Ser Met
        765                 770                 775 ttt ggt cta gca ttt acc gaa gta ttt ggt aga tct aaa gat tat gta              2763
Phe Gly Leu Ala Phe Thr Glu Val Phe Gly Arg Ser Lys Asp Tyr Val
    780                 785                 790 gtg tgt cgt tcc aat cat cat gct tgc ata gga tcc gtt tat cta tct              2811
Val Cys Arg Ser Asn His His Ala Cys Ile Gly Ser Val Tyr Leu Ser
795                 800                 805                 810 acc caa caa gct tta tgt gga tcc tat ttg ttc gga gat gcg ttt atc              2859
Thr Gln Gln Ala Leu Cys Gly Ser Tyr Leu Phe Gly Asp Ala Phe Ile
                815                 820                 825 cgt gct agc tac ggg ttt ggg aat cag cat atg aaa acc tca tat aca              2907
Arg Ala Ser Tyr Gly Phe Gly Asn Gln His Met Lys Thr Ser Tyr Thr
            830                 835                 840 ttt gca gag gag agc gat gtt cgt tgg gat aat aac tgt ctg gct gga              2955
Phe Ala Glu Glu Ser Asp Val Arg Trp Asp Asn Asn Cys Leu Ala Gly
        845                 850                 855 gag att gga gcg gga tta ccg att gtg att act cca tct aag ctc tat              3003
Glu Ile Gly Ala Gly Leu Pro Ile Val Ile Thr Pro Ser Lys Leu Tyr
    860                 865                 870 ttg aat gag ttg cgt cct ttc gtg caa gct gag ttt tct tat gcc gat              3051
Leu Asn Glu Leu Arg Pro Phe Val Gln Ala Glu Phe Ser Tyr Ala Asp
875                 880                 885                 890 cat gaa tct ttt aca gag gaa ggc gat caa gct cgg gca ttc aag agc              3099
His Glu Ser Phe Thr Glu Glu Gly Asp Gln Ala Arg Ala Phe Lys Ser
                895                 900                 905 gga cat ctc cta aat cta tca gtt cct gtt gga gtg aag ttt gat cga              3147
Gly His Leu Leu Asn Leu Ser Val Pro Val Gly Val Lys Phe Asp Arg
            910                 915                 920 tgt tct agt aca cat cct aat aaa tat agc ttt atg gcg gct tat atc              3195
Cys Ser Ser Thr His Pro Asn Lys Tyr Ser Phe Met Ala Ala Tyr Ile
        925                 930                 935 tgt gat gct tat cgc acc atc tct ggt act gag aca acg ctc cta tcc              3243
Cys Asp Ala Tyr Arg Thr Ile Ser Gly Thr Glu Thr Thr Leu Leu Ser
    940                 945                 950 cat caa gag aca tgg aca aca gat gcc ttt cat tta gca aga cat gga              3291
His Gln Glu Thr Trp Thr Thr Asp Ala Phe His Leu Ala Arg His Gly
955                 960                 965                 970
```

-continued

```
gtt gtg gtt aga gga tct atg tat gct tct cta aca agt aat ata gaa       3339
Val Val Val Arg Gly Ser Met Tyr Ala Ser Leu Thr Ser Asn Ile Glu
            975                 980                 985 gta tat ggc cat gga aga tat gag tat cga gat gct tct cga  ggc tat      3387
Val Tyr Gly His Gly Arg Tyr Glu Tyr Arg Asp Ala Ser Arg  Gly Tyr
        990                 995                 1000 ggt ttg agt  gca gga agt aga gtc  cgg ttc taaaaatatt ggttagatag       3437
Gly Leu Ser  Ala Gly Ser Arg Val  Arg Phe
        1005                1010 ttaagtgtta gcgatgcctt tttctttgag atctacatca ttttgttttt tagcttgttt     3497
gtgttcctat tcgtatggat tcgcgagctc tcctcaagtg ttaacgccta atgtaaccac     3557
tccttttaag ggagacgatg tttacttgaa tggagactgc gcttttgtca atgtctatgc     3617
aggagctgaa gaaggttcga ttatctcagc taatggcgac aatttaacga ttaccggaca     3677
aaaccataca ttatcattta cagattctca agggccagtt cttcaaaatt atgccttcat     3737
ttcagcagga gagacactta ctctgagaga ttttcgagt ctgatgttct cgaaaaatgt      3797
ttcttgcgga gaaagggaa tgatctccgg gaaaaccgtg agtatttccg gagcaggcga      3857
agtgattttc tgggataact ccgtgggta ttctcccttta tctactgtgc caacctcatc    3917
atcaactccg cctgctccaa cagttagtga tgctcggaaa gggtctattt tttctgtaga    3977
gactagtttg gagatctcag gcgtcaaaaa agggtcatg ttcgataata atgccgggaa     4037
tttcggaaca gttttcgag gtaagaataa taataatgct ggtggtggag gcagtgggtt     4097
ccgctcacc atcaagtacg acttttacag ttaaaaactg taaagggaaa gtttctttca    4157
cagataacgt agcctcttgc ggaggcggag tggtttataa aggcattgtg cttttcaaag   4217
acaatgaagg aggcatattc ttccgaggga acacagcata cgatgattta aggattcttg    4277
ctgctactaa tcaggatcag aatacggaga caggaggcgg tggaggagtt atttgctctc    4337
cagatgattc tgtaaagttt gaaggcaata aaggttctat tgtttttgat tacaactttg    4397
caaaaggcag aggcggaagc atcctaacga aagaattc                             4435
```

<210> SEQ ID NO 2
<211> LENGTH: 1012
<212> TYPE: PRT
<213> ORGANISM: Chlamydia sp.

<400> SEQUENCE: 2

```
Met Gln Thr Ser Phe His Lys Phe Phe Leu Ser Met Ile Leu Ala Tyr
1               5                   10                  15

Ser Cys Cys Ser Leu Asn Gly Gly Gly Tyr Ala Ala Glu Ile Met Val
            20                  25                  30

Pro Gln Gly Ile Tyr Asp Gly Glu Thr Leu Thr Val Ser Phe Pro Tyr
        35                  40                  45

Thr Val Ile Gly Asp Pro Ser Gly Thr Thr Val Phe Ser Ala Gly Glu
    50                  55                  60

Leu Thr Leu Lys Asn Leu Asp Asn Ser Ile Ala Ala Leu Pro Leu Ser
65                  70                  75                  80

Cys Phe Gly Asn Leu Gly Ser Phe Thr Val Leu Gly Arg Gly His
            85                  90                  95

Ser Leu Thr Phe Glu Asn Ile Arg Thr Ser Thr Asn Gly Ala Ala Leu
            100                 105                 110

Ser Asn Ser Ala Ala Asp Gly Leu Phe Thr Ile Glu Gly Phe Lys Glu
        115                 120                 125

Leu Ser Phe Ser Asn Cys Asn Ser Leu Leu Ala Val Leu Pro Ala Ala
```

-continued

```
            130                 135                 140
Thr Thr Asn Lys Gly Ser Gln Thr Pro Thr Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Leu Val Ser Gly Asp Gly Ala Ile
                180                 185                 190

Asp Ala Lys Ser Leu Thr Val Gln Gly Ile Ser Lys Leu Cys Val Phe
                195                 200                 205

Gln Glu Asn Thr Ala Gln Ala Asp Gly Ala Cys Gln Val Val Thr
    210                 215                 220

Ser Phe Ser Ala Met Ala Asn Glu Ala Pro Ile Ala Phe Val Ala Asn
225                 230                 235                 240

Val Ala Gly Val Arg Gly Gly Ile Ala Ala Val Gln Asp Gly Gln
                245                 250                 255

Gln Gly Val Ser Ser Thr Ser Thr Glu Asp Pro Val Val Ser Phe
            260                 265                 270

Ser Arg Asn Thr Ala Val Glu Phe Asp Gly Asn Val Ala Arg Val Gly
            275                 280                 285

Gly Gly Ile Tyr Ser Tyr Gly Asn Val Ala Phe Leu Asn Asn Gly Lys
            290                 295                 300

Thr Leu Phe Leu Asn Asn Val Ala Ser Pro Val Tyr Ile Ala Ala Lys
305                 310                 315                 320

Gln Pro Thr Ser Gly Gln Ala Ser Asn Thr Ser Asn Asn Tyr Gly Asp
                325                 330                 335

Gly Gly Ala Ile Phe Cys Lys Asn Gly Ala Gln Ala Gly Ser Asn Asn
                340                 345                 350

Ser Gly Ser Val Ser Phe Asp Gly Glu Gly Val Val Phe Phe Ser Ser
            355                 360                 365

Asn Val Ala Ala Gly Lys Gly Gly Ala Ile Tyr Ala Lys Lys Leu Ser
            370                 375                 380

Val Ala Asn Cys Gly Pro Val Gln Phe Leu Arg Asn Ile Ala Asn Asp
385                 390                 395                 400

Gly Gly Ala Ile Tyr Leu Gly Glu Ser Gly Glu Leu Ser Leu Ser Ala
                405                 410                 415

Asp Tyr Gly Asp Ile Ile Phe Asp Gly Asn Leu Lys Arg Thr Ala Lys
                420                 425                 430

Glu Asn Ala Ala Asp Val Asn Gly Val Thr Val Ser Ser Gln Ala Ile
                435                 440                 445

Ser Met Gly Ser Gly Gly Lys Ile Thr Thr Leu Arg Ala Lys Ala Gly
450                 455                 460

His Gln Ile Leu Phe Asn Asp Pro Ile Glu Met Ala Asn Gly Asn Asn
465                 470                 475                 480

Gln Pro Ala Gln Ser Ser Lys Leu Leu Lys Ile Asn Asp Gly Glu Gly
                485                 490                 495

Tyr Thr Gly Asp Ile Val Phe Ala Asn Gly Ser Ser Thr Leu Tyr Gln
                500                 505                 510

Asn Val Thr Ile Glu Gln Gly Arg Ile Val Leu Arg Glu Lys Ala Lys
                515                 520                 525

Leu Ser Val Asn Ser Leu Ser Gln Thr Gly Gly Ser Leu Tyr Met Glu
    530                 535                 540

Ala Gly Ser Thr Trp Asp Phe Val Thr Pro Gln Pro Pro Gln Gln Pro
545                 550                 555                 560
```

-continued

```
Pro Ala Ala Asn Gln Leu Ile Thr Leu Ser Asn Leu His Leu Ser Leu
                565                 570                 575
Ser Ser Leu Leu Ala Asn Asn Ala Val Thr Asn Pro Thr Asn Pro
            580                 585                 590
Pro Ala Gln Asp Ser His Pro Ala Val Ile Gly Ser Thr Ala Gly
            595                 600                 605
Ser Val Thr Ile Ser Gly Pro Ile Phe Phe Glu Asp Leu Asp Thr
    610                 615                 620
Ala Tyr Asp Arg Tyr Asp Trp Leu Gly Ser Asn Gln Lys Ile Asn Val
625                 630                 635                 640
Leu Lys Leu Gln Leu Gly Thr Lys Pro Pro Ala Asn Ala Pro Ser Asp
                645                 650                 655
Leu Thr Leu Gly Asn Glu Met Pro Lys Tyr Gly Tyr Gln Gly Ser Trp
                660                 665                 670
Lys Leu Ala Trp Asp Pro Asn Thr Ala Asn Asn Gly Pro Tyr Thr Leu
            675                 680                 685
Lys Ala Thr Trp Thr Lys Thr Gly Tyr Asn Pro Gly Pro Glu Arg Val
    690                 695                 700
Ala Ser Leu Val Pro Asn Ser Leu Trp Gly Ser Ile Leu Asp Ile Arg
705                 710                 715                 720
Ser Ala His Ser Ala Ile Gln Ala Ser Val Asp Gly Arg Ser Tyr Cys
                725                 730                 735
Arg Gly Leu Trp Val Ser Gly Val Ser Asn Phe Phe Tyr His Asp Arg
                740                 745                 750
Asp Ala Leu Gly Gln Gly Tyr Arg Tyr Ile Ser Gly Tyr Ser Leu
            755                 760                 765
Gly Ala Asn Ser Tyr Phe Gly Ser Ser Met Phe Gly Leu Ala Phe Thr
            770                 775                 780
Glu Val Phe Gly Arg Ser Lys Asp Tyr Val Val Cys Arg Ser Asn His
785                 790                 795                 800
His Ala Cys Ile Gly Ser Val Tyr Leu Ser Thr Gln Gln Ala Leu Cys
                805                 810                 815
Gly Ser Tyr Leu Phe Gly Asp Ala Phe Ile Arg Ala Ser Tyr Gly Phe
                820                 825                 830
Gly Asn Gln His Met Lys Thr Ser Tyr Thr Phe Ala Glu Glu Ser Asp
            835                 840                 845
Val Arg Trp Asp Asn Asn Cys Leu Ala Gly Glu Ile Gly Ala Gly Leu
    850                 855                 860
Pro Ile Val Ile Thr Pro Ser Lys Leu Tyr Leu Asn Glu Leu Arg Pro
865                 870                 875                 880
Phe Val Gln Ala Glu Phe Ser Tyr Ala Asp His Glu Ser Phe Thr Glu
                885                 890                 895
Glu Gly Asp Gln Ala Arg Ala Phe Lys Ser Gly His Leu Leu Asn Leu
            900                 905                 910
Ser Val Pro Val Gly Val Lys Phe Asp Arg Cys Ser Ser Thr His Pro
    915                 920                 925
Asn Lys Tyr Ser Phe Met Ala Ala Tyr Ile Cys Asp Ala Tyr Arg Thr
    930                 935                 940
Ile Ser Gly Thr Glu Thr Thr Leu Leu Ser His Gln Glu Thr Trp Thr
945                 950                 955                 960
Thr Asp Ala Phe His Leu Ala Arg His Gly Val Val Arg Gly Ser
                965                 970                 975
```

```
Met Tyr Ala Ser Leu Thr Ser Asn Ile Glu Val Tyr Gly His Gly Arg
                980                 985                 990

Tyr Glu Tyr Arg Asp Ala Ser Arg  Gly Tyr Gly Leu Ser  Ala Gly Ser
        995                 1000                1005

Arg Val  Arg Phe
    1010

<210> SEQ ID NO 3
<211> LENGTH: 20
<212> TYPE: PRT
<213> ORGANISM: Chlamydia sp.
<220> FEATURE:
<221> NAME/KEY: SITE
<222> LOCATION: 19
<223> OTHER INFORMATION: Xaa=unknown amino acid

<400> SEQUENCE: 3

Glu Ile Met Val Pro Gln Gly Ile Tyr Asp Gly Glu Thr Leu Thr Val
1               5                   10                  15

Ser Phe Xaa Tyr
            20

<210> SEQ ID NO 4
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c

<400> SEQUENCE: 4
gaaathatgg tnccncaa                                                     18

<210> SEQ ID NO 5
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c

<400> SEQUENCE: 5
gaaathatgg tnccncag                                                     18

<210> SEQ ID NO 6
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c

<400> SEQUENCE: 6
gagathatgg tnccncaa                                                     18

<210> SEQ ID NO 7
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c
```

-continued

```
<400> SEQUENCE: 7
gagathatgg tnccncag                                                      18

<210> SEQ ID NO 8
<211> LENGTH: 15
<212> TYPE: DNA
<213> ORGANISM: Chlamydia sp.
<220> FEATURE:
<221> NAME/KEY: modified_base
<222> LOCATION: 1, 7
<223> OTHER INFORMATION: n = a, t, g, or c

<400> SEQUENCE: 8
ngtytcnccr tcata                                                         15

<210> SEQ ID NO 9
<211> LENGTH: 15
<212> TYPE: DNA
<213> ORGANISM: Chlamydia sp.
<220> FEATURE:
<221> NAME/KEY: modified_base
<222> LOCATION: 1, 7
<223> OTHER INFORMATION: n = a, t, g, or c

<400> SEQUENCE: 9
ngtytcnccr tcgta                                                         15

<210> SEQ ID NO 10
<211> LENGTH: 1511
<212> TYPE: DNA
<213> ORGANISM: Chlamydia sp.

<400> SEQUENCE: 10
gaaatcatgg ttcctcaagg aatttacgat ggggagacgt taactgtatc atttccctat        60
actgttatag gagatccgag tgggactact gttttttctg caggagagtt aacattaaaa      120
aatcttgaca attctattgc agctttgcct ttaagttgtt ttgggaactt attagggagt      180
tttactgttt tagggagagg acactcgttg actttcgaga acatacggac ttctacaaat      240
ggggcagctc taagtaatag cgctgctgat ggactgttta ctattgaggg ttttaaagaa      300
ttatcctttt ccaattgcaa ttcattactt gccgtactgc ctgctgcaac gactaataag      360
ggtagccaga ctccgacgac aacatctaca ccgtctaatg gtactattta ttctaaaaca      420
gatcttttgt tactcaataa tgagaagttc tcattctata gtaatttagt ctctggagat      480
gggggagcta tagatgctaa gagcttaacg gttcaaggaa ttagcaagct ttgtgtcttc      540
caagaaaata ctgctcaagc tgatggggga gcttgtcaag tagtcaccag tttctctgct      600
atggctaacg aggctcctat tgcctttgta gcgaatgttg caggagtaag aggggagggg      660
attgctgctg ttcaggatgg gcagcaggga gtgtcatcat ctacttcaac agaagatcca      720
gtagtaagtt tttccagaaa tactgcggta gagtttgatg ggaacgtagc ccgagtagga      780
ggagggattt actcctacgg gaacgttgct ttcctgaata atggaaaaac cttgtttctc      840
aacaatgttg cttctcctgt ttacattgct gctaagcaac caacaagtgg acaggcttct      900
aatacgagta ataattacgg agatggagga gctatcttct gtaagaatgg tgcgcaagca      960
ggatccaata actctggatc agtttccttt gatggagagg gagtagtttt ctttagtagc     1020
aatgtagctg ctgggaaagg gggagctatt tatgccaaaa agctctcggt tgctaactgt     1080
ggccctgtac aatttttaag gaatatcgct aatgatggtg gagcgattta tttaggagaa     1140
tctggagagc tcagtttatc tgctgattat ggagatatta ttttcgatgg gaatcttaaa     1200
```

-continued

```
agaacagcca aagagaatgc tgccgatgtt aatggcgtaa ctgtgtcctc acaagccatt      1260
tcgatgggat cgggagggaa ataacgaca ttaagagcta aagcagggca tcagattctc       1320
tttaatgatc ccatcgagat ggcaaacgga ataaccagc cagcgcagtc ttccaaactt       1380
ctaaaaatta acgatggtga aggatacaca ggggatattg ttttttgctaa tggaagcagt    1440 actttgtacc aaaatgttac gatagagcaa ggaaggattg tcttcgtga aaaggcaaaa      1500 ttatcagtga a                                                          1511
```

<210> SEQ ID NO 11
<211> LENGTH: 1444
<212> TYPE: DNA
<213> ORGANISM: Chlamydia sp.

<400> SEQUENCE: 11

```
ttctctaagt cagacaggtg ggagtctgta tatggaagct gggagtacat gggattttgt      60
aactccacaa ccaccacaac agcctcctgc cgctaatcag ttgatcacgc tttccaatct     120
gcatttgtct ctttcttctt tgttagcaaa caatgcagtt acgaatcctc ctaccaatcc     180
tccagcgcaa gattctcatc ctgcagtcat tggtagcaca actgctggtt ctgttacaat     240
tagtgggcct atcttttttg aggatttgga tgatacagct tatgataggt atgattggct     300
aggttctaat caaaaaatca atgtcctgaa attacagtta gggactaagc ccccagctaa     360
tgccccatca gatttgactc tagggaatga gatgcctaag tatggctatc aaggaagctg     420
gaagcttgcg tgggatccta atacagcaaa taatggtcct tatactctga agctacatg     480 gactaaaact gggtataatc ctgggcctga gcgagtagct tctttggttc caaatagttt     540
atggggatcc attttagata tacgatctgc gcattcagca attcaagcaa gtgtggatgg     600
gcgctcttat tgtcgaggat tatgggtttc tggagtttcg aatttcttct atcatgaccg     660
cgatgcttta ggtcagggat atcggtatat tagtgggggt tattccttag gagcaaactc     720
ctactttgga tcatcgatgt ttggtctagc atttaccgaa gtatttggta gatctaaaga     780
ttatgtagtg tgtcgttcca atcatcatgc ttgcatagga tccgtttatc tatctaccca     840
acaagcttta tgtggatcct attttgttcgg agatgcgttt atccgtgcta gctacgggtt     900
tgggaatcag catatgaaaa cctcatatac atttgcagag gagagcgatg ttcgttggga     960
taataactgt ctggctggag agattggagc gggattaccg attgtgatta ctccatctaa    1020
gctctatttg aatgagttgc gtccttttcgt gcaagctgag ttttcttatg ccgatcatga    1080 atctttttaca gaggaaggcg atcaagctcg ggcattcaag agcggacatc tcctaaatct    1140
atcagttcct gttggagtga agtttgatcg atgttctagt acacatccta ataaatatag    1200
ctttatggcg gcttatatct gtgatgctta tcgcaccatc tctggtactg agacaacgct    1260
cctatcccat caagagacat ggacaacaga tgcctttcat ttagcaagac atggagttgt    1320
ggttagagga tctatgtatg cttctctaac aagtaatata gaagtatatg gccatggaag    1380
atatgagtat cgagatgctt ctcgaggcta tggttttgagt gcaggaagta gagtccggtt    1440
ctaa                                                                 1444
```

<210> SEQ ID NO 12
<211> LENGTH: 56
<212> TYPE: DNA
<213> ORGANISM: Chlamydia sp.

<400> SEQUENCE: 12

-continued aagggcccaa ttacgcagag ggtaccgaaa ttatggttcc tcaaggaatt tacgat       56

<210> SEQ ID NO 13
<211> LENGTH: 56
<212> TYPE: DNA
<213> ORGANISM: Chlamydia sp.

<400> SEQUENCE: 13
aagggcccaa ttacgcagag ggtaccctaa gaagaaggca tgccgtgcta gcggag       56

<210> SEQ ID NO 14
<211> LENGTH: 57
<212> TYPE: DNA
<213> ORGANISM: Chlamydia sp.

<400> SEQUENCE: 14
aagggcccaa ttacgcagag ggtaccggag agctcgcgaa tccatacgaa taggaac      57

<210> SEQ ID NO 15
<211> LENGTH: 1013
<212> TYPE: PRT
<213> ORGANISM: Chlamydia sp.

<400> SEQUENCE: 15

Met Gln Thr Ser Phe His Lys Phe Phe Leu Ser Met Ile Leu Ala Tyr
1               5                   10                  15

Ser Cys Cys Ser Leu Asn Gly Gly Gly Tyr Ala Ala Glu Ile Met Val
            20                  25                  30

Pro Gln Gly Ile Tyr Asp Gly Glu Thr Leu Thr Val Ser Phe Pro Tyr
        35                  40                  45

Thr Val Ile Gly Asp Pro Ser Gly Thr Thr Val Phe Ser Ala Gly Glu
    50                  55                  60

Leu Thr Leu Lys Asn Leu Asp Asn Ser Ile Ala Ala Leu Pro Leu Ser
65                  70                  75                  80

Cys Phe Gly Asn Leu Leu Gly Ser Phe Thr Val Leu Gly Arg Gly His
                85                  90                  95

Ser Leu Thr Phe Glu Asn Ile Arg Thr Ser Thr Asn Gly Ala Ala Leu
            100                 105                 110

Ser Asp Ser Ala Asn Ser Gly Leu Phe Thr Ile Glu Gly Phe Lys Glu
        115                 120                 125

Leu Ser Phe Ser Asn Cys Asn Pro Leu Leu Ala Val Leu Pro Ala Ala
    130                 135                 140

Thr Thr Asn Asn Gly Ser Gln Thr Pro Ser Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Ser Val Ser Gly Asp Gly Ala Ile
            180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Gly Ala Cys Gln Val Val Thr
    210                 215                 220

Ser Phe Ser Ala Met Ala Asn Glu Ala Pro Ile Ala Phe Val Ala Asn
225                 230                 235                 240

Val Ala Gly Val Arg Gly Gly Gly Ile Ala Ala Val Gln Asp Gly Gln
                245                 250                 255

Gln Gly Val Ser Ser Ser Thr Ser Thr Glu Asp Pro Val Val Ser Phe

```
                    260              265              270
Ser Arg Asn Thr Ala Val Glu Phe Asp Gly Asn Val Ala Arg Val Gly
        275              280              285
Gly Gly Ile Tyr Ser Tyr Gly Asn Val Ala Phe Leu Asn Asn Gly Lys
    290              295              300
Thr Leu Phe Leu Asn Asn Val Ala Ser Pro Val Tyr Ile Ala Ala Glu
305              310              315              320
Gln Pro Thr Asn Gly Gln Ala Ser Asn Thr Ser Asp Asn Tyr Gly Asp
                325              330              335
Gly Gly Ala Ile Phe Cys Lys Asn Gly Ala Gln Ala Ala Gly Ser Asn
                340              345              350
Asn Ser Gly Ser Val Ser Phe Asp Gly Glu Gly Val Val Phe Phe Ser
            355              360              365
Ser Asn Val Ala Ala Gly Lys Gly Gly Ala Ile Tyr Ala Lys Lys Leu
    370              375              380
Ser Val Ala Asn Cys Gly Pro Val Gln Leu Leu Gly Asn Ile Ala Asn
385              390              395              400
Asp Gly Gly Ala Ile Tyr Leu Gly Glu Ser Gly Glu Leu Ser Leu Ser
                405              410              415
Ala Asp Tyr Gly Asp Met Ile Phe Asp Gly Asn Leu Lys Arg Thr Ala
                420              425              430
Lys Glu Asn Ala Ala Asp Val Asn Gly Val Thr Val Ser Ser Gln Ala
            435              440              445
Ile Ser Met Gly Ser Gly Gly Lys Ile Thr Thr Leu Arg Ala Lys Ala
    450              455              460
Gly His Gln Ile Leu Phe Asn Asp Pro Ile Glu Met Ala Asn Gly Asn
465              470              475              480
Asn Gln Pro Ala Gln Ser Ser Glu Pro Leu Lys Ile Asn Asp Gly Glu
                485              490              495
Gly Tyr Thr Gly Asp Ile Val Phe Ala Asn Gly Asn Ser Thr Leu Tyr
            500              505              510
Gln Asn Val Thr Ile Glu Gln Gly Arg Ile Val Leu Arg Glu Lys Ala
            515              520              525
Lys Leu Ser Val Asn Ser Leu Ser Gln Thr Gly Gly Ser Leu Tyr Met
    530              535              540
Glu Ala Gly Ser Thr Leu Asp Phe Val Thr Pro Gln Pro Gln Gln
545              550              555              560
Pro Pro Ala Ala Asn Gln Ser Ile Thr Leu Ser Asn Leu His Leu Ser
                565              570              575
Leu Ser Ser Leu Leu Ala Asn Asn Ala Val Thr Asn Pro Pro Thr Asn
            580              585              590
Pro Pro Ala Gln Asp Ser His Pro Ala Val Ile Gly Ser Thr Thr Ala
            595              600              605
Gly Ser Val Thr Ile Ser Gly Pro Ile Phe Phe Glu Asp Leu Asp Asp
    610              615              620
Thr Ala Tyr Asp Arg Tyr Asp Trp Leu Gly Ser Asn Gln Lys Ile Asp
625              630              635              640
Val Leu Lys Leu Gln Leu Gly Thr Gln Pro Ala Asn Ala Pro Ser
                645              650              655
Asp Leu Thr Leu Gly Asn Glu Met Pro Lys Tyr Gly Tyr Gln Gly Ser
            660              665              670
Trp Lys Leu Ala Trp Asp Pro Asn Thr Ala Asn Asn Gly Pro Tyr Thr
    675              680              685
```

```
Leu Lys Ala Thr Trp Thr Lys Thr Gly Tyr Asn Pro Gly Pro Glu Arg
    690             695                 700

Val Ala Ser Leu Val Pro Asn Ser Leu Trp Gly Ser Ile Leu Asp Ile
705                 710                 715                 720

Arg Ser Ala His Ser Ala Ile Gln Ala Ser Val Asp Gly Arg Ser Tyr
                725                 730                 735

Cys Arg Gly Leu Trp Val Ser Gly Val Ser Asn Phe Phe Tyr His Asp
            740                 745                 750

Arg Asp Ala Leu Gly Gln Gly Tyr Arg Tyr Ile Ser Gly Tyr Ser
        755                 760                 765

Leu Gly Ala Asn Ser Tyr Phe Gly Ser Ser Met Phe Gly Leu Ala Phe
    770                 775                 780

Thr Glu Val Phe Gly Arg Ser Lys Asp Tyr Val Val Cys Arg Ser Asn
785                 790                 795                 800

His His Ala Cys Ile Gly Ser Val Tyr Leu Ser Thr Lys Gln Ala Leu
                805                 810                 815

Cys Gly Ser Tyr Val Phe Gly Asp Ala Phe Ile Arg Ala Ser Tyr Gly
            820                 825                 830

Phe Gly Asn Gln His Met Lys Thr Ser Tyr Thr Phe Ala Glu Glu Ser
        835                 840                 845

Asp Val Cys Trp Asp Asn Asn Cys Leu Val Gly Glu Ile Gly Val Gly
    850                 855                 860

Leu Pro Ile Val Ile Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
                885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
    915                 920                 925

Pro Asn Lys Tyr Ser Phe Met Gly Ala Tyr Ile Cys Asp Ala Tyr Arg
930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser  Arg Gly Tyr Gly Leu  Ser Ala Gly
        995                 1000                1005

Ser Lys  Val Arg Phe
    1010

<210> SEQ ID NO 16
<211> LENGTH: 1013
<212> TYPE: PRT
<213> ORGANISM: Chlamydia sp.

<400> SEQUENCE: 16

Met Gln Thr Ser Phe His Lys Phe Phe Leu Ser Met Ile Leu Ala Tyr
1               5                   10                  15

Ser Cys Cys Ser Leu Thr Gly Gly Gly Tyr Ala Ala Glu Ile Met Val
                20                  25                  30

Pro Gln Gly Ile Tyr Asp Gly Glu Thr Leu Thr Val Ser Phe Pro Tyr
```

-continued

```
            35                  40                  45
Thr Val Ile Gly Asp Pro Ser Gly Thr Val Phe Ser Ala Gly Glu
 50                  55                  60
Leu Thr Lys Asn Leu Asp Asn Ser Ile Ala Ala Leu Pro Leu Ser
 65                  70                  75                  80
Cys Phe Gly Asn Leu Leu Gly Ser Phe Thr Val Leu Gly Arg Gly His
                     85                  90                  95
Ser Leu Thr Phe Glu Asn Ile Arg Thr Ser Thr Asn Gly Ala Ala Leu
                    100                 105                 110
Ser Asp Ser Ala Asn Ser Gly Leu Phe Thr Ile Glu Gly Phe Lys Glu
                    115                 120                 125
Leu Ser Phe Ser Asn Cys Asn Ser Leu Leu Ala Val Leu Pro Ala Ala
                    130                 135                 140
Thr Thr Asn Asn Gly Ser Gln Thr Pro Thr Thr Thr Ser Thr Pro Ser
145                 150                 155                 160
Asn Gly Thr Ile Tyr Ser Lys Thr Asp Leu Leu Leu Asn Asn Glu
                    165                 170                 175
Lys Phe Ser Phe Tyr Ser Asn Leu Val Ser Gly Asp Gly Thr Ile
                    180                 185                 190
Asp Ala Lys Ser Leu Thr Val Gln Gly Ile Ser Lys Leu Cys Val Phe
                    195                 200                 205
Gln Glu Asn Thr Ala Gln Ala Asp Gly Gly Ala Cys Gln Val Val Thr
                    210                 215                 220
Ser Phe Ser Ala Met Ala Asn Glu Ala Pro Ile Ala Phe Ile Ala Asn
225                 230                 235                 240
Val Ala Gly Val Arg Gly Gly Ile Ala Ala Val Gln Asp Gly Gln
                    245                 250                 255
Gln Gly Val Ser Ser Thr Ser Thr Glu Asp Pro Val Val Ser Phe
                    260                 265                 270
Ser Arg Asn Thr Ala Val Glu Phe Asp Gly Asn Val Ala Arg Val Gly
                    275                 280                 285
Gly Gly Ile Tyr Ser Tyr Gly Asn Val Ala Phe Leu Asn Asn Gly Lys
                    290                 295                 300
Thr Leu Phe Leu Asn Asn Val Ala Ser Pro Val Tyr Ile Ala Ala Glu
305                 310                 315                 320
Gln Pro Thr Asn Gly Gln Ala Ser Asn Thr Ser Asp Asn Tyr Gly Asp
                    325                 330                 335
Gly Gly Ala Ile Phe Cys Lys Asn Gly Ala Gln Ala Ala Gly Ser Asn
                    340                 345                 350
Asn Ser Gly Ser Val Ser Phe Asp Gly Glu Gly Val Val Phe Phe Ser
                    355                 360                 365
Ser Asn Val Ala Ala Gly Lys Gly Gly Ala Ile Tyr Ala Lys Lys Leu
                    370                 375                 380
Ser Val Ala Asn Cys Gly Pro Val Gln Phe Leu Gly Asn Ile Ala Asn
385                 390                 395                 400
Asp Gly Gly Ala Ile Tyr Leu Gly Glu Ser Gly Glu Leu Ser Leu Ser
                    405                 410                 415
Ala Asp Tyr Gly Asp Ile Ile Phe Asp Gly Asn Leu Lys Arg Thr Ala
                    420                 425                 430
Lys Glu Asn Ala Ala Asp Val Asn Gly Val Thr Val Ser Ser Gln Ala
                    435                 440                 445
Ile Ser Met Gly Ser Gly Gly Lys Ile Thr Thr Leu Arg Ala Lys Ala
450                 455                 460
```

-continued

```
Gly His Gln Ile Leu Phe Asn Asp Pro Ile Glu Met Ala Asn Gly Asn
465                 470                 475                 480

Asn Gln Pro Ala Gln Ser Ser Glu Pro Leu Lys Ile Asn Asp Gly Glu
                485                 490                 495

Gly Tyr Thr Gly Asp Ile Val Phe Ala Asn Gly Asn Ser Thr Leu Tyr
            500                 505                 510

Gln Asn Val Thr Ile Glu Gln Gly Arg Ile Val Leu Arg Glu Lys Ala
                515                 520                 525

Lys Leu Ser Val Asn Ser Leu Ser Gln Thr Gly Gly Ser Leu Tyr Met
        530                 535                 540

Glu Ala Gly Ser Thr Leu Asp Phe Val Thr Pro Gln Pro Gln Gln
545                 550                 555                 560

Pro Pro Ala Ala Asn Gln Leu Ile Thr Leu Ser Asn Leu His Leu Ser
                565                 570                 575

Leu Ser Ser Leu Leu Ala Asn Asn Ala Val Thr Asn Pro Pro Thr Asn
            580                 585                 590

Pro Pro Ala Gln Asp Ser His Pro Ala Val Ile Gly Ser Thr Thr Ala
        595                 600                 605

Gly Pro Val Thr Ile Ser Gly Pro Phe Phe Phe Glu Asp Leu Asp Asp
610                 615                 620

Thr Ala Tyr Asp Arg Tyr Asp Trp Leu Gly Ser Asn Gln Lys Ile Asp
625                 630                 635                 640

Val Leu Lys Leu Gln Leu Gly Thr Gln Pro Ser Ala Asn Ala Pro Ser
                645                 650                 655

Asp Leu Thr Leu Gly Asn Glu Met Pro Lys Tyr Gly Tyr Gln Gly Ser
            660                 665                 670

Trp Lys Leu Ala Trp Asp Pro Asn Thr Ala Asn Asn Gly Pro Tyr Thr
        675                 680                 685

Leu Lys Ala Thr Trp Thr Lys Thr Gly Tyr Asn Pro Gly Pro Glu Arg
    690                 695                 700

Val Ala Ser Leu Val Pro Asn Ser Leu Trp Gly Ser Ile Leu Asp Ile
705                 710                 715                 720

Arg Ser Ala His Ser Ala Ile Gln Ala Ser Val Asp Gly Arg Ser Tyr
                725                 730                 735

Cys Arg Gly Leu Trp Val Ser Gly Val Ser Asn Phe Ser Tyr His Asp
            740                 745                 750

Arg Asp Ala Leu Gly Gln Gly Tyr Arg Tyr Ile Ser Gly Gly Tyr Ser
        755                 760                 765

Leu Gly Ala Asn Ser Tyr Phe Gly Ser Ser Met Phe Gly Leu Ala Phe
    770                 775                 780

Thr Glu Val Phe Gly Arg Ser Lys Asp Tyr Val Val Cys Arg Ser Asn
785                 790                 795                 800

His His Ala Cys Ile Gly Ser Val Tyr Leu Ser Thr Lys Gln Ala Leu
                805                 810                 815

Cys Gly Ser Tyr Leu Phe Gly Asp Ala Phe Ile Arg Ala Ser Tyr Gly
            820                 825                 830

Phe Gly Asn Gln His Met Lys Thr Ser Tyr Thr Phe Ala Glu Glu Ser
        835                 840                 845

Asp Val Arg Trp Asp Asn Asn Cys Leu Val Gly Glu Ile Gly Val Gly
    850                 855                 860

Leu Pro Ile Val Thr Thr Pro Ser Lys Leu Tyr Leu Asn Glu Leu Arg
865                 870                 875                 880
```

-continued

```
Pro Phe Val Gln Ala Glu Phe Ser Tyr Ala Asp His Glu Ser Phe Thr
                885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
        915                 920                 925

Pro Asn Lys Tyr Ser Phe Met Gly Ala Tyr Ile Cys Asp Ala Tyr Arg
    930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser  Arg Gly Tyr Gly Leu  Ser Ala Gly
        995                 1000                 1005

Ser Lys  Val Arg Phe
    1010

<210> SEQ ID NO 17
<211> LENGTH: 505
<212> TYPE: PRT
<213> ORGANISM: Chlamydia sp.

<400> SEQUENCE: 17

Glu Ile Met Val Pro Gln Gly Ile Tyr Asp Gly Glu Thr Leu Thr Val
1               5                   10                  15

Ser Phe Pro Tyr Thr Val Ile Gly Asp Pro Ser Gly Thr Thr Val Phe
            20                  25                  30

Ser Ala Gly Glu Leu Thr Leu Lys Asn Leu Asp Asn Ser Ile Ala Ala
        35                  40                  45

Leu Pro Leu Ser Cys Phe Gly Asn Leu Leu Gly Ser Phe Thr Val Leu
    50                  55                  60

Gly Arg Gly His Ser Leu Thr Phe Glu Asn Ile Arg Thr Ser Thr Asn
65                  70                  75                  80

Gly Ala Ala Leu Ser Asn Ser Ala Ala Asp Gly Leu Phe Thr Ile Glu
                85                  90                  95

Gly Phe Lys Glu Leu Ser Phe Ser Asn Cys Asn Ser Leu Leu Ala Val
            100                 105                 110

Leu Pro Ala Ala Thr Thr Asn Lys Gly Ser Gln Thr Pro Thr Thr Thr
        115                 120                 125

Ser Thr Pro Ser Asn Gly Thr Ile Tyr Ser Lys Thr Asp Leu Leu Leu
    130                 135                 140

Leu Asn Asn Glu Lys Phe Ser Phe Tyr Ser Asn Leu Val Ser Gly Asp
145                 150                 155                 160

Gly Gly Ala Ile Asp Ala Lys Ser Leu Thr Val Gln Gly Ile Ser Lys
                165                 170                 175

Leu Cys Val Phe Gln Glu Asn Thr Ala Gln Ala Asp Gly Gly Ala Cys
            180                 185                 190

Gln Val Val Thr Ser Phe Ser Ala Met Ala Asn Glu Ala Pro Ile Ala
        195                 200                 205

Phe Val Ala Asn Val Ala Gly Val Arg Gly Gly Ile Ala Ala Val
    210                 215                 220

Gln Asp Gly Gln Gln Gly Val Ser Ser Ser Thr Ser Thr Glu Asp Pro
225                 230                 235                 240
```

```
Val Val Ser Phe Ser Arg Asn Thr Ala Val Glu Phe Asp Gly Asn Val
                245                 250                 255
Ala Arg Val Gly Gly Gly Ile Tyr Ser Tyr Gly Asn Val Ala Phe Leu
            260                 265                 270
Asn Asn Gly Lys Thr Leu Phe Leu Asn Asn Val Ala Ser Pro Val Tyr
        275                 280                 285
Ile Ala Ala Lys Gln Pro Thr Ser Gly Gln Ala Ser Asn Thr Ser Asn
    290                 295                 300
Asn Tyr Gly Asp Gly Gly Ala Ile Phe Cys Lys Asn Gly Ala Gln Ala
305                 310                 315                 320
Gly Ser Asn Asn Ser Gly Ser Val Ser Phe Asp Gly Glu Gly Val Val
                325                 330                 335
Phe Phe Ser Ser Asn Val Ala Ala Gly Lys Gly Ala Ile Tyr Ala
            340                 345                 350
Lys Lys Leu Ser Val Ala Asn Cys Gly Pro Val Gln Phe Leu Arg Asn
        355                 360                 365
Ile Ala Asn Asp Gly Gly Ala Ile Tyr Leu Gly Glu Ser Gly Glu Leu
    370                 375                 380
Ser Leu Ser Ala Asp Tyr Gly Asp Ile Ile Phe Asp Gly Asn Leu Lys
385                 390                 395                 400
Arg Thr Ala Lys Glu Asn Ala Ala Asp Val Asn Gly Val Thr Val Ser
                405                 410                 415
Ser Gln Ala Ile Ser Met Gly Ser Gly Gly Lys Ile Thr Thr Leu Arg
            420                 425                 430
Ala Lys Ala Gly His Gln Ile Leu Phe Asn Asp Pro Ile Glu Met Ala
        435                 440                 445
Asn Gly Asn Asn Gln Pro Ala Gln Ser Ser Lys Leu Leu Lys Ile Asn
    450                 455                 460
Asp Gly Glu Gly Tyr Thr Gly Asp Ile Val Phe Ala Asn Gly Ser Ser
465                 470                 475                 480
Thr Leu Tyr Gln Asn Val Thr Ile Glu Gln Gly Arg Ile Val Leu Arg
                485                 490                 495
Glu Lys Ala Lys Leu Ser Val Asn Ser
            500                 505

<210> SEQ ID NO 18
<211> LENGTH: 57
<212> TYPE: DNA
<213> ORGANISM: Chlamydia sp.

<400> SEQUENCE: 18
aagggcccaa ttacgcagag ctcgagagaa attatggttc ctcaaggaat ttacgat      57

<210> SEQ ID NO 19
<211> LENGTH: 20
<212> TYPE: DNA
<213> ORGANISM: Chlamydia sp.

<400> SEQUENCE: 19
cgctctagaa ctagtggatc                                               20

<210> SEQ ID NO 20
<211> LENGTH: 22
<212> TYPE: DNA
<213> ORGANISM: Chlamydia sp.

<400> SEQUENCE: 20
```

-continued

| atggttcctc aaggaattta cg | 22 |

```
<210> SEQ ID NO 21
<211> LENGTH: 19
<212> TYPE: DNA
<213> ORGANISM: Chlamydia sp.

<400> SEQUENCE: 21
```

| ggtcccccat cagcgggag | 19 |

```
<210> SEQ ID NO 22
<211> LENGTH: 1515
<212> TYPE: DNA
<213> ORGANISM: Chlamydia sp.

<400> SEQUENCE: 22
```

| gaaatcatgg ttcctcaagg aatttacgat ggggagacgt taactgtatc atttccctat | 60 |
| actgttatag gagatccgag tgggactact gttttttctg caggagagtt aacattaaaa | 120 |
| aatcttgaca attctattgc agctttgcct taagttgtt ttgggaactt attagggagt | 180 |
| tttactgttt tagggagagg acactcgttg actttcgaga acatacggac ttctacaaat | 240 |
| ggggcagctc taagtaatag cgctgctgat ggactgttta ctattgaggg ttttaaagaa | 300 |
| ttatcctttt ccaattgcaa ttcattactt gccgtactgc ctgctgcaac gactaataag | 360 |
| ggtagccaga ctccgacgac aacatctaca ccgtctaatg gtactattta ttctaaaaca | 420 |
| gatcttttgt tactcaataa tgagaagttc tcattctata gtaatttagt ctctggagat | 480 |
| gggggagcta tagatgctaa gagcttaacg gttcaaggaa ttagcaagct ttgtgtcttc | 540 |
| caagaaaata ctgctcaagc tgatggggga gcttgtcaag tagtcaccag tttctctgct | 600 |
| atggctaacg aggctcctat tgcctttgta gcgaatgttg caggagtaag agggggaggg | 660 |
| attgctgctg ttcaggatgg gcagcaggga gtgtcatcat ctacttcaac agaagatcca | 720 |
| gtagtaagtt tttccagaaa tactgcggta gagtttgatg ggaacgtagc ccgagtagga | 780 |
| ggagggattt actcctacgg gaacgttgct ttcctgaata atggaaaaac cttgtttctc | 840 |
| aacaatgttg cttctcctgt ttacattgct gctaagcaac caacaagtgg acaggcttct | 900 |
| aatacgagta ataattacgg agatggagga gctatcttct gtaagaatgg tgcgcaagca | 960 |
| ggatccaata actctggatc agtttccttt gatggagagg gagtagtttt ctttagtagc | 1020 |
| aatgtagctg ctgggaaagg gggagctatt tatgccaaaa agctctcggt tgctaactgt | 1080 |
| ggccctgtac aatttttaag gaatatcgct aatgatggtg gagcgattta tttaggagaa | 1140 |
| tctggagagc tcagtttatc tgctgattat ggagatatta ttttcgatgg gaatcttaaa | 1200 |
| agaacagcca aagagaatgc tgccgatgtt aatggcgtaa ctgtgtcctc acaagccatt | 1260 |
| tcgatgggat cggagggaa ataacgaca ttaagagcta agcagggca tcagattctc | 1320 |
| tttaatgatc ccatcgagat ggcaaacgga aataaccagc cagcgcagtc ttccaaactt | 1380 |
| ctaaaaatta cgatggtga aggatacaca ggggatattg tttttgctaa tggaagcagt | 1440 |
| actttgtacc aaaatgttac gatagagcaa ggaaggattg ttcttcgtga aaaggcaaaa | 1500 |
| ttatcagtga attct | 1515 |

```
<210> SEQ ID NO 23
<211> LENGTH: 3354
<212> TYPE: DNA
<213> ORGANISM: Artificial Sequence
<220> FEATURE:
```

<223> OTHER INFORMATION: Description of Artificial Sequence: Recombinant Expression Vector

<400> SEQUENCE: 23

| | | | | | |
|---|---|---|---|---|---|
| atgcaaacgt | ctttccataa | gttctttctt | tcaatgattc | tagcttattc | ttgctgctct | 60 |
| ttaaatgggg | ggggtatgc | agaaatcatg | ttcctcaag | gaatttacga | tggggagacg | 120 |
| ttaactgtat | catttcccta | tactgttata | ggagatccga | gtgggactac | tgttttttct | 180 |
| gcaggagagt | taacgttaaa | aaatcttgac | aattctattg | cagctttgcc | tttaagttgt | 240 |
| tttgggaact | tattagggag | ttttactgtt | ttagggagag | gacactcgtt | gactttcgag | 300 |
| aacatacgga | cttctacaaa | tggagctgca | ctaagtgaca | gcgctaatag | cgggttattt | 360 |
| actattgagg | gttttaaaga | attatctttt | tccaattgca | acccattact | tgccgtactg | 420 |
| cctgctgcaa | cgactaataa | tggtagccag | actccgtcga | caacatctac | accgtctaat | 480 |
| ggtactattt | attctaaaac | agatcttttg | ttactcaata | atgagaagtt | ctcattctat | 540 |
| agtaattcag | tctctggaga | tgggggagct | atagatgcta | agagcttaac | ggttcaagga | 600 |
| attagcaagc | tttgtgtctt | ccaagaaaat | actgctcaag | ctgatggggg | agcttgtcaa | 660 |
| gtagtcacca | gtttctctgc | tatggctaac | gaggctccta | ttgcctttgt | agcgaatgtt | 720 |
| gcaggagtaa | gagggggagg | gattgctgct | gttcaggatg | ggcagcaggg | agtgtcatca | 780 |
| tctacttcaa | cagaagatcc | agtagtaagt | ttttccagaa | atactgcggt | agagtttgat | 840 |
| gggaacgtag | cccgagtagg | aggagggatt | tactcctacg | ggaacgttgc | tttcctgaat | 900 |
| aatgaaaaaa | ccttgtttct | caacaatgtt | gcttctcctg | tttacattgc | tgctgagcaa | 960 |
| ccaacaaatg | gacaggcttc | taatacgagt | gataattacg | gagatggagg | agctatcttc | 1020 |
| tgtaagaatg | gtgcgcaagc | agcaggatcc | aataactctg | gatcagtttc | ctttgatgga | 1080 |
| gagggagtag | ttttctttag | tagcaatgta | gctgctggga | aaggggagc | tatttatgcc | 1140 |
| aaaaagctct | cggttgctaa | ctgtggcct | gtacaactct | tagggaatat | cgctaatgat | 1200 |
| ggtggagcga | tttatttagg | agaatctgga | gagctcagtt | tatctgctga | ttatggagat | 1260 |
| atgattttcg | atgggaatct | taaaagaaca | gccaaagaga | atgctgccga | tgttaatggc | 1320 |
| gtaactgtgt | cctcacaagc | catttcgatg | ggatcgggag | ggaaaataac | gacattaaga | 1380 |
| gctaaagcag | ggcatcagat | tctctttaat | gatcccatcg | agatggcaaa | cggaaataac | 1440 |
| cagccagcgc | agtcttccga | acctctaaaa | attaacgatg | gtgaaggata | cacaggggat | 1500 |
| attgttttg | ctaatggaaa | cagtactttg | taccaaaatg | ttacgataga | gcaaggaagg | 1560 |
| attgttcttc | gtgaaaaggc | aaaattatca | gtgaattctc | taagtcagac | aggtgggagt | 1620 |
| ctgtatatgg | aagctgggag | tacattggat | tttgtaactc | cacaaccacc | acaacagcct | 1680 |
| cctgccgcta | atcagtcgat | cacgctttcc | aatctgcatt | tgtctctttc | ttctttgtta | 1740 |
| gcaaacaatg | cagttacgaa | tcctcctacc | aatcctccag | cgcaagattc | tcatcctgca | 1800 |
| gtcattggta | gcacaactgc | tggttctgtt | acaattagtg | ggcctatctt | ttttgaggat | 1860 |
| ttggatgata | cagcttatga | taggtatgat | tggctaggtt | ctaatcaaaa | aatcgatgtc | 1920 |
| ctgaaattac | agttagggac | tcagccccca | gctaatgccc | catcagattt | gactctaggg | 1980 |
| aatgagatgc | ctaagtatgg | ctatcaagga | agctggaagc | ttgcgtggga | tcctaataca | 2040 |
| gcaaataatg | gtccttatac | tctgaaagct | acatggacta | aaactgggta | taatcctggg | 2100 |
| cctgagcgag | tagcttcttt | ggttccaaat | agtttatggg | gatccatttt | agatatacga | 2160 |
| tctgcgcatt | cagcaattca | agcaagtgtg | gatgggcgct | cttattgtcg | aggattatgg | 2220 |

-continued

```
gtttctggag tttcgaattt cttctatcat gaccgcgatg ctttaggtca gggatatcgg      2280
tatattagtg ggggttattc cttaggagca aactcctact ttggatcatc gatgtttggt      2340
ctagcattta ctgaagtatt tggtagatct aaagattatg tagtgtgtcg ttccaatcat      2400
catgcttgca taggatccgt ttatctatct accaaacagg ctttatgtgg atcttatgtg      2460
tttggagatg cgtttattcg tgctagctac gggtttggga atcagcatat gaaaacctca      2520
tatacatttg cagaggagag cgatgtttgt tgggataata actgtctggt tggagagatt      2580
ggagtgggat taccgattgt gattactcca tctaagctct atttgaatga gttgcgtcct      2640
ttcgtgcaag ctgagttttc ttatgccgat catgaatctt ttacagagga aggcgatcaa      2700
gctcgggcat tcaggagtgg acatctcatg aatctatcag ttcctgttgg agtaaaattt      2760
gatcgatgtt ctagtacaca ccctaataaa tatagcttta tggggcttat atctgtgat       2820 gcttatcgca ccatctctgg gactcagaca acactcctat cccatcaaga gacatggaca      2880
acagatgcct tcatttggc aagacatgga gtcatagtta gaggtctat gtatgcttct        2940 ctaacaagca atatagaagt atatggccat ggaagatatg agtatcgaga tacttctcga      3000
ggttatggtt tgagtgcagg aagtaaagtc cggttctaaa aatattggtt agatagttaa      3060
gtgttagcga tgccttttc tttgagatct acatcatttt gttttttagc ttgtttgtgt       3120
tcctattcgt atggattcgc gagctctcct caagtgttaa cacctaatgt aaccactcct      3180 tttaagggg acgatgttta cttgaatgga gactgcgctt ttgtcaatgt ctatgcaggg      3240
gcagagaacg gctcaattat ctcagctaat ggcgacaatt taacgattac cggacaaaac      3300
catacattat catttacaca ttctcaaggg ccagttcttc aaaattagcc ttca            3354
```

<210> SEQ ID NO 24
<211> LENGTH: 3324
<212> TYPE: DNA
<213> ORGANISM: Artificial Sequence
<220> FEATURE:
<223> OTHER INFORMATION: Description of Artificial Sequence: Recombinant Expression Vector

<400> SEQUENCE: 24

```
atgcaaacgt ctttccataa gttctttctt tcaatgattc tagcttattc ttgctgctct       60
ttaagtgggg gggggtatgc agcagaaatc atgattcctc aaggaattta cgatggggag      120
acgttaactg tatcatttcc ctatactgtt ataggagatc cgagtgggac tactgttttt      180
tctgcaggag agttaacgtt aaaaaatctt gacaattcta ttgcagcttt gcctttaagt     240
tgttttggga acttattagg gagttttact gttttaggga gggacactc gttgactttc      300 gagaacatac ggacttctac aaatggagct gcactaagtg acagcgctaa tagcgggtta     360
tttactattg agggttttaa agaattatct ttttccaatt gcaactcatt acttgccgta     420
ctgcctgctg caacgactaa taatggtagc cagactccga cgacaacatc tacaccgtct    480
aatggtacta tttattctaa aacagatctt ttgttactca ataatgagaa gttctcattc     540
tatagtaatt tagtctctgg agatggggga actatagatg ctaagagctt aacggttcaa     600
ggaattagca agctttgtgt cttccaagaa atactgctc aagctgatgg gggagcttgt      660
caagtagtca ccagtttctc tgctatggct aacgaggctc ctattgcctt tatagcgaat     720
gttgcaggag taagaggggg agggattgct gctgttcagg atgggcagca gggagtgtca     780
tcatctactt caacagaaga tccagtagta agttttttcca gaaatactgc ggtagagttt    840
gatgggaacg tagcccgagt aggaggaggg atttactcct acgggaacgt tgctttcctg     900
```

```
aataatggaa aaaccttgtt tctcaacaat gttgcttctc ctgtttacat tgctgctgag    960
caaccaacaa atggacaggc ttctaatacg agtgataatt acggagatgg aggagctatc   1020
ttctgtaaga atggtgcgca agcagcagga tccaataact ctggatcagt ttcctttgat   1080
ggagagggag tagttttctt tagtagcaat gtagctgctg ggaaaggggg agctatttat   1140
gccaaaaagc tctcggttgc taactgtggc cctgtacaat tcttagggaa tatcgctaat   1200
gatggtggag cgatttattt aggagaatct ggagagctca gtttatctgc tgattatgga   1260
gatattattt tcgatgggaa tcttaaaaga acagccaaag agaatgctgc cgatgttaat   1320
ggcgtaactg tgtcctcaca agccatttcg atgggatcgg gagggaaaat aacgacatta   1380
agagctaaag cagggcatca gattctcttt aatgatccca tcgagatggc aaacggaaat   1440
aaccagccag cgcagtcttc cgaacctcta aaaattaacg atggtgaagg atacacaggg   1500
gatattgttt ttgctaatgg aaacagtact ttgtaccaaa atgttacgat agagcaagga   1560
aggattgttc ttcgtgaaaa ggcaaaatta tcagtgaatt ctctaagtca gacaggtggg   1620
agtctgtata tggaagctgg gagtacattg gattttgtaa ctccacaacc accacaacag   1680
cctcctgccg ctaatcagtt gatcacgctt tccaatctgc atttgtctct ttcttctttg   1740
ttagcaaaca atgcagttac gaatcctcct accaatcctc cagcgcaaga ttctcatcct   1800
gcagtcattg gtagcacaac tgctggtcct gtcacaatta gtgggccttt cttttttgag   1860
gatttggatg atacagctta tgataggtat gattggctag gttctaatca aaaaatcgat   1920
gtcctgaaat tacagttagg gactcagccc tcagctaatg ccccatcaga tttgactcta   1980
gggaatgaga tgcctaagta tggctatcaa ggaagctgga agcttgcgtg ggatcctaat   2040
acagcaaata atggtcctta tactctgaaa gctacatgga ctaaaactgg gtataatcct   2100
gggcctgagc gagtagcttc tttggttcca aatagtttat ggggatccat tttagatata   2160
cgatctgcgc attcagcaat tcaagcaagt gtggatgggc gctcttattg tcgaggatta   2220
tgggtttctg gagtttcgaa tttctcctat catgaccgcg atgctttagg tcagggatat   2280
cggtatatta gtgggggtta ttccttagga gcaaactcct actttggatc atcgatgttt   2340
ggtctagcat ttaccgaagt atttggtaga tctaaagatt atgtagtgtg tcgttccaat   2400
catcatgctt gcataggatc cgtttatcta tctaccaaac aagctttatg tggatcctat   2460
ttgttcggag atgcgtttat ccgtgctagc tacgggtttg ggaaccagca tatgaaaacc   2520
tcatacacat ttgcagagga gagcgatgtt cgttgggata taactgtctg gttggagag   2580 attggagtgg gattaccgat tgtgactact ccatctaagc tctatttgaa tgagttgcgt   2640
cctttcgtgc aagctgagtt ttcttatgcc gatcatgaat cttttacaga ggaaggcgat   2700
caagctcggg cattcaggag tggtcatctc atgaatctat cagttcctgt tggagtaaaa   2760
tttgatcgat gttctagtac acaccctaat aaatatagct ttatggggc ttatatctgt   2820 gatgcttatc gcaccatctc tgggactcag acaaacactcc tatcccatca agagacatgg   2880
acaacagatg cctttcattt ggcaagacat ggagtcatag ttagagggtc tatgtatgct   2940
tctctaacaa gcaatataga agtatatggc catggaagat atgagtatcg agatacttct   3000
cgaggttatg gtttgagtgc aggaagtaaa gtccggttct aaaaatattg gttagatagt   3060
taagtgttag cgatgccttt ttcttttgaga tctacatcat tttgtttttt agcttgtttg   3120
tgttcctatt cgtatggatt cgcgagctct cctcaagtgt taacacctaa tgtaaccact   3180
ccttttaagg gggacgatgt ttacttgaat ggagactgcg ctttagtcaa tgtctatgca   3240
ggggcagaga acggctcaat tatctcagct aatggcgaca atttaacgat taccggacaa   3300
```

```
aaccatgcat tatcatttac agat                                           3324
```

<210> SEQ ID NO 25
<211> LENGTH: 65
<212> TYPE: PRT
<213> ORGANISM: Chlamydia sp.

<400> SEQUENCE: 25

```
Pro Tyr Thr Val Ile Gly Asp Pro Ser Gly Thr Thr Val Phe Ser Ala
1               5                   10                  15

Gly Glu Leu Thr Leu Lys Asn Leu Asp Asn Ser Ile Ala Ala Pro Leu
            20                  25                  30

Ser Cys Phe Gly Asn Leu Leu Gly Ser Phe Thr Val Leu Gly Arg Gly
        35                  40                  45

His Ser Leu Thr Phe Glu Asn Ile Arg Thr Ser Thr Asn Gly Ala Ala
    50                  55                  60

Leu
65
```

<210> SEQ ID NO 26
<211> LENGTH: 24
<212> TYPE: PRT
<213> ORGANISM: Chlamydia sp.

<400> SEQUENCE: 26

```
Ala Ala Asn Gln Leu Ile Thr Leu Ser Asn Leu His Leu Ser Leu Ser
1               5                   10                  15

Ser Leu Leu Ala Asn Asn Ala Val
            20
```

<210> SEQ ID NO 27
<211> LENGTH: 8
<212> TYPE: PRT
<213> ORGANISM: Chlamydia sp.

<400> SEQUENCE: 27

```
Gly Tyr Thr Gly Asp Ile Val Phe
1               5
```

<210> SEQ ID NO 28
<211> LENGTH: 7
<212> TYPE: PRT
<213> ORGANISM: Chlamydia sp.

<400> SEQUENCE: 28

```
Tyr Gly Asp Ile Ile Phe Asp
1               5
```

<210> SEQ ID NO 29
<211> LENGTH: 63
<212> TYPE: PRT
<213> ORGANISM: Chlamydia sp.

<400> SEQUENCE: 29

```
Gly Tyr Ala Ala Glu Ile Met Val Pro Gln Gly Ile Tyr Asp Gly Glu
1               5                   10                  15

Thr Leu Thr Val Ser Phe Pro Tyr Thr Val Ile Gly Asp Pro Ser Gly
            20                  25                  30

Thr Thr Val Phe Ser Ala Gly Glu Leu Thr Leu Lys Asn Leu Asp Asn
        35                  40                  45
```

-continued

Ser Ile Ala Ala Leu Pro Leu Ser Cys Phe Gly Asn Leu Leu Gly
    50                  55                  60

<210> SEQ ID NO 30
<211> LENGTH: 22
<212> TYPE: PRT
<213> ORGANISM: Chlamydia sp.

<400> SEQUENCE: 30

Met Ala Asn Gly Asn Asn Gln Pro Ala Gln Ser Ser Lys Leu Leu Lys
1               5                   10                  15

Ile Asn Asp Gly Glu Gly
            20

<210> SEQ ID NO 31
<211> LENGTH: 14
<212> TYPE: PRT
<213> ORGANISM: Chlamydia sp.

<400> SEQUENCE: 31

Ala Asn Gly Ser Ser Thr Leu Tyr Gln Asn Val Thr Ile Glu
1               5                   10

<210> SEQ ID NO 32
<211> LENGTH: 10
<212> TYPE: PRT
<213> ORGANISM: Chlamydia sp.

<400> SEQUENCE: 32

Lys Leu Ser Val Asn Ser Leu Ser Gln Thr
1               5                   10

<210> SEQ ID NO 33
<211> LENGTH: 45
<212> TYPE: PRT
<213> ORGANISM: Chlamydia sp.

<400> SEQUENCE: 33

Val Ile Gly Ser Thr Thr Ala Gly Ser Val Thr Ile Ser Gly Pro Ile
1               5                   10                  15

Phe Phe Glu Asp Leu Asp Asp Thr Ala Tyr Asp Arg Tyr Asp Trp Leu
            20                  25                  30

Gly Ser Asn Gln Lys Ile Asn Val Leu Lys Leu Gln Leu
        35                  40                  45

<210> SEQ ID NO 34
<211> LENGTH: 64
<212> TYPE: PRT
<213> ORGANISM: Chlamydia sp.

<400> SEQUENCE: 34

Val Ile Gly Ser Thr Thr Ala Gly Ser Val Thr Ile Ser Gly Pro Ile
1               5                   10                  15

Phe Phe Glu Asp Leu Asp Asp Thr Ala Tyr Asp Arg Tyr Asp Trp Leu
            20                  25                  30

Gly Ser Asn Gln Lys Ile Asn Val Leu Lys Leu Gln Leu Gly Thr Lys
        35                  40                  45

Pro Pro Ala Asn Ala Pro Ser Asp Leu Thr Leu Gly Asn Glu Met Pro
    50                  55                  60

<210> SEQ ID NO 35
<211> LENGTH: 10

```
<212> TYPE: PRT
<213> ORGANISM: Chlamydia sp.

<400> SEQUENCE: 35

Asp Pro Asn Thr Ala Asn Asn Gly Pro Tyr
1               5                   10

<210> SEQ ID NO 36
<211> LENGTH: 458
<212> TYPE: PRT
<213> ORGANISM: Chlamydia sp.

<400> SEQUENCE: 36

Gly Gly Ala Cys Gln Val Val Thr Ser Phe Ser Ala Met Ala Asn Glu
1               5                   10                  15

Ala Pro Ile Ala Phe Val Ala Asn Val Ala Gly Val Arg Gly Gly Gly
                20                  25                  30

Ile Ala Ala Val Gln Asp Gly Gln Gln Gly Val Ser Ser Ser Thr Ser
            35                  40                  45

Thr Glu Asp Pro Val Val Ser Phe Ser Arg Asn Thr Ala Val Glu Phe
    50                  55                  60

Asp Gly Asn Val Ala Arg Val Gly Gly Gly Ile Tyr Ser Tyr Gly Asn
65                  70                  75                  80

Val Ala Phe Leu Asn Asn Gly Lys Thr Leu Phe Leu Asn Asn Val Ala
                85                  90                  95

Ser Pro Val Tyr Ile Ala Ala Lys Gln Pro Thr Ser Gly Gln Ala Ser
                100                 105                 110

Asn Thr Ser Asn Asn Tyr Gly Asp Gly Gly Ala Ile Phe Cys Lys Asn
            115                 120                 125

Gly Ala Gln Ala Gly Ser Asn Asn Ser Gly Ser Val Ser Phe Asp Gly
    130                 135                 140

Glu Gly Val Val Phe Phe Ser Ser Asn Val Ala Ala Gly Lys Gly Gly
145                 150                 155                 160

Ala Ile Tyr Ala Lys Lys Leu Ser Val Ala Asn Cys Gly Pro Val Gln
                165                 170                 175

Phe Leu Arg Asn Ile Ala Asn Asp Gly Gly Ala Ile Tyr Leu Gly Glu
                180                 185                 190

Ser Gly Glu Leu Ser Leu Ser Ala Asp Tyr Gly Asp Ile Ile Phe Asp
            195                 200                 205

Gly Asn Leu Lys Arg Thr Ala Lys Glu Asn Ala Ala Asp Val Asn Gly
    210                 215                 220

Val Thr Val Ser Ser Gln Ala Ile Ser Met Gly Ser Gly Lys Ile
225                 230                 235                 240

Thr Thr Leu Arg Ala Lys Ala Gly His Gln Ile Leu Phe Asn Asp Pro
                245                 250                 255

Ile Glu Met Ala Asn Gly Asn Asn Gln Pro Ala Gln Ser Ser Lys Leu
                260                 265                 270

Leu Lys Ile Asn Asp Gly Glu Gly Tyr Thr Gly Asp Ile Val Phe Ala
            275                 280                 285

Asn Gly Ser Ser Thr Leu Tyr Gln Asn Val Thr Ile Glu Gln Gly Arg
    290                 295                 300

Ile Val Leu Arg Glu Lys Ala Lys Leu Ser Val Asn Ser Leu Ser Gln
305                 310                 315                 320

Thr Gly Gly Ser Leu Tyr Met Glu Ala Gly Ser Thr Trp Asp Phe Val
                325                 330                 335
```

-continued

```
Thr Pro Gln Pro Pro Gln Gln Pro Pro Ala Ala Asn Gln Leu Ile Thr
        340                 345                 350

Leu Ser Asn Leu His Leu Ser Leu Ser Ser Leu Leu Ala Asn Asn Ala
        355                 360                 365

Val Thr Asn Pro Pro Thr Asn Pro Pro Ala Gln Asp Ser His Pro Ala
370                 375                 380

Val Ile Gly Ser Thr Thr Ala Gly Ser Val Thr Ile Ser Gly Pro Ile
385                 390                 395                 400

Phe Phe Glu Asp Leu Asp Asp Thr Ala Tyr Asp Arg Tyr Asp Trp Leu
                405                 410                 415

Gly Ser Asn Gln Lys Ile Asn Val Leu Lys Leu Gln Leu Gly Thr Lys
                420                 425                 430

Pro Pro Ala Asn Ala Pro Ser Asp Leu Thr Leu Gly Asn Glu Met Pro
                435                 440                 445

Lys Tyr Gly Tyr Gln Gly Ser Trp Lys Leu
        450                 455
```

<210> SEQ ID NO 37
<211> LENGTH: 325
<212> TYPE: PRT
<213> ORGANISM: Chlamydia sp.

<400> SEQUENCE: 37

```
Leu Lys Ala Thr Trp Thr Lys Thr Gly Tyr Asn Pro Gly Pro Glu Arg
  1               5                  10                  15

Val Ala Ser Leu Val Pro Asn Ser Leu Trp Gly Ser Ile Leu Asp Ile
                 20                  25                  30

Arg Ser Ala His Ser Ala Ile Gln Ala Ser Val Asp Gly Arg Ser Tyr
             35                  40                  45

Cys Arg Gly Leu Trp Val Ser Gly Val Ser Asn Phe Tyr His Asp
         50                  55                  60

Arg Asp Ala Leu Gly Gln Gly Tyr Arg Tyr Ile Ser Gly Gly Tyr Ser
 65                  70                  75                  80

Leu Gly Ala Asn Ser Tyr Phe Gly Ser Ser Met Phe Gly Leu Ala Phe
                 85                  90                  95

Thr Glu Val Phe Gly Arg Ser Lys Asp Tyr Val Val Cys Arg Ser Asn
                100                 105                 110

His His Ala Cys Ile Gly Ser Val Tyr Leu Ser Thr Gln Gln Ala Leu
            115                 120                 125

Cys Gly Ser Tyr Leu Phe Gly Asp Ala Phe Ile Arg Ala Ser Tyr Gly
        130                 135                 140

Phe Gly Asn Gln His Met Lys Thr Ser Tyr Thr Phe Ala Glu Glu Ser
145                 150                 155                 160

Asp Val Arg Trp Asp Asn Asn Cys Leu Ala Gly Glu Ile Gly Ala Gly
                165                 170                 175

Leu Pro Ile Val Ile Thr Pro Ser Lys Leu Tyr Leu Asn Glu Leu Arg
                180                 185                 190

Pro Phe Val Gln Ala Glu Phe Ser Tyr Ala Asp His Glu Ser Phe Thr
            195                 200                 205

Glu Glu Gly Asp Gln Ala Arg Ala Phe Lys Ser Gly His Leu Leu Asn
        210                 215                 220

Leu Ser Val Pro Val Gly Val Lys Phe Asp Arg Cys Ser Ser Thr His
225                 230                 235                 240

Pro Asn Lys Tyr Ser Phe Met Ala Ala Tyr Ile Cys Asp Ala Tyr Arg
                245                 250                 255
```

```
Thr Ile Ser Gly Thr Glu Thr Thr Leu Leu Ser His Gln Glu Thr Trp
        260                 265                 270

Thr Thr Asp Ala Phe His Leu Ala Arg His Gly Val Val Arg Gly
    275                 280                 285

Ser Met Tyr Ala Ser Leu Thr Ser Asn Ile Glu Val Tyr Gly His Gly
    290                 295                 300

Arg Tyr Glu Tyr Arg Asp Ala Ser Arg Gly Tyr Gly Leu Ser Ala Gly
305                 310                 315                 320

Ser Arg Val Arg Phe
                325

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 38
gggtttggga atcagcacat gaaaacctca tatacatttg c                41

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 39
gcaaatgtat atgaggtttt catgtgctga ttcccaaacc c                41

<210> SEQ ID NO 40
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 40
aagggcccaa ttacgcagac atatggaaac gtctttccat aagttctttc tttca    55

<210> SEQ ID NO 41
<211> LENGTH: 80
<212> TYPE: DNA
<213> ORGANISM: Artificial Sequence
<220> FEATURE:
<223> OTHER INFORMATION: Description of Artificial Sequence: primer

<400> SEQUENCE: 41
aagggcccaa ttacgcagag tctagattat taatgatgat gatgatgatg gaaccggact    60
ctacttcctg cactcaaacc                                                80

<210> SEQ ID NO 42
<211> LENGTH: 6
<212> TYPE: PRT
<213> ORGANISM: Chlamydia sp.

<400> SEQUENCE: 42

Glu Ile Met Val Pro Gln
1               5

<210> SEQ ID NO 43
```

```
<211> LENGTH: 984
<212> TYPE: PRT
<213> ORGANISM: Chlamydia sp.

<400> SEQUENCE: 43
```

| | | | | | | | | | | | | | | | |
|---|---|---|---|---|---|---|---|---|---|---|---|---|---|---|---|
|Glu|Ile|Met|Val|Pro|Gln|Gly|Ile|Tyr|Asp|Gly|Glu|Thr|Leu|Thr|Val|
|1| | | |5| | | | |10| | | | |15| |
|Ser|Phe|Pro|Tyr|Thr|Val|Ile|Gly|Asp|Pro|Ser|Gly|Thr|Thr|Val|Phe|
| | | |20| | | | |25| | | | |30| | |
|Ser|Ala|Gly|Glu|Leu|Thr|Leu|Lys|Asn|Leu|Asp|Asn|Ser|Ile|Ala|Ala|
| | |35| | | | |40| | | | |45| | | |
|Leu|Pro|Leu|Ser|Cys|Phe|Gly|Asn|Leu|Leu|Gly|Ser|Phe|Thr|Val|Leu|
| |50| | | | |55| | | | |60| | | | |
|Gly|Arg|Gly|His|Ser|Leu|Thr|Phe|Glu|Asn|Ile|Arg|Thr|Ser|Thr|Asn|
|65| | | | |70| | | | |75| | | | |80|
|Gly|Ala|Ala|Leu|Ser|Asn|Ser|Ala|Ala|Asp|Gly|Leu|Phe|Thr|Ile|Glu|
| | | | |85| | | | |90| | | | |95| |
|Gly|Phe|Lys|Glu|Leu|Ser|Phe|Ser|Asn|Cys|Asn|Ser|Leu|Leu|Ala|Val|
| | | |100| | | | |105| | | | |110| | |
|Leu|Pro|Ala|Ala|Thr|Thr|Asn|Lys|Gly|Ser|Gln|Thr|Pro|Thr|Thr|Thr|
| | |115| | | | |120| | | | |125| | | |
|Ser|Thr|Pro|Ser|Asn|Gly|Thr|Ile|Tyr|Ser|Lys|Thr|Asp|Leu|Leu|Leu|
| |130| | | | |135| | | | |140| | | | |
|Leu|Asn|Asn|Glu|Lys|Phe|Ser|Phe|Tyr|Ser|Asn|Leu|Val|Ser|Gly|Asp|
|145| | | | |150| | | | |155| | | | |160|
|Gly|Gly|Ala|Ile|Asp|Ala|Lys|Ser|Leu|Thr|Val|Gln|Gly|Ile|Ser|Lys|
| | | | |165| | | | |170| | | | |175| |
|Leu|Cys|Val|Phe|Gln|Glu|Asn|Thr|Ala|Gln|Ala|Asp|Gly|Gly|Ala|Cys|
| | | |180| | | | |185| | | | |190| | |
|Gln|Val|Val|Thr|Ser|Phe|Ser|Ala|Met|Ala|Asn|Glu|Ala|Pro|Ile|Ala|
| | |195| | | | |200| | | | |205| | | |
|Phe|Val|Ala|Asn|Val|Ala|Gly|Val|Arg|Gly|Gly|Ile|Ala|Ala|Val|
| |210| | | | |215| | | | |220| | | | |
|Gln|Asp|Gly|Gln|Gln|Gly|Val|Ser|Ser|Ser|Thr|Ser|Thr|Glu|Asp|Pro|
|225| | | | |230| | | | |235| | | | |240|
|Val|Val|Ser|Phe|Ser|Arg|Asn|Thr|Ala|Val|Glu|Phe|Asp|Gly|Asn|Val|
| | | |245| | | | |250| | | | |255| | |
|Ala|Arg|Val|Gly|Gly|Gly|Ile|Tyr|Ser|Tyr|Gly|Asn|Val|Ala|Phe|Leu|
| | |260| | | | |265| | | | |270| | | |
|Asn|Asn|Gly|Lys|Thr|Leu|Phe|Leu|Asn|Asn|Val|Ala|Ser|Pro|Val|Tyr|
| |275| | | | |280| | | | |285| | | | |
|Ile|Ala|Ala|Lys|Gln|Pro|Thr|Ser|Gly|Gln|Ala|Ser|Asn|Thr|Ser|Asn|
|290| | | | |295| | | | |300| | | | | |
|Asn|Tyr|Gly|Asp|Gly|Gly|Ala|Ile|Phe|Cys|Lys|Asn|Gly|Ala|Gln|Ala|
|305| | | |310| | | | |315| | | | |320| |
|Gly|Ser|Asn|Asn|Ser|Gly|Ser|Val|Ser|Phe|Asp|Gly|Glu|Gly|Val|Val|
| | | |325| | | | |330| | | | |335| | |
|Phe|Phe|Ser|Ser|Asn|Val|Ala|Ala|Gly|Lys|Gly|Gly|Ala|Ile|Tyr|Ala|
| | |340| | | | |345| | | | |350| | | |
|Lys|Lys|Leu|Ser|Val|Ala|Asn|Cys|Gly|Pro|Val|Gln|Phe|Leu|Arg|Asn|
| |355| | | | |360| | | | |365| | | | |
|Ile|Ala|Asn|Asp|Gly|Gly|Ala|Ile|Tyr|Leu|Gly|Glu|Ser|Gly|Glu|Leu|
|370| | | | |375| | | | |380| | | | | |
|Ser|Leu|Ser|Ala|Asp|Tyr|Gly|Asp|Ile|Ile|Phe|Asp|Gly|Asn|Leu|Lys|

```
            385                 390                 395                 400
Arg Thr Ala Lys Glu Asn Ala Ala Asp Val Asn Gly Val Thr Val Ser
                405                 410                 415
Ser Gln Ala Ile Ser Met Gly Ser Gly Gly Lys Ile Thr Thr Leu Arg
                420                 425                 430
Ala Lys Ala Gly His Gln Ile Leu Phe Asn Asp Pro Ile Glu Met Ala
                435                 440                 445
Asn Gly Asn Asn Gln Pro Ala Gln Ser Ser Lys Leu Leu Lys Ile Asn
            450                 455                 460
Asp Gly Glu Gly Tyr Thr Gly Asp Ile Val Phe Ala Asn Gly Ser Ser
465                 470                 475                 480
Thr Leu Tyr Gln Asn Val Thr Ile Glu Gln Gly Arg Ile Val Leu Arg
                485                 490                 495
Glu Lys Ala Lys Leu Ser Val Asn Ser Leu Ser Gln Thr Gly Gly Ser
                500                 505                 510
Leu Tyr Met Glu Ala Gly Ser Thr Trp Asp Phe Val Thr Pro Gln Pro
            515                 520                 525
Pro Gln Gln Pro Pro Ala Ala Asn Gln Leu Ile Thr Leu Ser Asn Leu
            530                 535                 540
His Leu Ser Leu Ser Ser Leu Leu Ala Asn Asn Ala Val Thr Asn Pro
545                 550                 555                 560
Pro Thr Asn Pro Pro Ala Gln Asp Ser His Pro Ala Val Ile Gly Ser
                565                 570                 575
Thr Thr Ala Gly Ser Val Thr Ile Ser Gly Pro Ile Phe Phe Glu Asp
                580                 585                 590
Leu Asp Asp Thr Ala Tyr Asp Arg Tyr Asp Trp Leu Gly Ser Asn Gln
                595                 600                 605
Lys Ile Asn Val Leu Lys Leu Gln Leu Gly Thr Lys Pro Pro Ala Asn
            610                 615                 620
Ala Pro Ser Asp Leu Thr Leu Gly Asn Glu Met Pro Lys Tyr Gly Tyr
625                 630                 635                 640
Gln Gly Ser Trp Lys Leu Ala Trp Asp Pro Asn Thr Ala Asn Asn Gly
                645                 650                 655
Pro Tyr Thr Leu Lys Ala Thr Trp Thr Lys Thr Gly Tyr Asn Pro Gly
                660                 665                 670
Pro Glu Arg Val Ala Ser Leu Val Pro Asn Ser Leu Trp Gly Ser Ile
            675                 680                 685
Leu Asp Ile Arg Ser Ala His Ser Ala Ile Gln Ala Ser Val Asp Gly
            690                 695                 700
Arg Ser Tyr Cys Arg Gly Leu Trp Val Ser Gly Val Ser Asn Phe Phe
705                 710                 715                 720
Tyr His Asp Arg Asp Ala Leu Gly Gln Gly Tyr Arg Tyr Ile Ser Gly
                725                 730                 735
Gly Tyr Ser Leu Gly Ala Asn Ser Tyr Phe Gly Ser Met Phe Gly
                740                 745                 750
Leu Ala Phe Thr Glu Val Phe Gly Arg Ser Lys Asp Tyr Val Val Cys
                755                 760                 765
Arg Ser Asn His His Ala Cys Ile Gly Ser Val Tyr Leu Ser Thr Gln
            770                 775                 780
Gln Ala Leu Cys Gly Ser Tyr Leu Phe Gly Asp Ala Phe Ile Arg Ala
785                 790                 795                 800
Ser Tyr Gly Phe Gly Asn Gln His Met Lys Thr Ser Tyr Thr Phe Ala
                805                 810                 815
```

```
Glu Glu Ser Asp Val Arg Trp Asp Asn Asn Cys Leu Ala Gly Glu Ile
            820                 825                 830

Gly Ala Gly Leu Pro Ile Val Ile Thr Pro Ser Lys Leu Tyr Leu Asn
        835                 840                 845

Glu Leu Arg Pro Phe Val Gln Ala Glu Phe Ser Tyr Ala Asp His Glu
    850                 855                 860

Ser Phe Thr Glu Glu Gly Asp Gln Ala Arg Ala Phe Lys Ser Gly His
865             870                 875                     880

Leu Leu Asn Leu Ser Val Pro Val Gly Val Lys Phe Asp Arg Cys Ser
            885                 890                 895

Ser Thr His Pro Asn Lys Tyr Ser Phe Met Ala Ala Tyr Ile Cys Asp
            900                 905                 910

Ala Tyr Arg Thr Ile Ser Gly Thr Glu Thr Thr Leu Leu Ser His Gln
        915                 920                 925

Glu Thr Trp Thr Thr Asp Ala Phe His Leu Ala Arg His Gly Val Val
    930                 935                 940

Val Arg Gly Ser Met Tyr Ala Ser Leu Thr Ser Asn Ile Glu Val Tyr
945             950                 955                     960

Gly His Gly Arg Tyr Glu Tyr Arg Asp Ala Ser Arg Gly Tyr Gly Leu
            965                 970                 975

Ser Ala Gly Ser Arg Val Arg Phe
            980
```